US010610689B2

(12) United States Patent
Mika et al.

(10) Patent No.: US 10,610,689 B2
(45) Date of Patent: *Apr. 7, 2020

(54) METHODS AND SYSTEMS FOR LOWERING BLOOD PRESSURE THROUGH REDUCTION OF VENTRICLE FILLING

(71) Applicant: BackBeat Medical, Inc., New Hope, PA (US)

(72) Inventors: Yuval Mika, Closter, NJ (US); Darren Sherman, Fort Lauderdale, FL (US); Robert S. Schwartz, Inver Grove Heights, MN (US); Robert A. Van Tassel, Excelsior, MN (US); Daniel Burkhoff, Manhattan, NY (US)

(73) Assignee: BackBeat Medical, Inc., New Hope, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/911,249

(22) Filed: Mar. 5, 2018

(65) Prior Publication Data
US 2018/0256899 A1 Sep. 13, 2018

Related U.S. Application Data

(63) Continuation of application No. 14/652,856, filed as application No. PCT/US2013/076600 on Dec. 19, 2013, now Pat. No. 9,937,351.

(51) Int. Cl.
*A61N 1/365* (2006.01)
*A61N 1/368* (2006.01)
(Continued)

(52) U.S. Cl.
CPC ........ *A61N 1/36564* (2013.01); *A61F 2/2412* (2013.01); *A61F 2/2424* (2013.01);
(Continued)

(58) Field of Classification Search
CPC ................ A61N 1/365; A61N 1/36564; A61N 1/36514; A61N 1/3684; A61N 1/3682;
(Continued)

(56) References Cited

U.S. PATENT DOCUMENTS

| 3,683,934 A | 8/1972 | Bukowiecki et al. |
| 3,814,106 A | 6/1974 | Berkovits |

(Continued)

FOREIGN PATENT DOCUMENTS

| AU | 2013361318 | 8/2018 |
| AU | 2014367229 B2 | 7/2019 |

(Continued)

OTHER PUBLICATIONS

Arbel E.R., et al., "Successful Treatment of Drug-Resistant Atrial Tachycardia and Intractable Congestive Heart Failure with Permanent Coupled Atrial Pacing," Journal of the American College of Cardiology, 1978, vol. 41 (2), pp. 336-340.

(Continued)

*Primary Examiner* — Carl H Layno
*Assistant Examiner* — Jon Eric C Morales
(74) *Attorney, Agent, or Firm* — Plumsea Law Group, LLC

(57) ABSTRACT

Systems and methods for reducing ventricle filling volume are disclosed. In some embodiments, a stimulation circuit may be used to stimulate a patient's heart to reduce ventricle filling volume or even blood pressure. When the heart is stimulated at a consistent rate to reduce blood pressure, the cardiovascular system may over time adapt to the stimulation and revert back to the higher blood pressure. In some embodiments, the stimulation pattern may be configured to be inconsistent such that the adaptation response of the heart is reduced or even prevented. In some embodiments, a stimulation circuit may be used to stimulate a patient's heart (Continued)

to cause at least a portion of an atrial contraction to occur while the atrioventricular valve is closed. Such an atrial contraction may deposit less blood into the corresponding ventricle than when the atrioventricular valve is opened throughout an atrial contraction.

23 Claims, 12 Drawing Sheets

(51) Int. Cl.
  *A61N 1/36* (2006.01)
  *A61F 2/24* (2006.01)
(52) U.S. Cl.
  CPC ......... *A61N 1/3682* (2013.01); *A61N 1/3684* (2013.01); *A61N 1/36117* (2013.01); *A61N 1/36514* (2013.01); *A61N 1/36528* (2013.01); *A61N 1/36571* (2013.01); *A61N 1/36578* (2013.01); *A61N 1/36585* (2013.01); *A61F 2250/0013* (2013.01)
(58) Field of Classification Search
  CPC ............ A61N 1/36117; A61N 1/36571; A61N 1/36528; A61N 1/36578; A61N 1/36585; A61F 2/2424; A61F 2/2412; A61F 2250/0013
  USPC .................................................. 607/9, 17, 23
  See application file for complete search history.

(56) References Cited

U.S. PATENT DOCUMENTS

| | | |
|---|---|---|
| 3,939,844 A | 2/1976 | Pequignot |
| 4,407,287 A | 10/1983 | Herpers |
| 4,712,555 A | 12/1987 | Thornander et al. |
| 4,719,921 A | 1/1988 | Chirife |
| 4,899,752 A | 2/1990 | Cohen |
| 5,063,239 A | 11/1991 | Schwenner et al. |
| 5,163,429 A | 11/1992 | Cohen |
| 5,213,098 A | 5/1993 | Bennett et al. |
| 5,318,595 A | 6/1994 | Ferek-Petric et al. |
| 5,584,868 A | 12/1996 | Salo et al. |
| 5,601,613 A | 2/1997 | Florio et al. |
| 5,601,615 A | 2/1997 | Markowitz et al. |
| 5,612,380 A | 3/1997 | Lerner et al. |
| 5,713,928 A | 2/1998 | Bonnet et al. |
| 5,800,334 A | 9/1998 | Wilk |
| 5,891,176 A | 4/1999 | Bornzin |
| 5,928,271 A | 7/1999 | Hess et al. |
| 5,971,911 A | 10/1999 | Wilk |
| 6,045,531 A | 4/2000 | Davis |
| 6,241,678 B1 | 6/2001 | Afremov et al. |
| 6,271,015 B1 | 8/2001 | Gilula et al. |
| 6,314,322 B1 | 11/2001 | Rosenberg |
| 6,377,852 B1 | 4/2002 | Bornzin et al. |
| 6,450,942 B1 | 9/2002 | Lapanashvili et al. |
| 6,507,756 B1 | 1/2003 | Heynen et al. |
| 6,580,946 B2 | 6/2003 | Struble |
| 6,628,988 B2 | 9/2003 | Kramer et al. |
| 6,666,826 B2 | 12/2003 | Salo et al. |
| 6,668,195 B2 | 12/2003 | Warman et al. |
| 6,699,682 B2 | 3/2004 | Gilula et al. |
| 6,701,187 B1 | 3/2004 | Bornzin et al. |
| 6,795,732 B2 | 9/2004 | Stadler et al. |
| 6,832,113 B2 | 12/2004 | Belalcazar |
| 7,001,611 B2 | 2/2006 | Kiso et al. |
| 7,092,759 B2 | 8/2006 | Nehls et al. |
| 7,096,064 B2 | 8/2006 | Deno et al. |
| 7,098,233 B2 | 8/2006 | Di Cesare et al. |
| 7,103,410 B2 | 9/2006 | Kramer et al. |
| 7,184,832 B2 | 2/2007 | Deno et al. |
| 7,233,824 B2 | 6/2007 | Kleckner et al. |
| 7,286,873 B2 | 10/2007 | Havel et al. |
| 7,289,849 B2 | 10/2007 | Baynham et al. |
| 7,346,394 B2 | 3/2008 | Liu et al. |
| 7,348,173 B2 | 3/2008 | Gilula et al. |
| 7,363,077 B1 | 4/2008 | Min et al. |
| 7,548,782 B2 | 6/2009 | Kramer et al. |
| 7,674,222 B2 | 3/2010 | Nikolic et al. |
| 7,676,264 B1 | 3/2010 | Pillai et al. |
| 7,711,420 B2 | 5/2010 | Baynham et al. |
| 7,725,173 B2 | 5/2010 | Viertio-Oja et al. |
| 7,725,185 B2 | 5/2010 | Liu et al. |
| 7,765,008 B2 | 7/2010 | Ben-Haim et al. |
| 7,869,874 B2 | 1/2011 | Levin et al. |
| 8,027,724 B2 | 9/2011 | Wei et al. |
| 8,046,070 B2 | 10/2011 | Salo et al. |
| 8,086,315 B2 | 12/2011 | Schwartz et al. |
| 8,165,674 B2 | 4/2012 | Levin et al. |
| 8,187,160 B2 | 5/2012 | Criscione et al. |
| 8,340,763 B2 | 12/2012 | Levin et al. |
| 8,428,729 B2 | 4/2013 | Schwartz et al. |
| 8,515,536 B2 | 8/2013 | Levin et al. |
| 8,521,280 B2 | 8/2013 | Levin et al. |
| 9,008,769 B2 | 4/2015 | Mika et al. |
| 9,320,903 B2 | 4/2016 | Schwartz et al. |
| 9,333,352 B2 | 5/2016 | Mika et al. |
| 9,370,661 B2 | 6/2016 | Levin et al. |
| 9,370,662 B2 | 6/2016 | Mika et al. |
| 9,427,586 B2 | 8/2016 | Levin et al. |
| 9,526,900 B2 | 12/2016 | Mika et al. |
| 9,656,086 B2 | 5/2017 | Mika et al. |
| 9,687,636 B2 | 6/2017 | Levin et al. |
| 9,731,136 B2 | 8/2017 | Levin et al. |
| 9,878,162 B2 | 1/2018 | Mika et al. |
| 9,937,351 B2 | 4/2018 | Mika et al. |
| 10,071,250 B2 | 9/2018 | Mika et al. |
| 10,232,183 B2 | 3/2019 | Schwartz et al. |
| 10,252,060 B2 | 4/2019 | Levin et al. |
| 10,252,061 B2 | 4/2019 | Mika et al. |
| 10,342,982 B2 | 7/2019 | Mika et al. |
| 10,369,333 B2 | 8/2019 | Levin et al. |
| 10,441,794 B2 | 10/2019 | Mika et al. |
| 10,485,658 B2 | 11/2019 | Mika et al. |
| 2002/0161410 A1 | 10/2002 | Kramer et al. |
| 2002/0173826 A1 | 11/2002 | Lincoln et al. |
| 2003/0060858 A1 | 3/2003 | Kieval et al. |
| 2003/0083700 A1 | 5/2003 | Hill et al. |
| 2003/0144702 A1 | 7/2003 | Yu et al. |
| 2003/0144703 A1 | 7/2003 | Yu et al. |
| 2003/0176896 A1 | 9/2003 | Lincoln et al. |
| 2003/0199934 A1 | 10/2003 | Struble et al. |
| 2004/0015081 A1 | 1/2004 | Kramer et al. |
| 2004/0044361 A1 | 3/2004 | Frazier et al. |
| 2004/0049235 A1 | 3/2004 | Deno et al. |
| 2004/0138715 A1 | 7/2004 | Van et al. |
| 2004/0167410 A1 | 8/2004 | Hettrick |
| 2004/0186523 A1 | 9/2004 | Florio |
| 2004/0215255 A1 | 10/2004 | Vries |
| 2004/0215266 A1 | 10/2004 | Struble et al. |
| 2004/0215268 A1 | 10/2004 | Corbucci |
| 2005/0038478 A1 | 2/2005 | Klepfer et al. |
| 2005/0070952 A1 | 3/2005 | Devellian |
| 2005/0075676 A1 | 4/2005 | Deno et al. |
| 2005/0090872 A1 | 4/2005 | Deno et al. |
| 2005/0101998 A1 | 5/2005 | Kleckner et al. |
| 2005/0102002 A1 | 5/2005 | Salo et al. |
| 2005/0119285 A1 | 6/2005 | Matos et al. |
| 2005/0143785 A1 | 6/2005 | Libbus |
| 2005/0149130 A1 | 7/2005 | Libbus |
| 2005/0149131 A1 | 7/2005 | Libbus et al. |
| 2005/0222640 A1 | 10/2005 | Schwartz et al. |
| 2005/0234543 A1 | 10/2005 | Glaser et al. |
| 2006/0173502 A1 | 8/2006 | Baynham et al. |
| 2006/0173504 A1 | 8/2006 | Zhu et al. |
| 2006/0247702 A1 | 11/2006 | Stegemann et al. |
| 2006/0264980 A1 | 11/2006 | Khairkhahan et al. |
| 2007/0073352 A1 | 3/2007 | Euler et al. |
| 2007/0083243 A1 | 4/2007 | Prakash et al. |
| 2007/0299475 A1 | 12/2007 | Levin et al. |
| 2007/0299477 A1 | 12/2007 | Kleckner et al. |
| 2008/0027488 A1 | 1/2008 | Coles et al. |

(56) References Cited

U.S. PATENT DOCUMENTS

| | | |
|---|---|---|
| 2008/0077187 A1 | 3/2008 | Levin et al. |
| 2008/0109043 A1 | 5/2008 | Salo et al. |
| 2009/0018608 A1* | 1/2009 | Schwartz ............ A61N 1/3627 607/44 |
| 2009/0036940 A1 | 2/2009 | Wei et al. |
| 2009/0069859 A1 | 3/2009 | Whinnett et al. |
| 2009/0082823 A1 | 3/2009 | Shuros et al. |
| 2009/0118783 A1 | 5/2009 | Patangay et al. |
| 2009/0207028 A1 | 8/2009 | Kubey et al. |
| 2009/0240298 A1 | 9/2009 | Lian et al. |
| 2009/0247893 A1 | 10/2009 | Lapinlampi et al. |
| 2009/0254141 A1 | 10/2009 | Kramer et al. |
| 2009/0281440 A1 | 11/2009 | Farazi et al. |
| 2009/0281591 A1 | 11/2009 | Shuros et al. |
| 2009/0318995 A1 | 12/2009 | Keel et al. |
| 2010/0069989 A1 | 3/2010 | Shipley et al. |
| 2010/0087889 A1 | 4/2010 | Maskara et al. |
| 2010/0094370 A1 | 4/2010 | Levin et al. |
| 2010/0121397 A1 | 5/2010 | Cholette |
| 2010/0121402 A1 | 5/2010 | Arcot-Krishnamurthy et al. |
| 2010/0204741 A1 | 8/2010 | Tweden et al. |
| 2011/0144712 A1 | 6/2011 | Stahmann et al. |
| 2011/0160787 A1 | 6/2011 | Greenhut et al. |
| 2011/0172731 A1 | 7/2011 | Levin et al. |
| 2012/0041502 A1 | 2/2012 | Schwartz et al. |
| 2012/0109237 A1 | 5/2012 | Xiao et al. |
| 2012/0215272 A1 | 8/2012 | Levin et al. |
| 2013/0331901 A1 | 12/2013 | Levin et al. |
| 2014/0128934 A1 | 5/2014 | Schwartz et al. |
| 2014/0163600 A1 | 6/2014 | Levin et al. |
| 2014/0163636 A1 | 6/2014 | Levin et al. |
| 2014/0180353 A1 | 6/2014 | Mika et al. |
| 2015/0174410 A1 | 6/2015 | Mika et al. |
| 2015/0335895 A1 | 11/2015 | Mika et al. |
| 2015/0360035 A1 | 12/2015 | Mika et al. |
| 2016/0129084 A1 | 5/2016 | Caggiano et al. |
| 2016/0220824 A1 | 8/2016 | Schwartz et al. |
| 2016/0243368 A1 | 8/2016 | Mika et al. |
| 2016/0263383 A1 | 9/2016 | Levin et al. |
| 2016/0339244 A1 | 11/2016 | Levin et al. |
| 2017/0072203 A1 | 3/2017 | Mika et al. |
| 2017/0080235 A1 | 3/2017 | Mika et al. |
| 2017/0239481 A1 | 8/2017 | Mika et al. |
| 2017/0274190 A1 | 9/2017 | Levin et al. |
| 2017/0291032 A1 | 10/2017 | Levin et al. |
| 2017/0304048 A1 | 10/2017 | Mika et al. |
| 2018/0185652 A1 | 7/2018 | Mika et al. |
| 2019/0001141 A1 | 1/2019 | Mika et al. |
| 2019/0255334 A1 | 8/2019 | Schwartz et al. |
| 2019/0269927 A1 | 9/2019 | Mika et al. |
| 2019/0275336 A1 | 9/2019 | Mika et al. |
| 2019/0351237 A1 | 11/2019 | Mika et al. |

FOREIGN PATENT DOCUMENTS

| | | |
|---|---|---|
| CA | 2933278 A1 | 6/2015 |
| CN | 1662278 A | 8/2005 |
| CN | 106029165 A | 10/2016 |
| CN | 104968392 B | 11/2017 |
| CN | 107715299 A | 2/2018 |
| CN | 108025173 A | 5/2018 |
| CN | 106029165 B | 11/2018 |
| CN | 109364374 A | 2/2019 |
| EP | 0532148 | 3/1993 |
| EP | 2241348 | 10/2010 |
| EP | 2934669 B1 | 6/2017 |
| EP | 3238777 A2 | 11/2017 |
| EP | 3082949 B1 | 11/2018 |
| EP | 3461531 A1 | 4/2019 |
| EP | 3238777 B1 | 10/2019 |
| HK | 1226016 B2 | 10/2019 |
| JP | 2007-519441 A | 7/2007 |
| JP | 2007-531609 A | 11/2007 |
| JP | 2010-508979 A | 3/2010 |
| JP | 2010-512958 A | 4/2010 |
| JP | 2010-536481 A | 12/2010 |
| JP | 2016-540589 A | 12/2016 |
| JP | 2019-042579 | 3/2019 |
| JP | 6510421 B2 | 5/2019 |
| JP | 2019-517842 | 6/2019 |
| JP | 2019-111408 | 7/2019 |
| WO | 9944682 A1 | 9/1999 |
| WO | 03000252 A1 | 1/2003 |
| WO | 2009035515 A1 | 3/2005 |
| WO | 2005063332 A1 | 7/2005 |
| WO | 2005097256 A2 | 10/2005 |
| WO | 2007021258 A1 | 2/2007 |
| WO | 2008057631 A1 | 5/2008 |
| WO | 2008079370 A1 | 7/2008 |
| WO | 2014100429 A1 | 6/2014 |
| WO | 2015094401 A1 | 6/2015 |
| WO | 2017044794 A1 | 3/2017 |
| WO | 2017184912 A2 | 10/2017 |

OTHER PUBLICATIONS

Auricchio A., et al., "Cardiac Resyncbronization Therapy Restores Optimal Atrioventricular Mechanical Timing in Heart Failure Patients With Ventricular Conduction Delay," Journal of the American College of Cardiology, 2002, vol. 39 (7), pp. 1163-1169.

Auricchio A., et al., "Effect of Pacing Chamber and Atrioventricular Delay on Acute Systolic Function of Paced Patients With Congestive Heart Failure," Circulation—Journal of the American Heart Association, 1999, vol. 99 (23), pp. 2993-3001.

Braunwald E., et al., "Editorial: Paired Electrical Stimulation of the Heart: A Physiologic Riddle and a Clinical Challenge," Circulation, 1965, vol. 32 (5), pp. 677-681.

Calderone A., et al., "The Therapeutic Effect of Natriuretic Peptides in Heart Failure; Differential Regulation of Endothelial and Inducible Nitric Oxide Synthases," Heart Failure Reviews, 2003, vol. 8 (1), pp. 55-70.

Co-pending U.S. Appl. No. 13/688,978, filed Nov. 29, 2012.

Han B., et al., "Cardiovascular Effects of Natriuretic Peptides and Their Interrelation with Endothelin-1," Cardiovascular Drugs and Therapy, 2003, vol. 17 (1), pp. 41-42.

Information Manual, Model 5837 R-Wave Coupled Pulse Generator, Prelim. Ed. III , Medtronic, 1965, 20 pages.

International Preliminary Report on Patentability for Application No. PCT/US2005/028415, dated Feb. 21, 2008.

International Search Report and Written Opinion for Application No. PCT/US2005/28415, dated Jan. 19, 2006.

International Search Report and Written Opinion for Application No. PCT/US2014/042777, dated Jan. 2, 2015.

Invitation to Pay Additional Fees mailed Oct. 17, 2014 in International Application No. PCT/US2014/042777.

Kerwin W.F., et al., "Ventricular Contraction Abnormalities in Dilated Cardiomyopathy: Effect of Biventricular Pacing to Correct Interventricular Dyssynchrony," Journal of the American College of Cardiology, 2000, vol. 35 (5), pp. 1221-1227.

Lister J.W., et al., "The Hemodynamic Effect of Slowing the Heart Rate by Paired or Coupled Stimulation of the Atria," American Heart Journal, 1967, vol. 73 (3), pp. 362-368.

Liu L., et al., "Left Ventricular Resynchronization Therapy in a Canine Model of Left Bundle Branch Block," American Journal of Physiology—Heart and Circulatory Physiology, 2002, vol. 282 (6), pp. H2238-H2244.

Lopez J.F., et al., "Reducing Heart Rate of the Dog by Electrical Stimulation," Circulation Research, 1964, vol. 15, pp. 414-429.

Nishimura K., et al., "Atrial Pacing Stimulates Secretion of Atrial Natriuretic Polypeptide without Elevation of Atrial Pressure in Awake Dogs with Experimental Complete Atrioventricular Block," Circulation Research, 1990, vol. 66 (1), pp. 115-122.

Non-Final Office Action dated Jun. 4, 2015 for U.S. Appl. No. 13/957,499, filed Aug. 2, 2013.

Non-Final Office Action dated May 4, 2015 for U.S. Appl. No. 13/854,283, filed Apr. 1, 2013.

(56) References Cited

OTHER PUBLICATIONS

Non-Final Office Action dated Jun. 10, 2015 for U.S. Appl. No. 13/960,015, filed Aug. 6, 2013.
Notice of Allowance dated Dec. 16, 2014 in U.S. Appl. No. 13/826,215.
O'Cochlain B., et al., "The Effect of Variation in the Interval Between Right and Left Ventricular Activation on Paced QRS Duration," Journal of Pacing and Clinical Electrophysiology, 2001, vol. 24 (12), pp. 1780-1782.
Office Action dated Jan. 29, 2015 for U.S. Appl. No. 13/688,978, filed Nov. 29, 2012.
Pappone C., et al., "Cardiac Pacing in Heart Failure Patients with Left Bundle Branch Block: Impact of Pacing Site for Optimizing Left Ventricular Resynchronization," Italian Heart Journal, 2000, vol. 1 (7), pp. 464-469.
PCT Notification Concerning Transmittal of International Preliminary Report on Patentability (IPER), International Application No. PCT/US2005/028415, from the International Bureau dated Feb. 21, 2008.
PCT Notification of Transmittal of the International Search Report and the Written Opinion of the International Searching Authority; Declaration of Non-Establishment of International Search Report; and PCT Written Opinion of International Searching Authority, dated Apr. 24, 2014 in International Application No. PCT/US2013/076600.
Perego G.B., et al., "Simultaneous Vs. Sequential Biventricular Pacing in Dilated Cardiomyopathy: An Acute Hemodynamic Study," The European Journal of Heart Failure, 2003, vol. 5 (3), pp. 305-313.
Schoonderwoerd B.A., et al., "Atrial Natriuretic Peptides During Experimental Atrial Tachycardia: Role of Developing Tachycardiomyopathy," Journal of Cardiovascular Electrophysiology, 2004, vol. 15 (8), pp. 927-932.
Siddons et al., Cardiac Pacemakers, Pub. No. 680 of American Lecture Series, 1968, Thomas C. Publisher, pp. 200-217.
U.S. Appl. No. 13/688,978 to Levin et al., filed Nov. 29, 2012.
Verbeek X.A., et al., "Intra-Ventricular Resynchronization for Optimal Left Ventricular Function During Pacing in Experimental Left Bundle Branch Block," American Journal of Physiology—Heart and Circulatory Physiology, 2003, vol. 42 (3), pp. 558-567.
Verbeek X.A., et al., "Quantification of Interventricular Asynchrony during LBBB and Ventricular Pacing," American Journal of Physiology—Heart and Circulatory Physiology, 2002, vol. 283 (4), pp. H1370-H1378.
Whinnett Z.I., et al., "Haemodynamic Effects of Changes in Atrioventricular and Interventricular Delay in Cardiac Resynchronization Therapy Show a Consistent Pattern: Analysis of Shape, Magnitude and Relative Importance of Atrioventricular and Interventricular Delay," Heart, 2006, vol. 92 (11), pp. 1628-1634.
Willems R., et al., "Different Patterns of Angiotensin II and Atrial Natriuretic Peptide Secretion in a Sheep Model of Atrial Fibrillation," Journal of the American College of Cardiology, 2001, vol. 12 (12), pp. 1387-1392.
Zupan I., et al., "Effects of Systolic Atrial Function on Plasma Renin Activity and Natriuretic Peptide Secretion after High Rate Atrial and Ventricular Pacing in Dogs," Pacing and Clinical Electrophysiology, 2005, vol. 28 (Supp 1), pp. S270-S274.
Office Action dated Jul. 13, 2015 in U.S. Appl. No. 14/642,952.
Office Action dated Aug. 14, 2015 in U.S. Appl. No. 13/688,978.
Amendment filed Oct. 9, 2015 in U.S. Appl. No. 14/642,952.
Amendment filed Oct. 16, 2015 in U.S. Appl. No. 13/854,283.
Amendment filed Nov. 5, 2015 in U.S. Appl. No. 13/688,978.
Office Action dated Nov. 4, 2015 in U.S. Appl. No. 14/427,478.
Amendment filed Nov. 30, 2015 in U.S. Appl. No. 13/957,499.
Amendment filed Dec. 3, 2015 in U.S. Appl. No. 13/960,015.
Notice of Allowance dated Dec. 18, 2015 in U.S. Appl. No. 13/854,281.
Notice of Allowance dated Jan. 8, 2016 in U.S. Appl. No. 14/642,952.
Amendment filed Jan. 13, 2016 in U.S. Appl. No. 14/427,478.
Final Office Action dated Jan. 20, 2016 in U.S. Appl. No. 13/960,015.
Notice of Allowance dated Feb. 12, 2016 in U.S. Appl. No. 13/688,978.
Notice of Allowance dated Feb. 12, 2016 in U.S. Appl. No. 14/427,478.
Office Action dated Mar. 4, 2016 in U.S. Appl. No. 14/667,931.
Extended European Search Report dated Nov. 3, 2017 in European Patent Application No. 17169068.8.
Notice of Allowance dated Dec. 6, 2017 in U.S. Appl. No. 14/652,856.
Supplemental Notice of Allowance dated Jan. 29, 2018 in U.S. Appl. No. 14/652,856.
Amendment filed Apr. 7, 2016 in U.S. Appl. No. 13/960,015.
Notice of Allowance dated Apr. 13, 2016 in U.S. Appl. No. 13/957,499.
Advisory Action dated Apr. 18, 2016 in U.S. Appl. No. 13/960,015.
Amendment filed Jun. 6, 2016 in U.S. Appl. No. 13/960,015.
Office Action dated May 27, 2016 in European Patent Application No. 13826807.3.
Office Action dated Jun. 28, 2016 in U.S. Appl. No. 15/143,742.
Office Action dated Jul. 21, 2016 in U.S. Appl. No. 13/960,015.
Amendment filed Jul. 25, 2016 in U.S. Appl. No. 14/667,931.
Office Action dated Jul. 27, 2016 in U.S. Appl. No. 15/163,078.
Notice of Allowance dated Aug. 17, 2016 in U.S. Appl. No. 14/667,931.
Office Action dated Sep. 5, 2016 in Chinese Patent Application No. 201380072479.3, and English translation thereof.
Amendment filed Sep. 27, 2016 in U.S. Appl. No. 15/143,742.
Response to Office Action filed Sep. 27, 2016 in European Patent Application No. 13826807.3.
Amendment filed Oct. 26, 2016 in U.S. Appl. No. 15/163,078.
PCT Notification of Transmittal of the International Search Report and the Written Opinion of the International Searching Authority; International Search Report; and Written Opinion, dated Nov. 28, 2016 in International Application No. PCT/US2016/051023.
Notice of Intention to Grant dated Jan. 3, 2017 in European Patent Application No. 13826807.3.
Notice of Allowance dated Jan. 18, 2017 in U.S. Appl. No. 15/143,742.
Amendment filed Jan. 19, 2017 in U.S. Appl. No. 13/960,015.
Response to Office Action filed Jan. 19, 2017 in Chinese Patent Application No. 2013800724793, and English translation thereof.
Notice of Allowance dated Feb. 22, 2017 in U.S. Appl. No. 13/960,015.
Notice of Allowance dated Mar. 15, 2017 in U.S. Appl. No. 15/163,078.
Office Action dated Mar. 24, 2017 in U.S. Appl. No. 15/372,603.
Decision to Grant dated May 26, 2017 in European Patent Application No. 13826807.3.
Amendment filed Jun. 26, 2017 in U.S. Appl. No. 15/372,603.
Partial European Search Report dated Jul. 25, 2017 in European Patent Application No. 17169068.8.
Extended European Search Report dated Jul. 25, 2017 in European Patent Application No. 14871226.8.
Notice of Allowance dated Sep. 11, 2017 in U.S. Appl. 15/372,603.
Office Action dated Sep. 21, 2017 in U.S. Appl. No. 15/628,870.
Office Action dated Sep. 27, 2017 in U.S. Appl. No. 15/589,134.
Office Action dated Oct. 20, 2017 in U.S. Appl. No. 15/092,737.
PCT Invitation to Pay Additional Fees mailed Aug. 3, 2017 in International Application No. PCT/US2017/028715.
Office Action dated Aug. 11, 2017 in European Patent Application No. 14871226.8.
International Search Report and Written Opinion dated Oct. 3, 2017 in International Application No. PCT/US2017/028715.
Chaliki, HP et al.; "Pulmonary Venous Pressure: Relationship to Pulmonary Artery, Pulmonary Wedge, and Left Atrial Pressure in Normal, Lightly Sedated Dogs"; Catheterization and Cardiovascular Interventions; vol. 56, Issue 3; Jun. 17, 2002; p. 432, Abstract.
Office Action dated Oct. 19, 2017 in Japanese Patent Application No. 2015-549718, and English translation thereof.
Office Action dated Nov. 6, 2017 in Australian Patent Application No. 2013361318.
Office Action dated Nov. 21, 2017 in U.S. Appl. No. 15/259,282.
Response to Restriction and Election of Species Requirement filed Dec. 8, 2017 in U.S. Appl. No. 15/092,737.
Office Action dated Dec. 27, 2017 in U.S. Appl. No. 15/092,737.

(56) References Cited

OTHER PUBLICATIONS

Amendment 15/628,870. and Declaration Under 37 CFR 1.132 filed Jan. 22, 2018 in U.S. Appl. No. 15/628,870.
Amendment filed Jan. 26, 2018 in U.S. Appl. No. 15/589,134.
Response to Office Action filed Feb. 7, 2018 in European Patent Application No. 14 871 226.8.
Response to Office Action filed Feb. 21, 2018 in U.S. Appl. No. 15/259,282.
Office Action dated Feb. 24, 2018 in Chinese Patent Application No. 201480075987.1, and English translation thereof.
Notification Concerning Transmittal of International Preliminary Report on Patentability (IPRP) dated Mar. 22, 2018 in International Application No. PCT/2016/051023.
Response to Office Action filed Mar. 28, 2018 in Japanese Patent Application No. 2015-549718, with machine English translation of Remarks and English translation of Amended Claims.
Interview Summary dated Apr. 3, 2018 in U.S. Appl. No. 15/092,737.
Office Action dated Apr. 10, 2018 in U.S. Appl. No. 15/259,282.
Office Action dated Jun. 16, 2017 in U.S. Appl. 14/652,856.
Amendment filed Sep. 18, 2017 in U.S. Appl. No. 14/652,856.
Response to Examination Report filed Apr. 23, 2018 in Australian Patent Application No. 2013361318.
Amendment filed Apr. 24, 2018 in U.S. Appl. No. 15/092,737.
Notice of Allowance dated May 2, 2018 in U.S. Appl. No. 15/589,134.
Notice of Acceptance dated May 7, 2018 in Australian Patent Application No. 2013361318.
Notice of Intention to Grant dated May 7, 2018 in European Patent Application No. 14871226.8.
Office Action dated May 10, 2018 in Japanese Patent Application No. 2016-539929, and English translation thereof.
Office Action dated May 16, 2018 in U.S. Appl. No. 15/628,870.
Office Action dated May 16, 2018 in U.S. Appl. No. 15/851,787.
Response to Extended European Search Report filed May 25, 2018 in European Patent Application No. 17 169 068.8.
Response to Office Action filed Jul. 11, 2018 in Chinese Patent Application No. 201480075987.1, and English machine translation thereof.
Notice of Allowance dated Nov. 26, 2018 in U.S. Appl. No. 15/628,870.
Amendment and Response to Restriction Requirement filed Nov. 26, 2018 in U.S. Appl. No. 15/226,056.
Response to Restriction Requirement filed Dec. 19, 2018 in U.S. Appl. No. 15/492,802.
Office Action dated Dec. 27, 2018 in U.S. Appl. No. 16/124,283.
Office Action dated Jan. 11, 2019 in U.S. Appl. No. 15/226,056.
Interview Summary dated Jan. 22, 2019 in U.S. Appl. No. 15/259,282.
Decision to Grant a Patent dated Dec. 6, 2018 in Japanese Patent Application No. 2016-539929, with English translation thereof.
First Examination Report dated Dec. 12, 2018 in Australian Patent Application No. 2014367229.
Amendment filed Aug. 9, 2018 in U.S. Appl. No. 15/259,282.
Response to Office Action filed Aug. 13, 2018 in U.S. Appl. No. 15/628,870.
Amendment filed Aug. 13, 2018 in U.S. Appl. No. 15/851,787.
Restriction Requirement dated Sep. 24, 2018 in U.S. Appl. No. 15/226,056.
Final Office Action dated Oct. 1, 2018 in U.S. Appl. No. 15/259,282.
Response to Final Office Action filed Oct. 24, 2018 in Japanese Patent Application No. 2015-549718, with English Translation of Amended Claims and English Machine Translation of Remarks.
Notice of Allowance dated Oct. 29, 2018 in U.S. Appl. No. 15/092,737.
Response to Office Action filed Oct. 29, 2018 in Japanese Patent Application No. 2016-539929, with English Translation of Amended Claims and English Machine Translation of Remarks.
Notice of Allowance dated Oct. 31, 2018 in U.S. Appl. No. 15/851,787.
Restriction Requirement dated Nov. 1, 2018 in U.S. Appl. No. 15/492,802.
Final Office Action dated Aug. 28, 2018 in Japanese Patent No. 2015-549718, and English translation thereof.
Notification Concerning Transmittal of International Preliminary Report on Patentability (IPRP) dated Nov. 1, 2018 in International Application No. PCT/2017/028715.
Notice of Allowance dated Jun. 5, 2019 in U.S. Appl. No. 16/124,283.
Amendment filed Jun. 14, 2019 in U.S. Appl. No. 15/492,802.
Notice of Allowance dated Jul. 2, 2019 in U.S. Appl. No. 15/492,802.
Extended European Search Report dated Jan. 21, 2019 in European Patent Application No. 18205392.6.
Decision to Grant a Patent dated Mar. 1, 2019 in Japanese Patent Application No. 2015-549718, and English translation thereof.
Notice of Acceptance dated Mar. 22, 2019 in Australian Patent Application No. 2014367229.
Extended European Search Report dated Mar. 27, 2019 in European Patent Application No. 16845150.8.
Amendment After Final Rejection filed Feb. 1, 2019 in U.S. Appl. No. 15/259,282.
Response to Examination Report filed Feb. 22, 2019 in Australian Patent Application No. 2014367229.
Notice of Allowance dated Mar. 1, 2019 in U.S. Appl. No. 15/259,282.
Office Action dated Mar. 18, 2019 in U.S. Appl. No. 15/492,802.
Notice of Allowance dated Mar. 19, 2019 in U.S. Appl. No. 15/613,344.
Response to Office Action filed Mar. 27, 2019 in U.S. Appl. No. 16/124,283.
Amendment filed Apr. 10, 2019 in U.S. Appl. No. 15/266,056.
Notice of Intention to Grant dated May 10, 2019 in European Patent Application No. 17169068.8.
Final Office Action dated Jul. 29, 2019 in U.S. Appl. No. 15/226,056.
Response to Office Action filed Sep. 9, 2019 and Sep. 18, 2019 in European Patent Application No. 18205392.6.
First Examination Report dated Jun. 25, 2019 in Australian Patent Application No. 2018217270.
Response to First Examination Report filed Sep. 27, 2019 in Australian Patent Application No. 2018217270.
Response to Final Office Action filed Sep. 27, 2019 in U.S. Appl. No. 15/226,056.
Response to Office Action filed Oct. 9, 2019 in European Patent Application No. 16845150.8.
Notice of Allowance dated Nov. 12, 2019 in U.S. Appl. No. 15/226,056.
Response to European Office Action filed Dec. 4, 2019 in European Patent Application No. 19196148.1.
Notice of Allowance issued Sep. 27, 2019 in Hong Kong Patent Application No. 16114537.3.
Second Office Action issued Oct. 14, 2019 in Australian Patent Application No. 2018217270.
European Office Action issued Nov. 15, 2019 in European Patent Application No. 19196148.1.
Extended European Search Report issued Nov. 28, 2019 in European Patent Application No. 17786669.6.
First Office Action issued Dec. 5, 2019 in Japanese Patent Application No. 2018-238255, and English thereof. translation.

\* cited by examiner

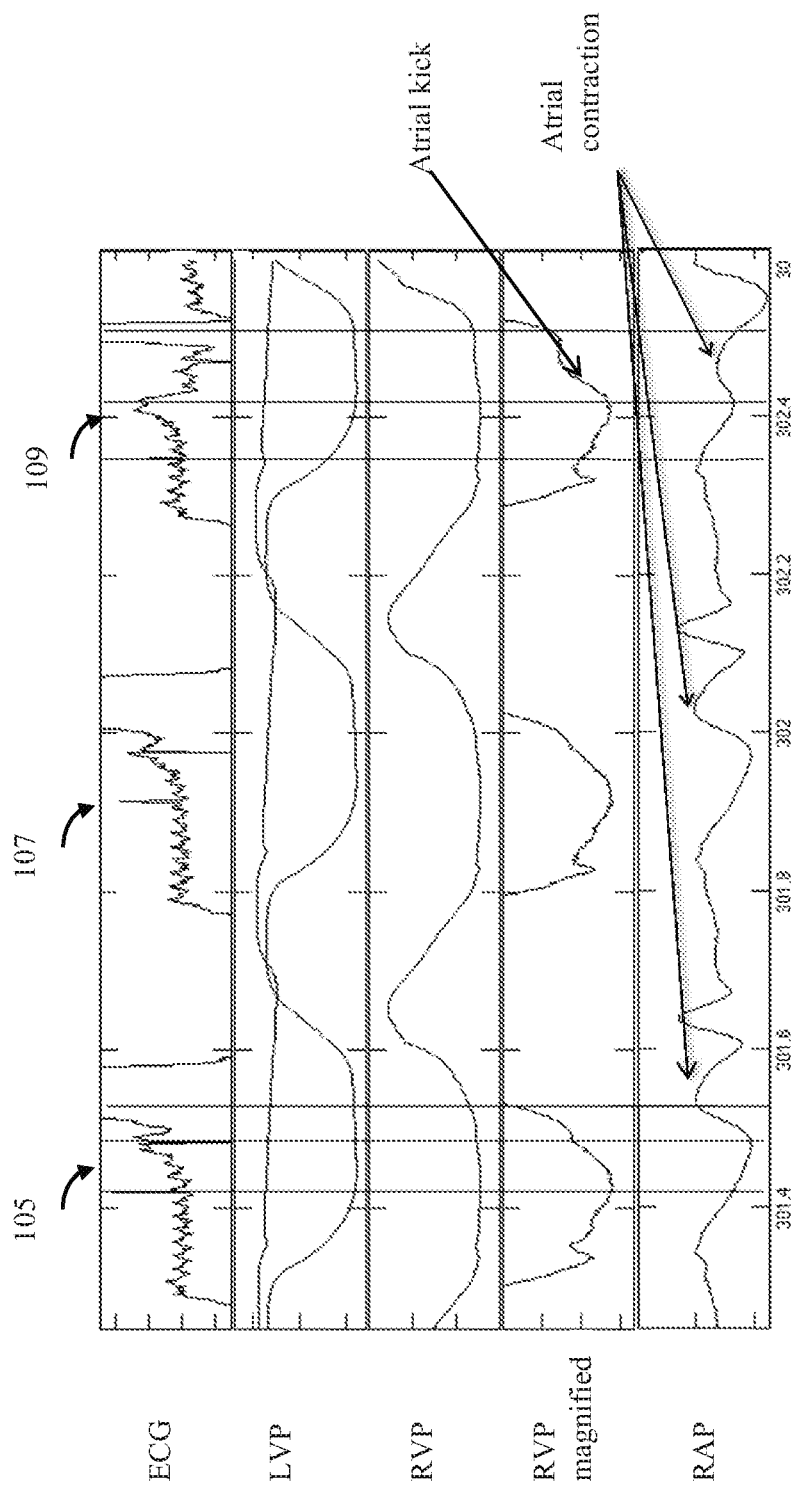

METHODS AND SYSTEMS FOR LOWERING BLOOD PRESSURE THROUGH REDUCTION OF VENTRICLE FILLING

This application is a continuation of U.S. application Ser. No. 14/652,856, filed Jun. 17, 2015, now U.S. Pat. No. 9,937,351, issued Apr. 10, 2018, which is a U.S. National Stage of International Application No. PCT/US2013/076600, filed Dec. 19, 2013, which claims priority to U.S. application Ser. No. 13/826,215, filed Mar. 14, 2013, now U.S. Pat. No. 9,008,769, issued Apr. 14, 2015, and to U.S. Provisional Application No. 61/740,977, filed Dec. 21, 2012, all of which are herein incorporated by reference in their entirety.

BACKGROUND OF THE INVENTION

1. Field of the Invention

Embodiments of the present invention relate to the field of treating hypertension through controlling cardiac filling. Specific embodiments include application of focal, electrical stimulation to the heart.

2. Description of Related Art

Variations in blood pressure are known to occur normally, due for example to increased activity (which normally elevates blood pressure) or significant blood loss (which tends to cause a reduction in blood pressure). Blood pressure is however normally maintained within a limited range due for example to the body's baroreflex, whereby elevated or decreased blood pressure affects cardiac function and the characteristics of the cardiovascular system by a feedback loop. Such feedback control is mediated by the nervous system as well as by the endocrine system (e.g., by natriuretic peptide). In hypertensive individuals, while baroreflex does function, blood pressure is maintained at an elevated level.

Hypertension, or high blood pressure (e.g., blood pressure of 140/90 mmHg or higher), is a serious health problem affecting many people. For example, approximately 74.5 million people aged 20 years and older and living in the United States have high blood pressure. Hypertension may lead to such life-threatening conditions as stroke, heart attack, and/or congestive heart failure. Approximately 44.1% of people with high blood pressure and under current treatment have satisfactory control of their hypertension. Correspondingly, 55.9% of the same people have poor control. Traditionally, treatment for hypertension has included medication and lifestyle changes. These two types of treatment are not effective for all patients. Additionally, side effects may prevent certain patients from taking medication. Accordingly, there remains a need for additional techniques for lowering blood pressure.

SUMMARY OF THE INVENTION

Methods and devices for reducing blood pressure are disclosed. Some embodiments treat hypertension mechanically instead of or in addition to treating hypertension pharmaceutically. In some embodiments, an electrical stimulator, such as a pacemaker or other type of device having a pulse generator, may be used to stimulate a patient's heart to reduce blood pressure. When the heart is stimulated in a consistent way to reduce blood pressure, the cardiovascular system may adapt to the stimulation over time and revert to a higher blood pressure. Therefore, in some embodiments, the stimulation pattern may be configured to be able to modulate the baroreflex such that the adaptation response of the cardiovascular system is reduced or even prevented.

In some embodiments, an electrical stimulator may be used to stimulate a patient's heart to cause at least a portion of an atrial contraction to occur while the atrioventricular valve is closed. Such an atrial contraction may deposit less blood into the corresponding ventricle than when the atrioventricular valve is opened during an atrial contraction.

Some embodiments may use artificial valves in treating hypertension. In some medical conditions, where one or more of the atrioventricular (AV) valves malfunctions, the valve(s) may be replaced by implantation of artificial (prosthetic) valve(s). These artificial valves may be normally configured to passively open and close, as do natural valves, as a function of pressure differences between the atria and ventricles. Passive artificial valves are normally classified in three types based on their mechanical structure: caged ball valves, tilting disc valves, and bi-leaflet valves. As an alternative, some embodiments may use an active artificial valve that is configured to actively open and close.

In one aspect, an embodiment provides a system for reducing blood pressure in a patient having a pretreatment blood pressure. The system may comprise at least one stimulation electrode for stimulating at least one chamber of a heart of a patient with a stimulating pulse. The system may comprise at least one controller configured to execute a stimulation pattern of stimulating pulses to at least a chamber of the heart. The stimulation pattern may include a first stimulation setting and a second stimulation setting different from the first stimulation setting. At least one of the first stimulation setting and the second stimulation setting may be configured to reduce or prevent atrial kick.

In one aspect, an embodiment provides a system for reducing blood pressure. The system may comprise at least one stimulation electrode for stimulating at least one chamber of a heart of a patient. The system may include at least one controller configured to execute a stimulation pattern comprising multiple stimulation pulses. At least one stimulation pulse of the multiple stimulation pulses may have a first stimulation setting configured to reduce atrial kick in at least one ventricle. At least one stimulation pulse of the multiple stimulation pulses may have a second stimulation setting configured to reduce the baroreflex response to the reduction in atrial kick such that the increase in blood pressure values occurring between stimulation pulses is limited to a predetermined value or range of values.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one of an atrium and a ventricle. The device may comprise a processor circuit coupled to the stimulation circuit and optionally also to a sensing circuit.

In some embodiments, the device processor circuit may be configured to operate in an operating mode in which the device controls the AV delay, which, as used herein, may be taken to mean a delay occurring in a single heartbeat between ventricle excitation and/or contraction and atrial excitation and/or contraction. In addition, as used herein, the AV delay in a system or method may be taken to mean, within one heartbeat, a time delay between delivery of at least one excitatory stimulus to a ventricle and one of: the sensing of an onset of atrial excitation; the timing of an anticipated onset of atrial excitation; and the delivery of at least one excitatory stimulus to the atrium.

This AV delay may be set by delivering at least one stimulation pulse to both of at least one atrium and at least one ventricle. Optionally this stimulation is performed at a rate that is higher than the natural activity of the heart. Such rate may, for example, be set using at least one sensing electrode to sense the natural activity in the heart (e.g., in the right atrium) and adjusting the stimulation pulse delivery rate accordingly.

Optionally, when ventricular excitation is timed to commence before the delivery of one or more stimulation pulses to the atria, the delivery of stimulation pulses to the heart is timed such that one or more excitatory pulses are delivered to an atrium at a time that is earlier than the next anticipated natural onset of atrial excitation.

In some embodiments, the AV delay may be set by delivering at least one stimulation pulse to one or more ventricles but not to the atria. In such case, the natural activity of one or more of the atria may be sensed and the timing of ventricle excitation and/or contraction may be set to precede its natural expected timing based on the sensed atrial activity rate.

In some embodiments, the processor circuit may be configured to operate in an operating mode in which a ventricle is stimulated to cause ventricular excitation to commence between about 0 milliseconds (ms) and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. For example, the processor circuit may be configured to operate in an operating mode in which one or more excitatory pulses are delivered to a ventricle between about 0 ms and about 50 ms before a next atrial excitation is anticipated to take place. The time interval between the onset of atrial excitation and the moment that atrial excitation is sensed may be known or estimated, and used to calculate the timing of an onset of atrial excitation. For example, if it is known or estimated that atrial excitation is sensed 5 ms after the onset of atrial excitation and the ventricle is to be stimulated 20 ms before the onset of atrial excitation, then the ventricle is to be stimulated 25 ms before the next anticipated sensing of atrial excitation. In other embodiments, the processor circuit may be configured to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments, atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, the timing of the mechanical contraction in relation to electrical excitation of a chamber for a patient may be determined, for example, by sensing changes in atrial and ventricular pressures, sensing wall motion using ultrasound (e.g., echocardiography or cardiac echo), changes in impedance, or the opening and/or closing of a cardiac valve, using implanted and/or external sensors as known in the art. Examples for such sensors include pressure sensors, impedance, ultrasound sensors, and/or one or more audio sensors and/or one or more blood flow sensors.

The timing of the mechanical contraction in relation to electrical excitation of a chamber for a patient may be taken into account and the processor circuit may be configured accordingly, such that the one or more excitatory pulses are delivered to the heart in a timing that will generate a desired pattern of contraction. This may be performed in a closed loop mode, using one or more implanted sensors, and/or may be performed occasionally (e.g., on implantation of a device and/or during a checkup), for example, using an interface with an external measurement device.

The operating mode may include stimulating the ventricle to cause the ventricle to commence contraction before the onset of contraction of the at least one atrium.

The operating mode may include stimulating the ventricle to cause the ventricle to commence contraction before the end of contraction of the at least one atrium, thereby causing the AV valve to be closed during at least part of a contraction of the at least one atrium.

The operating mode may include stimulating the ventricle to cause the ventricle to commence contraction within less than 100 ms after the onset of contraction of the at least one atrium.

Optionally, care is taken to ensure that atrial contraction will commence before ventricle contraction has reached peak pressure. This is possible even in cases in which ventricular contraction will have commenced before the onset of atrial contraction, as atrial contraction is typically faster than ventricular contraction. Accordingly, one of the following settings may be selected:

a. The operating mode may include stimulating the ventricle to cause the ventricle to commence contraction at any time during atrial contraction but before the atrium reaches its maximal contraction force.
b. The operating mode may include stimulating the ventricle to cause the ventricle to commence contraction at any time during atrial contraction but after the atrium reaches its maximal contraction force.
c. The operating mode may include stimulating the ventricle at such timing that contraction would commence in both the atrium and ventricle at essentially the same time (e.g., with no more than 5 ms from one another).
d. The operating mode may include stimulating the ventricle to cause the ventricle to commence contraction at such timing that the peak of atrial contraction would occur when the ventricle is at maximal stretch, thus causing an increase in the stretch of the atrial wall.

The operating mode may include stimulating the ventricle to cause the ventricle to contract at least partially before the onset of contraction of the at least one atrium, thereby causing the AV valve to be closed during the onset of contraction of the at least one atrium.

Optionally, the processor circuit may be configured to operate in an operating mode in which one or more excitatory pulses are delivered to an atrium between about 0 ms and about 50 ms after one or more excitatory pulses are delivered to the patient's ventricle.

In another aspect, an embodiment provides a method for reducing blood pressure of a patient having a pretreatment blood pressure and a pretreatment ventricular filling volume. The method may comprise delivering a stimulation pulse from a stimulation circuit to at least one of an atrium and a ventricle, and operating a processor circuit coupled to the stimulation circuit to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. For example, the method may include delivering one or more excitatory pulses to a ventricle between about 0 ms and about 50 ms before a next atrial excitation is anticipated to take place. The time interval between the onset of atrial excitation and the moment that atrial excitation is sensed may be known and used to calculate the timing of the onset of atrial excitation. For example, if it is known or estimated that atrial excitation is sensed 5 ms after the onset of atrial excitation and the ventricle is to be stimulated 20 ms before the onset of atrial excitation, then the ventricle is to be stimulated 25 ms before the next anticipated sensing of atrial excitation. In other embodiments, the method may comprise operating a processor circuit coupled to the stimulation circuit to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the method may include delivering one or more excitatory pulses to an atrium between about 0 ms and about 50 ms after delivering one or more excitatory pulses to the patient's ventricle. In such embodiments, the pacing may be timed without relying on sensing atrial excitation. Optionally, such embodiments comprise sensing atrial excitation in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, the timing of the mechanical contraction in relation to electrical excitation of a chamber for a patient may be evaluated using, for example, ultrasound (e.g., echocardiography or cardiac echo) or other known means. The timing of the mechanical contraction in relation to electrical excitation of a chamber for a patient may be taken into account and the timing of the delivery of the one or more excitatory pulses to the heart may be selected so as to generate a desired pattern of contraction.

The operating mode may include stimulating the ventricle to cause the ventricle to contract before the onset of contraction of the at least one atrium.

The operating mode may include stimulating the ventricle to cause the ventricle to contract before the onset of contraction of the at least one atrium, thereby causing the AV valve to be closed during at least part of a contraction of the at least one atrium.

The operating mode may include stimulating the ventricle to cause the ventricle to contract before the end of contraction of the at least one atrium, thereby causing the AV valve to be closed during the onset of contraction of at least atrium.

Optionally, the method comprises delivering one or more excitatory pulses to an atrium between about 0 ms and about 50 ms after delivering one or more excitatory pulses to the patient's ventricle.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one cardiac chamber of a patient's heart. The device may comprise a processor circuit coupled to the stimulation circuit. The processor circuit may be configured to operate in an operating mode in which at least one cardiac chamber is stimulated to cause between about 40% of an atrial contraction and about 100% of an atrial contraction to occur at a time when an atrioventricular valve related to the atrium is closed, thereby reducing the ventricular filling volume from the pretreatment ventricular filling volume and reducing the patient's blood pressure from the pretreatment blood pressure. This can be achieved, for example, by causing the atrium to commence contraction about 60 ms or less before the closure of the AV valve. Optionally, this timing may be set periodically (e.g., upon implantation) based on data from an external sensor and/or as a closed loop using one or more implanted sensors.

In another aspect, an embodiment provides a device for reducing blood pressure of a patient having a pretreatment blood pressure and a pretreatment ventricular filling volume. The device may comprise a stimulation circuit configured to deliver a stimulation pulse to at least one cardiac chamber. The device may comprise a processor circuit coupled to the stimulation circuit. The processor circuit may be configured to operate in an operating mode in which at least one cardiac chamber is paced to cause about 50% to about 95% of an atrial contraction to occur during ventricular systole, thereby reducing the ventricular filling volume from the pretreatment ventricular filling volume and reducing the patient's blood pressure from the pretreatment blood pressure. This can be achieved, for example, by causing the atrium to commence contraction about 50 ms to 5 ms before commencement of ventricular contraction. Optionally, the timing of commencement of ventricular contraction may be set according to the timing of closure of an AV valve. Optionally, this timing may be set periodically (e.g., upon implantation) based on data from an external sensor and/or as a closed loop using one or more implanted sensors.

In another aspect, an embodiment provides a method, carried out with an implanted heart muscle stimulator associated with a heart of a patient, for treating a blood pressure disorder in the patient, the patient having a pretreatment blood pressure. The method may comprise stimulating a heart to cause an atrium thereof to contract while a heart valve associated with the atrium is closed such that the contraction distends the atrium, and the distending atrium results in reducing the patient's blood pressure from the pretreatment blood pressure. This can be achieved, for example, by causing the atria to contract at a time when the pressure in the ventricle is maximal so that the active force of atrial contraction will increase atrial stretch above the maximal passive stretch caused by the contraction of the associated ventricle(s). In such cases, the timing of the maximal contraction of the atria should coincide with the end of the isovolumic period or during the rapid ejection period of the ventricle. Optionally, this timing may be set periodically (e.g., upon implantation) based on data from an external sensor and/or as a closed loop using one or more implanted sensors.

In another aspect, an embodiment provides a system for reducing blood pressure. The system may comprise at least one stimulation electrode for stimulating at least one chamber of a heart of a patient with a stimulation pattern comprising at least one stimulation pulse. The system may include at least one controller configured to receive input relating to the patient's blood pressure and adjust the stimulation pattern based on said blood pressure. For example, the input may include receiving data sensed by one or more sensors (implanted or external) and/or receiving data provided by a user. For example, during implantation and/or periodic checks, a user may provide data regarding measured blood pressure. Optionally, the system includes an input port for receiving this input by wired and/or wireless communication from a measuring sensor and/or a user interface. The input may comprise data relating to blood pressure (BP) or a change in BP, which may be measured as systolic BP (SysBP), diastolic BP, mean arterial BP, and/or any other related BP parameter. For example, at least one sensor may sense the pressure or changes of pressure in one or more cardiac chambers and adjust the stimulation pattern based on the pressure or changes in pressure. In another embodiment, the sensor may sense the pressure in more than one chamber and adjust the stimulation based on the relation between the pressure waveforms of the two chambers.

The controller may be configured to adjust the stimulation pattern by performing an adjustment process that includes adjusting a parameter of a first stimulation setting of at least one of the at least one stimulation pulse.

The first stimulation setting may be configured to reduce or prevent atrial kick in at least one ventricle.

The parameter may include the adjustment of the AV delay. For example, a natural AV delay may be a range of 120 to 200 ms between the onset of atrial excitation and the onset of ventricular excitation, whether occurring naturally (i.e., without the delivery of a stimulus to the heart) or by setting the timing of the delivery of stimuli to one or more of the atrium and ventricle. Optionally, adjusting the AV delay means adjusting it from a normal AV delay (of, for example, 120 ms) to a shorter AV delay (for example, 0 to 70 ms from the onset of atrial excitation to onset of ventricular excitation; or an AV delay of 0 to −50 ms in which the ventricular excitation occurs before atrial excitation). In a preferred embodiment of the invention, a stimulation setting having an AV delay of between −50 ms to 70 ms, preferably −40 ms to 60 ms, more preferably −50 ms to 0 or 0 to 70 ms, preferably >0 to 70 ms, is chosen to reduce or prevent atrial kick.

The stimulation pattern may be configured to cause a reduction in blood pressure by at least a predetermined amount within about 3 sec from an application of electricity to the heart, and to maintain a reduction in blood pressure for a time interval of at least 1 minute. For example, a stimulation pattern may be selected and/or adjusted based on feedback relating to one or more sensed BP parameters.

The time interval may be at least 5 minutes.

The predetermined amount of blood pressure reduction may be 8 mmHg or more.

The predetermined amount of blood pressure reduction may be at least 4% of the patient's pretreatment blood pressure.

The patient's blood pressure may not exceed a predetermined average value during the time interval by more than a predetermined degree.

The predetermined degree may be a difference of about 8 mmHg or less.

The controller may be configured to execute a plurality of stimulation patterns and receive for each of the stimulation patterns a corresponding input data relating to the patient's blood pressure during the stimulation. The controller may be configured to calculate for each of the plurality of stimulation patterns at least one blood pressure variation parameter relating to the input data. The controller may be configured to adjust the stimulation pattern according to the blood pressure variation parameter.

The controller may be configured to adjust the stimulation pattern to be the one with the best blood pressure variation parameter.

The best blood pressure variation parameter may be one that displays the lowest degree of baroreflex, or the lowest degree or rate of adaptation as detailed herein The best blood pressure variation parameter may be one that displays a baroreflex or degree of adaptation within a predetermined range as detailed herein.

The at least two stimulation patterns of the plurality of stimulation patterns may each comprise at least one stimulation pulse having a stimulation setting configured to reduce or prevent atrial kick in at least one ventricle. The at least two stimulation patterns may differ one from another by the number of times or the length of time the at least one stimulation pulse is provided in sequence.

The plurality of stimulation patterns may differ by the number of times or the length of time that the system is configured to elicit a predetermined AV delay in sequence.

The at least two stimulation patterns of the plurality of stimulation patterns may differ from another by one or more stimulation settings included within each of the at least two stimulation patterns.

The plurality of stimulation patterns may include a first stimulation pattern and a second stimulation pattern executed after the first stimulation pattern. The second stimulation pattern may have at least one stimulation setting that was set based on an algorithm using blood pressure variation parameters relating to the input data of the first stimulation pattern.

The system may comprise a blood pressure sensor for providing the input data relating to the patient's blood pressure.

The blood pressure sensor may be implantable.

The blood pressure sensor and the controller may be configured to operate at least partially as a closed loop.

In another aspect, an embodiment provides a system for reducing blood pressure. The system may comprise at least one stimulation electrode for stimulating at least one chamber of a heart of a patient with a stimulation pulse. The system may comprise a controller. The controller may be configured to provide a first stimulation pattern comprising at least one stimulation setting configured to reduce or prevent atrial kick in at least one ventricle for a first time interval and to receive a first input data relating to a patient's blood pressure during said first time interval. The controller may be configured to calculate at least one blood pressure variation parameter relating to the first input data. The controller may be configured to adjust at least one parameter of a second stimulation pattern comprising a second stimulation setting configured to reduce or prevent atrial kick in at least one ventricle. The second stimulation setting may be based upon the at least one blood pressure variation parameter. The controller may be configured to provide the second stimulation pattern for a second time interval.

In another aspect, an embodiment may provide a system for reducing blood pressure. The system may comprise at least one stimulation electrode for stimulating at least one chamber of a heart of a patient with a stimulation pulse. The system may comprise at least one controller configured to execute a stimulation pattern comprising at least one stimulation setting configured to reduce or prevent atrial kick in at least one ventricle. The stimulation pattern may be selected to cause an immediate reduction in blood pressure from an initial pressure value to a reduced pressure value and to maintain a patient's average blood pressure at rest at least 8 mmHg below the initial pressure.

The reduced blood pressure value may be maintained for a time interval of at least 1 minute.

In another aspect, an embodiment provides a kit for reducing blood pressure. The kit may comprise at least one device for setting a stimulation pattern for reducing blood pressure. The device may comprise at least one stimulation electrode. The device may comprise a controller for setting an adjustable stimulation pattern and a set of instructions for adjusting the stimulation pattern based on input relating to patient blood pressure.

In another aspect, an embodiment provides a system for reducing blood pressure. The system may comprise at least one stimulation electrode for stimulating at least one chamber of a heart of a patient. The system may comprise at least one controller configured to execute a stimulation pattern comprising at least one stimulation pulse having at least one stimulation setting configured to reduce or prevent atrial kick in at least one ventricle. The at least one stimulation setting may be configured such that maximum atrial stretch is at a value that is about equal to or lower than the maximum atrial stretch of the same heart when not receiving stimulation. Atrial stretch may be measured, calculated, and/or estimated as known in the art. In some embodiments, atrial stretch determination may include measuring atrial pressure. In some embodiments, atrial stretch determination may include measuring or estimating the dimension of an atrium (e.g., diameter, size, or circumference).

The at least one stimulation setting may be configured to cause an atrium to be at maximum contraction when the AV valve is open.

The at least one stimulation setting may be configured to alter the mechanics of at least one atrial contraction such that the mechanics of the at least one atrial contraction are different from the mechanics of a previous natural atrial contraction. The mechanics of atrial contraction may be assessed using any known technique including, for example, ultrasound (e.g., echocardiography or cardiac echo).

The at least one stimulation setting may be configured to reduce the force of at least one atrial contraction. The force of atrial contraction may be reduced, for example, by temporarily generating atrial spasm or atrial flutter. One example is the delivery of a burst of rapid stimulation pulses to the atrium for a short period of predefined time. The force of atrial contraction can be calculated from sensing of atrial pressure and/or a derivative thereof such as wall motion or flow using any known means. Such sensing may be used as a feedback in a closed loop and/or occasionally (e.g., upon implantation and/or checkups).

The at least one stimulation setting may be configured to prevent at least one atrial contraction. Atrial contraction may be prevented, for example, by temporarily generating atrial spasm or atrial flutter. One example is the delivery of a burst of rapid stimulation pulses to the atrium for a short period of predefined time.

In another aspect, an embodiment provides a system for reducing blood pressure. The system may comprise at least one stimulation electrode for stimulating at least one chamber of a heart of a patient. The at least one controller may be configured to execute a stimulation pattern of stimulation pulses to the heart of a patient. The at least one controller may be configured to receive input relating to the patient's AV valve status. This input may be provided by wired or wireless communication from an implanted or external acoustic sensor or blood flow sensor and/or via a user interface. The at least one controller may be configured to adjust the at least one stimulation pattern based on said valve status.

The input relating to the patient's AV valve status may be indicative of the timing of closure of the AV valve.

The input relating to the patient's AV valve status may be provided based on a heart sound sensor.

The input relating to the patient's AV valve status may be provided based on a blood flow sensor.

The blood flow sensor may include an implanted sensor.

The blood flow sensor may include an ultrasound sensor for sensing blood flow through the AV valve.

The blood flow sensor and the controller may be configured to operate at least partially as a closed loop.

The stimulation pattern may comprise at least one stimulation pulse configured to reduce or prevent the atrial kick in at least one ventricle.

The step of adjusting the at least one stimulation pattern may include adjusting the AV delay of at least one stimulation pulse.

In another aspect, an embodiment provides a system for reducing ventricular filling volume in a patient having a pretreatment ventricular filling volume. The system may comprise a stimulation circuit configured to deliver a stimulation pulse to at least one cardiac chamber. The system may comprise at least one controller configured to execute the delivery of one or more stimulation patterns of stimulation pulses to at least one cardiac chamber. At least one of the stimulation pulses may have a first stimulation setting and at least one of the stimulation pulses may have a second stimulation setting different from the first stimulation setting. At least one of the first stimulation setting and the second stimulation setting may be configured to reduce or prevent atrial kick, thereby reducing the ventricular filling volume from the pretreatment ventricular filling volume.

The first stimulation setting and the second stimulation setting may be configured to reduce or prevent atrial kick.

The first stimulation setting may have a different AV delay than the AV delay of the second stimulation setting.

At least one of the one or more stimulation patterns may be repeated at least twice in a period of one hour.

The at least one controller may be configured to execute the one or more stimulation patterns consecutively for a time interval lasting 10 minutes or longer. The first stimulation setting may be configured to reduce or prevent atrial kick in at least one ventricle for at least 50% of the time interval.

The second stimulation setting may have a longer AV delay than the first stimulation setting.

The second stimulation setting has a longer AV delay than the first stimulation setting.

The one or more consecutive stimulation patterns may comprise at least one stimulation pulse having the first stimulation setting for at least about 85% of the time interval.

The time interval may be at least 30 minutes long.

The time interval may be at least one hour long.

The time interval may be at least 24 hours long.

The one or more consecutive stimulation patterns may comprise at least one stimulation pulse having a third stimulation setting different from the first stimulation setting and the second stimulation setting and configured to reduce or prevent atrial kick in at least one ventricle.

The one or more consecutive stimulation patterns may comprise at least one stimulation pulse having a third stimulation setting different from the first stimulation setting and the second stimulation setting and configured not to reduce or prevent atrial kick in at least one ventricle for less than about 50% of the time interval.

The one or more consecutive stimulation patterns may comprise a third stimulation configured not to reduce or prevent atrial kick in at least one ventricle for about 20% or less of the time interval.

The one or more stimulation patterns may comprise a sequence of 10-60 stimulation pulses having the first stimulation setting. The first stimulation setting may be configured to reduce or prevent atrial kick in at least one ventricle, and a sequence of 1-10 heartbeats embedded within the 10-60 stimulation pulses. The sequence of 1-10 heartbeats may have a longer AV delay than the first stimulation setting.

The sequence of 1-10 heartbeats may include at least one stimulation pulse having a first stimulation setting configured to reduce or prevent atrial kick in at least one ventricle.

The sequence of 1-10 heartbeats may include at least one stimulation pulse having a second stimulation setting.

The sequence of 1-10 heartbeats may include a natural AV delay.

At least one heartbeat of the sequence of 1-10 heartbeats may occur without stimulation.

The first stimulation setting may be configured to reduce atrial kick in at least one ventricle and the second stimulation setting may be configured to reduce the baroreflex response or adaptation to the reduction in atrial kick such that the increase in blood pressure values occurring between stimulation pulses is limited to a predetermined value.

The second stimulation setting may be configured to allow an increase in blood pressure for about 1 heartbeat to 5 heartbeats.

The stimulation pattern may include multiple stimulation pulses having the first stimulation setting.

The stimulation pattern may include multiple stimulation pulses having the second stimulation setting.

Between about 1% of the multiple stimulation pulses and 40% of the multiple stimulation pulses of the stimulation pattern may have the second stimulation setting.

The stimulation pattern may include a ratio of stimulation pulses having the first stimulation setting to the stimulation pulses having the second stimulation setting that corresponds to a ratio of time constants of a response to increase and decrease in blood pressure.

The first stimulation setting may include a first AV delay and the second stimulation setting may include a second AV delay. The first AV delay may be shorter than the second AV delay.

The stimulation pattern may include multiple stimulation pulses having the first stimulation setting.

The stimulation pattern may include multiple stimulation pulses having the second stimulation setting.

Between about 1% of the multiple stimulation pulses and 40% of the multiple stimulation pulses of the stimulation pattern may have the second stimulation setting.

The stimulation pattern may include a ratio of stimulation pulses having the first stimulation setting to the stimulation pulses having the second stimulation setting that corresponds to a ratio of time constants of the response to increase and decrease in blood pressure.

The stimulation pattern may include a ratio of about 8 to about 13 stimulation pulses having the first stimulation setting to about 2 to about 5 the stimulation pulses having the second stimulation setting.

One of the first stimulation setting and the second stimulation setting may be configured to invoke a hormonal response from the patient's body.

In another aspect, an embodiment provides a system for reducing ventricular filling volume of a patient having a pretreatment ventricular filling volume. The system may comprise a stimulation circuit configured to deliver a stimulation pulse to at least one cardiac chamber. The system may comprise at least one controller configured to execute the delivery of one or more stimulation patterns of stimulation pulses to at least one cardiac chamber. At least one of the stimulation pulses may include a setting configured to cause a ventricular excitation to commence between about 0 ms and about 70 ms after the onset of atrial excitation, thereby reducing the ventricular filling volume from the pretreatment ventricular filling volume. For example, the processor circuit may be configured to operate in an operating mode in which one or more excitatory pulses are delivered to the ventricle between about 0 ms and about 70 ms after the onset of atrial excitation in at least one atrium occurs, or between about 0 ms and about 70 ms after one or more excitatory pulses are delivered to the atrium.

In some embodiments, the timing of a sensed atrial excitation may be determined by taking into account a delay between actual onset of excitation and the sensing thereof. For example, if a sensing delay is estimated to be 20-40 ms, and stimulation pulses are to be delivered 0-70 ms after onset of atrial excitation, a system may be set to deliver pulses between 40 ms before the next anticipated sensing event to 30 ms after the next anticipated sensing event or 30 ms after the next sensing event. Likewise, if the stimulation pulses are to be delivered to the ventricle 0-50 ms before onset of atrial excitation, assuming the same 20-40 ms sensing delay, a system may be set to deliver pulses between 40 ms before the next anticipated sensing event to 90 ms before the next anticipated sensing event. Sensing delays may be due to one or more of a distance between the site of onset of excitation and a sensing electrode, the level of the electrical signal, characteristics of the sensing circuit, and the threshold set of a sensing event. The delay may include, for example, the duration of the signal propagation from the origin of excitation to the electrode location, the duration related to the frequency response of the sensing circuit, and/or the duration necessary for the signal propagation energy to reach a level detectable by a sensing circuit. The delay may be significant and can range, for example, between about 5 ms to about 100 ms. One approach for estimating the delay is to use the time difference between an AV delay measured when both atrium and ventricle are sensed and the AV delay when the atrium is paced and the ventricle is sensed. Other approaches may use calculation of the amplifier response time based on the set threshold, signal strength, and frequency content. Other approaches may include modifying the delay used with atrial sensing until the effect on blood pressure is the same as the effect obtained by pacing both atrium and ventricle with the desired AV delay.

In another aspect, a system is provided for reducing ventricular filling volume in a patient having a pretreatment ventricular filling volume. The system may include a stimulation circuit configured to deliver a stimulation pulse to at least one cardiac chamber. At least one controller may be configured to execute the delivery of one or more stimulation patterns of stimulation pulses to at least one cardiac chamber for a time interval lasting 10 minutes or longer. At least one of the stimulation pulses may have a first stimulation setting configured to reduce or prevent atrial kick in at least one ventricle for at least 5 minutes of the time interval and at least one of the stimulation pulses has a second stimulation setting different from the first stimulation setting, thereby reducing the ventricular filling volume from the pretreatment ventricular filling volume.

In another aspect, a method is provided for reducing ventricular filling in a patient having a pretreatment ventricular filling volume. The method may include a step of delivering one or more stimulation patterns of stimulation pulses to at least one cardiac chamber for a time interval lasting 10 minutes or longer. At least one of the stimulation pulses may have a first stimulation setting configured to reduce or prevent atrial kick in at least one ventricle for at least 5 minutes of the time interval and at least one of the stimulation pulses has a second stimulation setting different from the first stimulation setting.

Other systems, methods, features, and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 12 shows a right atria pressure, magnified diastolic portion of right ventricular pressure, right ventricular pressure, left ventricular pressure and at the same graph aortic pressure and an electrocardiogram of a hypertensive canine heart;

DETAILED DESCRIPTION

Figure 1:
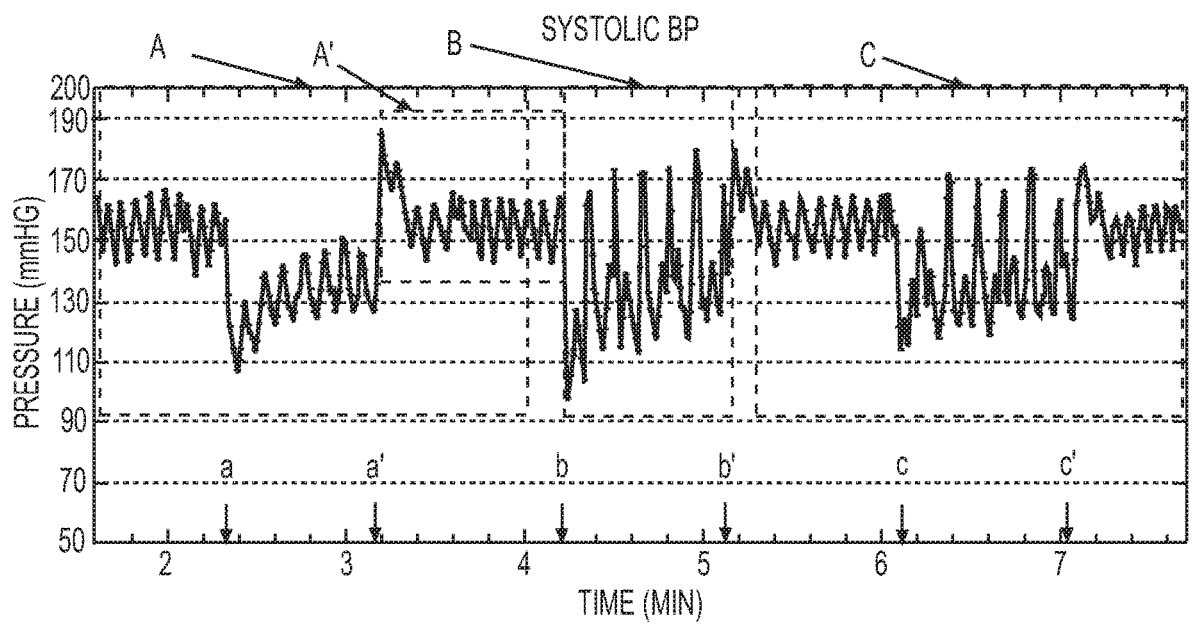
FIG. 1 shows the systolic blood pressure of a hypertensive patient receiving a stimulation signal, plotted against time.

The human heart comprises two atria and two ventricles. In a normal heart cycle, cardiac contraction begins with atrial contraction, which is followed by contraction of the ventricles.

The mechanical process of cardiac contraction is controlled by conduction of electricity in the heart. During each heartbeat, a wave of depolarization is triggered by cells in the sinoatrial node. The depolarization propagates in the atria to the atrioventricular (AV) node and then to the ventricles. In a healthy heart, atrioventricular delay (AV delay), i.e., the delay time between the onset of atrial excitation and the onset of ventricular excitation, is normally between 120 milliseconds (ms) and 200 ms. The relative timing of the atrial contraction and the ventricular contraction is affected inter alia by the relative timing of excitation of each chamber and by the time needed by the chamber to generate mechanical contraction as a result of the electrical activation (depending on size, speed of propagation, differences in myocyte properties, etc.).

Before contraction, the heart muscle is relaxed and blood flows freely into the ventricles from the atria, through a valve between them. This period can be divided into a rapid filling phase and a slow filling phase. The rapid filling phase commences just after the relaxation of the ventricle, during which blood from the venous system and the atria rapidly fills the ventricle. The rapid filling phase lasts for approximately 110 ms and is followed by the slow filling phase, which lasts until the start of the contraction of the atria. The duration of the slow filling phase depends on the heart rate. Thereafter, as an atrium contracts, pressure increases in the atrium and causes blood to flow more rapidly into the ventricle. This contribution of atrial contraction to ventricle filling is known as the "atrial kick." Atrial kick is normally responsible for about 10%-30% of ventricle filling.

A cardiac cycle begins at the onset of atrial excitation. Then, about 50-70 ms thereafter the atrium begins to contract, for a period of about 70-110 ms. Meanwhile, the electrical stimulus propagates to the ventricle and the onset of ventricle excitation occurs at an AV delay of about 120-200 ms later (the AV delay can be about 250 ms in some unhealthy individuals). As the ventricle contracts, pressure builds up within it and passively closes the valves between each of the atria and a respective ventricle (AV valves), thus stopping the flow of blood from the atrium into the ventricle and preventing backflow. During the next period of the contraction, a period known as isovolumic contraction that lasts approximately 50 ms, all ventricle valves are closed and the pressure in the ventricle rapidly rises with no significant change in volume. As ventricular pressure further increases, the valve between the ventricle and artery opens and blood flows out of the ventricle and away from the heart. The contraction is further divided into a rapid ejection period and a decreased ejection period. The rapid ejection period lasts approximately 90-110 ms, during which about ⅔ of the stroke volume is ejected. At the end of the rapid ejection period, the pressure in the ventricle and the atria reaches its peak. The rapid ejection period is followed by the decreased ejection period lasting about 130-140 ms. Thereafter, all valves close again and the ventricle relaxes in isovolumic relaxation for about 60-80 ms, during which the pressure in the ventricle drops. At this time, the valves between the ventricle and the atria reopen allowing blood to flow freely into the ventricle, and a new excitation cycle may commence.

In the present disclosure, cardiac stimulation may be used to reduce ventricular filling volume and/or blood pressure (BP). BP or a change in BP may be measured as systolic BP (SysBP), diastolic BP, mean arterial BP, BP in one or more chambers, and/or any other related BP parameter. In some embodiments, an electrical stimulator, such as a pacemaker or other type of device having a pulse generator, may be used to stimulate a patient's heart to reduce blood pressure. Electrodes electrically connected to the electrical stimulator with a wired or wireless connection may be placed adjacent a cardiac chamber. The electrical stimulator may be operated to deliver a pulse to the cardiac chamber via the electrode.

In some embodiments, stimulating the heart such that the contribution of atrial contraction to the filling of the ventricles (atrial kick) is reduced or even prevented, reduces cardiac filling at the end of diastole and consequently reduces blood pressure. For simplicity, in the following description, such stimulation will be termed "BPR (Blood Pressure Reducing) stimulation." BPR stimulation may include delivering at least one stimulation pulse to at least a chamber of a heart such that atrial kick is reduced or even prevented. Such a pulse will be referred to herein as a "BPR stimulation pulse" or "BPR pulse" herein. As used herein, a "stimulation pulse" may comprise a sequence of one or more electrical pulses delivered to one or more chambers of said heart within the timeframe of a single heartbeat. For example, in some embodiments, a stimulation pulse may comprise one or more electrical pulses delivered to one or more locations in a ventricle and/or one or more electrical pulses delivered to one or more locations in an atrium. Thus, in some embodiments, the stimulation pulse may include a first electrical pulse delivered to an atrium and a second electrical pulse delivered to the corresponding ventricle. In some embodiments a stimulation pulse may include a single pulse being delivered to a plurality of locations on one or more chambers of the heart.

A stimulation setting means one or more parameters of one or more stimulation pulses delivered in a single cardiac cycle. For example, these parameters may include one or more of: power, a time interval between electrical pulses that are included in a single stimulation pulse (e.g., AV delay), a period of delivery with respect to the natural rhythm of the heart, the length of a stimulation pulse or a portion thereof, and the site of delivery between two or more chambers and/or within a single chamber. A BPR stimulation setting, or "BPR setting," may include a setting of one or more BPR pulses.

A stimulation pattern may include a series of pulses having identical stimulation settings or a stimulation pattern may include multiple pulses each having different stimulation settings. For example, a stimulation pattern may have one or more pulses having a first setting and one or more pulses having a second setting that is different from the first setting. When stating that a stimulation pattern has a setting, it is understood that this means a stimulation pattern may include at least one stimulation pulse having that setting. It is also understood that, in some embodiments a stimulation pattern may include one or more cardiac cycles where no stimulation pulse is delivered, in which case the pulse(s) may be viewed as being delivered at zero power. A stimulation pattern may include a plurality of identical pulses or a sequence of pulses including two or more different settings. Two stimulation sequences in a pattern may differ in the order of pulses provided within a setting. Two or more stimulation sequences may optionally differ in their lengths (in time and/or number of heartbeats). In some embodiments, a stimulation pattern may include pulses having BPR settings. In some embodiments, a stimulation pattern may include pulses that do not have BPR settings.

Examples of stimulation settings that are configured to reduce or prevent atrial kick in at least one ventricle may include any of the stimulation settings disclosed herein that are configured to cause a reduction of a patient's ventricular filling volume from the pretreatment ventricular filling volume. This may be caused by having at least part of an atrial contraction take place against a closed AV valve. Some such examples include:
   a. Delivering one or more stimulation pulses to a ventricle of a patient 0-50 ms before the onset of excitation in an atrium of the patient. Optionally, this delay is set based on sensing of atrial excitation. Optionally, this includes delivering one or more stimulation pulses to the atrium 0-50 ms after the delivery of stimulation pulses to the ventricle. Optionally, this is performed at a rate that is slightly higher than the natural heart rate of the patient.
   b. Delivering one or more stimulation pulses to a ventricle of a patient 0-70 ms after the onset of excitation in an atrium of the patient. Optionally, this delay is set based on sensing of atrial excitation. Optionally, this includes delivering one or more stimulation pulses to the atrium 0-70 ms before the delivery of stimulation pulses to the ventricle. Optionally, this is performed at a rate that is slightly higher than the natural heart rate of the patient.

Some embodiments may provide a system for reducing blood pressure configured to deliver stimulation at a rate higher than the natural heart rate based on sensed natural heart rate or natural excitation. For example, the system may be configured to sense the natural excitation between delivery of stimulation pulses and if a natural activity is sensed, the system may be configured to inhibit the delivery of the stimulation pulse to the chamber. If in a given time frame the amount of sensed activations exceeds a threshold, the natural heart rate may be regarded as higher than the rate of delivery of the stimulation pulses, in which case the rate of delivery may be increased, e.g., to accommodate increased heart rate of a patient. On the other hand, if in a given time frame the amount of sensed activations is lower than a threshold (this threshold may be 0), the natural heart beat may be regarded as lower than the rate of delivery of the stimulation pulses, in which case the rate of delivery may be reduced, e.g., to avoid over excitation of a patient's heart. To achieve this effect, according to one embodiment, a system for reducing blood pressure may include a sensor for sensing an excitation rate of at least one of an atrium and a ventricle of a patient's heart, a stimulation circuit configured to deliver stimulation pulses to an atrium and a ventricle, and a processor circuit coupled to the stimulation circuit. Optionally, a sensor for sensing the excitation rate of at least one of an atrium and a ventricle may comprise an electrode for sensing atrial excitation. The processor circuit may be configured to detect the patient's heart rate based on the sensing and operate in an operating mode in which a stimulation pulse is provided to each of the at least one of an atrium and a ventricle. The stimulation pulse may be delivered at a rate that is higher than the sensed excitation rate and may be configured to stimulate the ventricle at a time between about 50 ms before and about 70 ms after stimulation of the atrium.

Reducing atrial kick may have an immediate effect on blood pressure while hormone mediated mechanisms may take a longer period. While some devices may be configured to have both an immediate and a hormone mediated effect, optionally, some of the BPR settings and/or stimulation patterns may be configured to reduce or prevent atrial kick without a significant increase in atrial stretch. For example, when the AV valve closes at a time that atrial contraction is at peak pressure or thereafter, premature closure of the valve does not increase atrial stretch. Thus, in some embodiments, a device may be configured to cause the relative timing of atrial excitation and ventricular excitation to be comparable with an AV delay that is at least 40 ms long or at least 50 ms long. Atrial stretch may be measured, calculated, and/or estimated as known in the art. In some embodiments, atrial stretch determination may include measuring atrial pressure. In some embodiments, atrial stretch determination may include measuring or estimating the dimension of an atrium (e.g., diameter, size, or circumference).

In some embodiments, atrial kick may be reduced because the BPR stimulation setting may be set such that atrial contraction of a cardiac cycle is incomplete when the AV valve is open. In some embodiments, atrial contraction may take place completely or in part against a closed AV valve. In some embodiments atrial contraction may be prevented or reduced in force.

In some embodiments, only one or more ventricles may be stimulated and the stimulation pulse may be timed to have an abnormal AV delay (e.g., 50 ms before to 120 ms after atrial excitation). In some embodiments, a BPR stimulation setting may include the delivery of at least one electrical pulse or stimulus to one or more atria. In some embodiments, this at least one atrial stimulus may cause atrial contraction. In some embodiments, the at least one atrial stimulus may interfere with atrial contraction. In some embodiments, the at least one atrial pulse may cause an atrial spasm or another type of inefficient atrial contraction.

The reduction in blood pressure resulting from BPR stimulation may be observed practically immediately upon application of the stimulation signal (e.g., within 1 or 3 seconds (sec) or within 1, 3, or 5 heartbeats) and may reach a minimal blood pressure value within less than 5 heartbeats from the beginning of stimulation.

By controlling the settings of BPR stimulation, one may control the degree to which BP is reduced. This degree is sometimes patient specific and/or related to the precise positioning of one or more stimulation and/or sensing electrodes in or on the heart.

Adaptation a. The inventors found that while stimulation is maintained, blood pressure may display an adaptation pattern wherein blood pressure increases after a time (some of which often occurs in a short time being less than 5 minutes or even less than a minute), and potentially reaches near pre-stimulation blood pressure values (possibly due at least to baroreflex) or even higher. The adaptation, at least in part, may be attributed to changes in properties of the cardiovascular system, such as increase in total peripheral resistance. The inventors further found that termination of stimulation results in a quick return of blood pressure to pre-stimulation values or even higher values, and thereafter that the heart becomes responsive to the blood pressure reducing stimulation signal at a degree similar to a heart that was not so stimulated. In addition, it was found that different stimulation patterns that comprise a plurality of BPR stimulation settings result in different blood pressure adaptation patterns.

b. Stimulation patterns may, for example, comprise at least a first stimulation setting and a second stimulation setting different from the first stimulation setting, the first stimulation setting and the second setting configured to reduce or prevent atrial kick. The stimulation pattern may even comprise more than two different stimulation settings. The second setting in some embodiments has a longer AV-delay than the first setting. The second setting in some embodiments may not be configured to reduce atrial kick.

In FIG. 1, the systolic blood pressure of a hypertensive patient receiving a stimulation signal is plotted against time. The crosses along the plotted line depict the peak systolic blood pressure for every heartbeat. During approximately the first 2 plotted minutes, no stimulation signal was delivered. As seen, the patient's initial blood pressure was on average more than 150 mmHg. The oscillations in blood pressure (about ±10 mmHg) are attributed to the breathing cycle, as known in the art.

Then, a first stimulation pattern was applied during time interval a-a', a second stimulation pattern was applied during time interval b-b', and a third stimulation pattern was applied during time interval c-c'. In between the stimulation patterns and after the third stimulation pattern, the heart was not stimulated.

Figure 2:
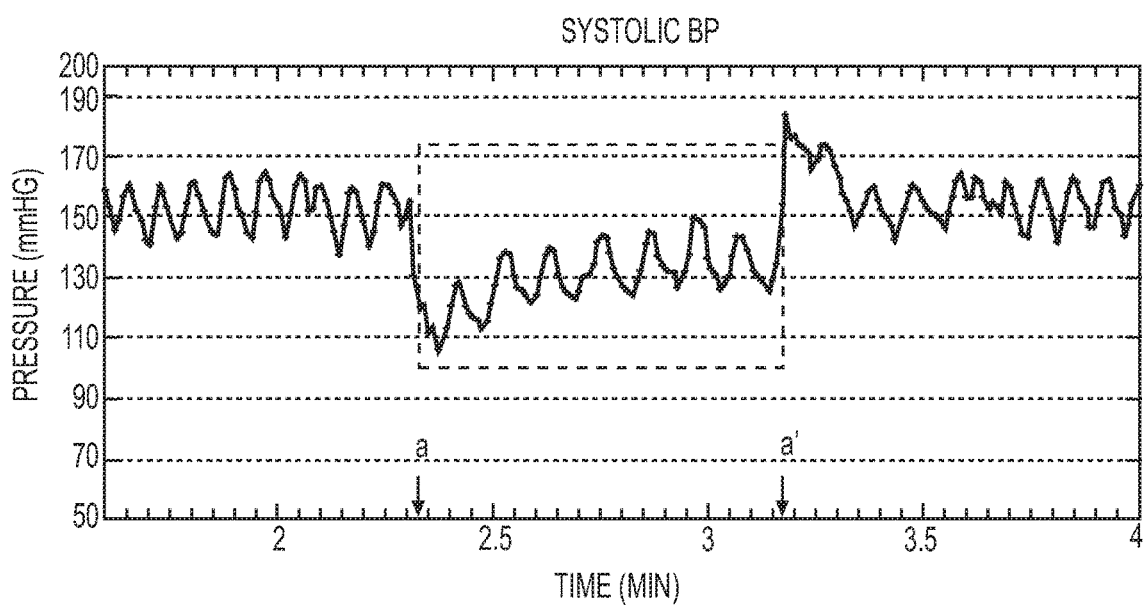
FIG. 2 shows an enlarged view of the portion of FIG. 1 marked by dashed rectangle A.

Attention is now drawn to FIG. 2, depicting an enlarged portion of FIG. 1 marked by dashed rectangle A. During the time marked by the dashed rectangle in FIG. 2, which corresponds with the time interval a-a' in FIG. 1, a stimulation commenced and was delivered to the patient's right atrium and right ventricle, such that the atrium received a BPR stimulation signal (pulse) 2 ms before the ventricle. Stimulation ended at the time marked a' in FIGS. 1 and 2. During the time interval a-a', the patient's systolic pressure initially reduced to a minimal value below 110 mmHg, and then gradually increased to intermediate values, between the initial blood pressure and the achieved minimum. At point a', stimulation stopped and an immediate overshoot in blood pressure was observed, to a value above 170 mmHg. Within about a dozen heartbeats, the blood pressure returned to its initial range.

The changes in blood pressure presented in FIGS. 1 and 2 represent, at least in part, the cardiovascular system's response to changes in blood pressure, known as the baroreflex. The baroreflex acts to restore blood pressure to its pre-stimulation level by changing cardiovascular characteristics (e.g., peripheral resistance and/or cardiac contractility). It may be assumed that the reduction in blood pressure that resulted from the reduction in ventricular filling provoked a baroreflex response directed towards restoration of the pre-stimulation blood pressure. The effect of the baroreflex on the cardiovascular system is evident, for example, at point a' in FIG. 2. At that point, the stimulation that affected ventricular filling was withdrawn and blood pressure immediately exceeded pre-stimulation blood pressure. This may be taken to indicate baroreflex changes to the cardiovascular system (e.g., peripheral resistance increased and contractility increased). At point a', where stimulation stopped and blood pressure peaked, the baroreflex responded to the increase in blood pressure by again changing one or more characteristics of the cardiovascular system, this time in order to lower the blood pressure to the level before the change. As can be clearly seen, the response of the baroreflex feedback to increase and decrease in blood pressure is asymmetric in that the response to an increase in blood pressure is much faster than the response to a decrease in blood pressure. Some embodiments may make use of this asymmetry of the baroreflex to reduce or even prevent adaptation of the reduction in blood pressure due to reduced filling, for example, by controlling a stimulation pattern accordingly, as detailed herein.

Figure 3A:
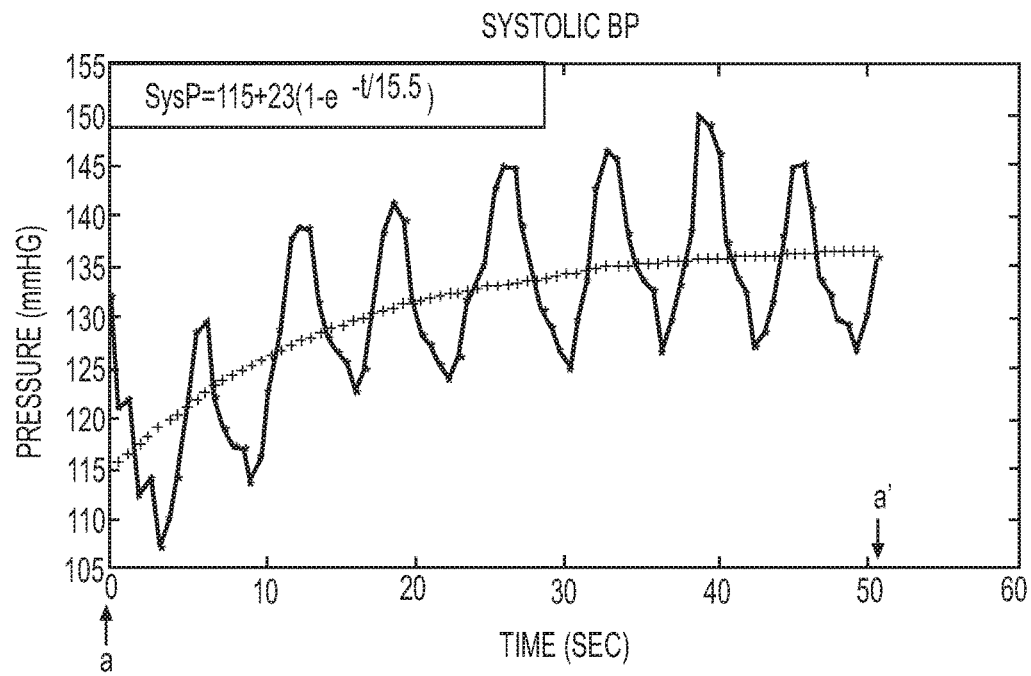
FIG. 3A depicts an enlarged view of the portion of FIG. 2 between time point a and point a'.

FIG. 3A depicts an enlarged view of the curve of FIG. 1 between time point a and point a'. In FIG. 3A, an exponential function was fitted to the plotted curve showing an adaptation response, the function describing a relation between time and SysBP, and having the following formula:

$$P = Pi + DP(1 - e^{-t/k})$$

Where P (in mmHg) denotes the systolic blood pressure, Pi (mmHg) is a first average reduced blood pressure upon commencement of BPR stimulation, DP (mmHg) is a constant representing the amount of increase in pressure after the initial decline to a new steady state level, k (sec) is a response time constant, e is the mathematical constant, being the base of the natural logarithm, and t (sec) is time.

In FIG. 3A, the matching function was as follows:

$$P = 115 + 23(1 - e^{-t/15.5})$$

Where Pi was found to be 115 mmHg, DP was 23 mmHg, and k was 15.5 sec.

Figure 3B:
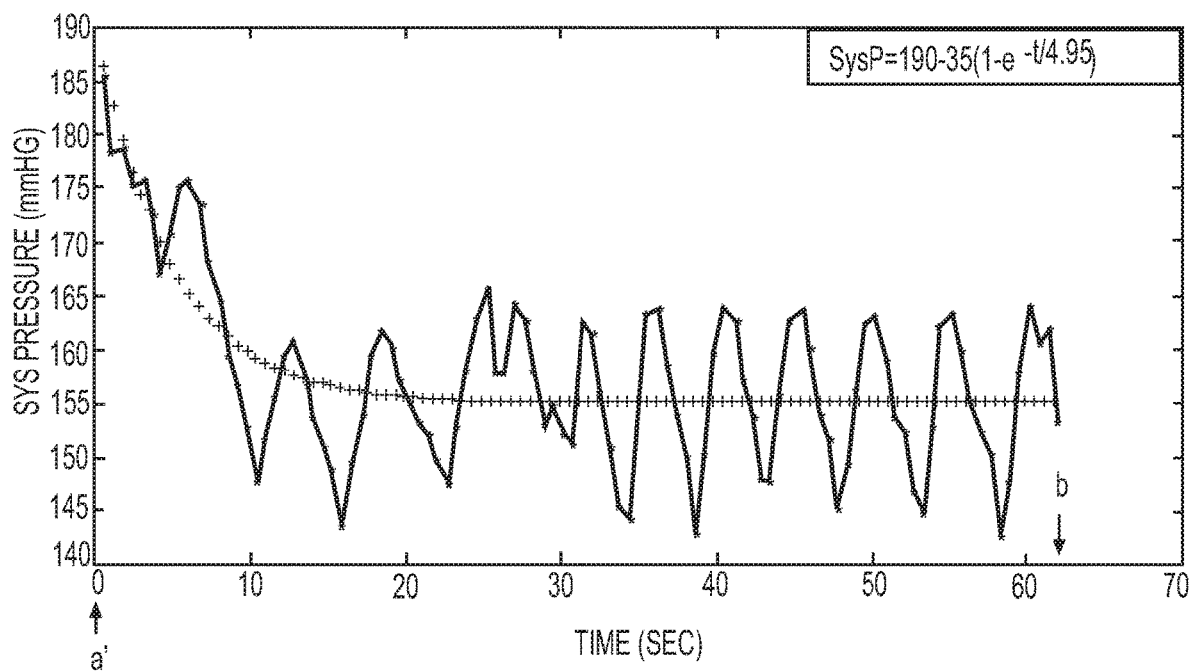
FIG. 3B depicts an enlarged view of the portion of FIG. 1 marked by dashed rectangle A'.

FIG. 3B depicts an enlarged view of the portion of FIG. 1 marked by dashed rectangle A'. In FIG. 3B, an exponential function was fitted to the plotted curve showing an adaptation response to the termination of the delivery of BPR stimulation. As seen, this response, which manifested in a reduction of blood pressure, was faster than the response to BPR stimulation.

In FIG. 3B, the matching function was as follows:

$$P = 190 - 35(1 - e^{-t/4.946})$$

Where Pi was found to be 190 mmHg, DP was −35 mmHg, and k was 4.946 sec.

As mentioned above, the baroreflex response to a reduction in blood pressure is much slower than the baroreflex response to an increase in blood pressure. This is indicated by the ratio of the aforementioned time constants k (about 15 sec to about 5 sec) with a much faster response to the increase in blood pressure. This asymmetry in the speed of the baroreflex response may provide means to design a stimulation pattern that generates an average reduction in blood pressure and reduction or even prevention of adaptation. For example, in a preferred embodiment, a stimulation pattern may alternate between two stimulation settings in a way that the weighted response favors the changes in the cardiovascular system invoked by increase in blood pressure. In this embodiment, the heart may be stimulated using a stimulation pattern having two stimulation settings: the first setting designed to reduce ventricular filling and thereby reduce blood pressure, and the second setting designed to have normal ventricular filling, or at least a higher ventricular filling, than that of the first setting. This stimulation pattern may comprise pulses having the first setting (BPR) delivered for a period of time that is shorter than the time constant of the baroreflex response to the decrease in blood pressure. In such case, adaptation may begin to manifest and blood pressure may increase from the reduced level, but may not reach its pre-stimulation level. The stimulation pattern may also comprise pulses having the second setting (e.g., natural AV delay) delivered for a period of time that is longer than the time constant of the baroreflex response to increase in blood pressure. In this case, full advantage may be taken of the baroreflex caused reduction in blood pressure, and blood pressure may even return to its level before the stimulation pattern switched to this second setting. The weighted response of the baroreflex in such a pattern may reduce or prevent adaptation while the average pressure may be lower than a pre-stimulation level. The relation between the time constants and the period of time allotted to the delivery of pulses having different settings may determine the level of baroreflex response that takes effect during the whole stimulation pattern. If, for a given stimulation setting, the period of delivery is selected to be shorter than the time constant of response, the baroreflex may not be able to change the cardiovascular system back to a pre-stimulation level, and if the period selected is greater than the time constant, the baroreflex effect may be more pronounced.

Figure 4:
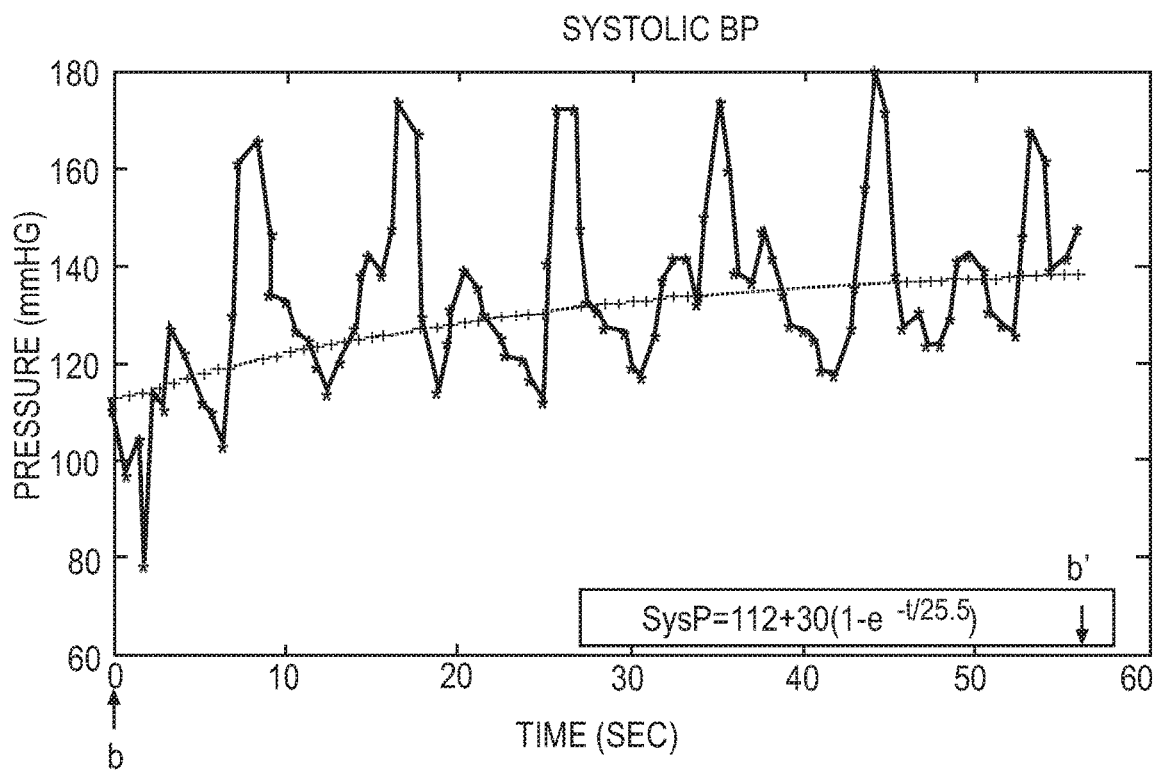
FIG. 4 depicts an enlarged view of the portion of FIG. 1 marked by dashed rectangle B.

As seen in FIG. 1, at the interval between points b and b', a second stimulation pattern was delivered. FIG. 4 depicts an enlarged version of this portion of FIG. 1 (marked by dashed rectangle B in FIG. 1). In the second stimulation pattern, a sequence of 12 BPR pulses were delivered to both an atrium and a corresponding ventricle at an AV delay of 2 ms, followed by 3 heartbeats at which only atrial stimulation and no ventricular stimulation was artificially delivered. During these last 3 heartbeats, ventricular excitation occurred by the natural conductance through the AV node that resulted in an AV delay of ~180 ms. This second stimulation pattern was repeated for the duration of the shown time interval. In FIG. 4, the exponential function matching the curve was found to be the following:

$$P = 112 + 30(1 - e^{-t/25.5})$$

As seen, Pi and also DP were comparable to the corresponding values of the first stimulation pattern (a-a' in FIG. 3A). However, k of the second pattern was nearly twice the time constant of the first stimulation pattern. In this time interval, adaptation occurred at a slower rate than in FIG. 3A, but blood pressure spiked more than it did in FIG. 3A when the pattern switched between the stimulation pulses. This result demonstrates that the use of a stimulation pattern having alternating stimulation settings reduced adaptation.

Figure 5A:
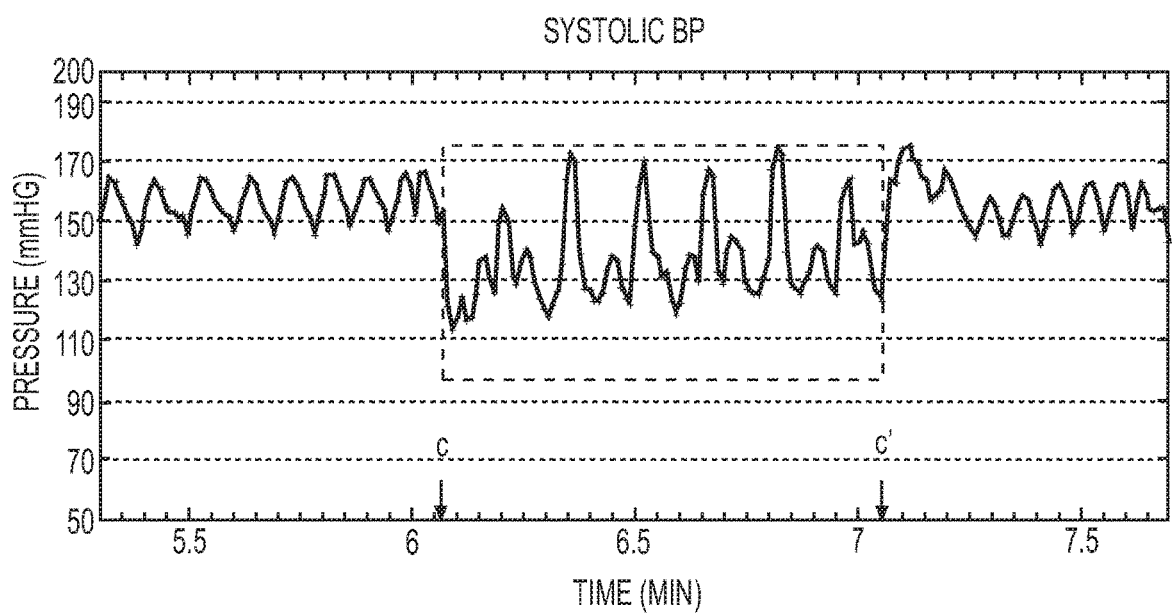
FIG. 5A depicts an enlarged view of the portion of FIG. 1 marked by dashed rectangle C.

A third stimulation pattern was delivered as well, as seen in FIG. 1, between points c and c'. FIG. 5A depicts an enlarged view of the portion of FIG. 1 marked by dashed rectangle C, which includes the portion of the curve between point c and point c'. In the third stimulation pattern, a sequence of 12 BPR pulses was delivered at an AV delay of 2 ms, followed by 3 BPR pulses, each with a 120 ms AV delay. This was repeated for the duration of the shown time interval.

Figure 5B:
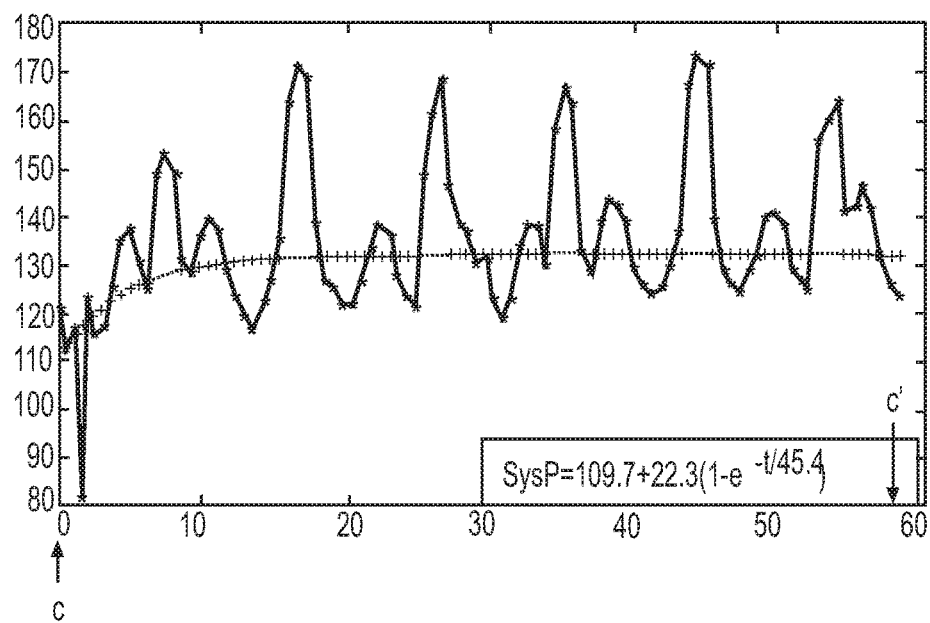
FIG. 5B depicts an enlarged view of the portion of FIG. 5A between time point c and point c'.

The portion of the curve of FIG. 5A that is marked by a dashed rectangle is plotted in FIG. 5B. In FIG. 5B, an exponential function was fitted to the plotted curve showing an adaptation response to the delivery of the stimulation pattern of 12 BPR pulses delivered at an AV delay of 2 ms followed by 3 BPR pulses, each with a 120 ms AV delay.

In FIG. 5B, the matching function was as follows:

$$P = 109.7 + 22.3(1 - e^{-t/45.4})$$

Where Pi was found to be 109.7 mmHg, DP was 22.3 mmHg, and k was 45.4 sec. As seen, while the initial reduction in blood pressure was comparable with the one shown in FIG. 3A (Pi=115 or 109.5), the adaptation time constant (k) was much higher (45.4 sec v. 15.5 sec), meaning that a low blood pressure was maintained for a period of time that is about 3 times greater than in FIG. 3A.

Figure 6:
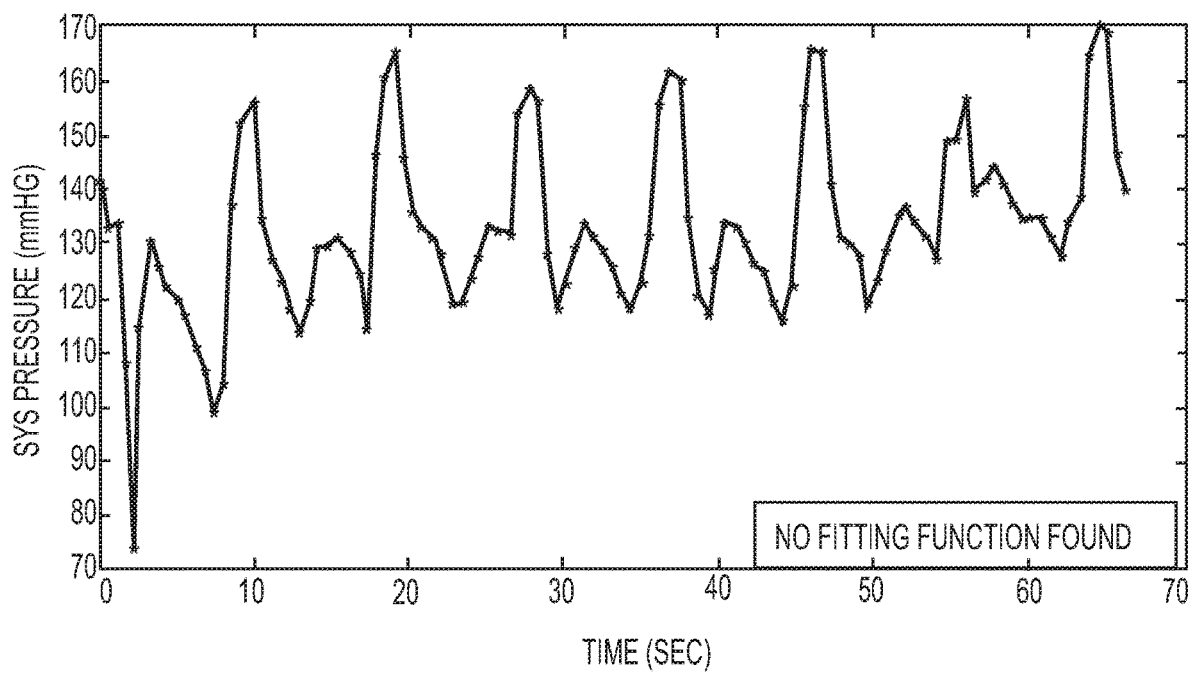
FIG. 6 shows the systolic blood pressure of a hypertensive patient receiving a stimulation signal, plotted against time.

Attention is now drawn to FIG. 6, wherein a hypertensive patient's heart was stimulated at a stimulation pattern having a sequence of 12 BPR pulses delivered at an AV delay of 2 ms, followed by 3 BPR pulses, each with an 80 ms AV delay.

As seen, in this case, the adaptation rate was very low and almost undetectable at the allotted time interval. An exponential formula could not be matched, suggesting that the adaption was extremely slow or did not exist.

Figure 7:
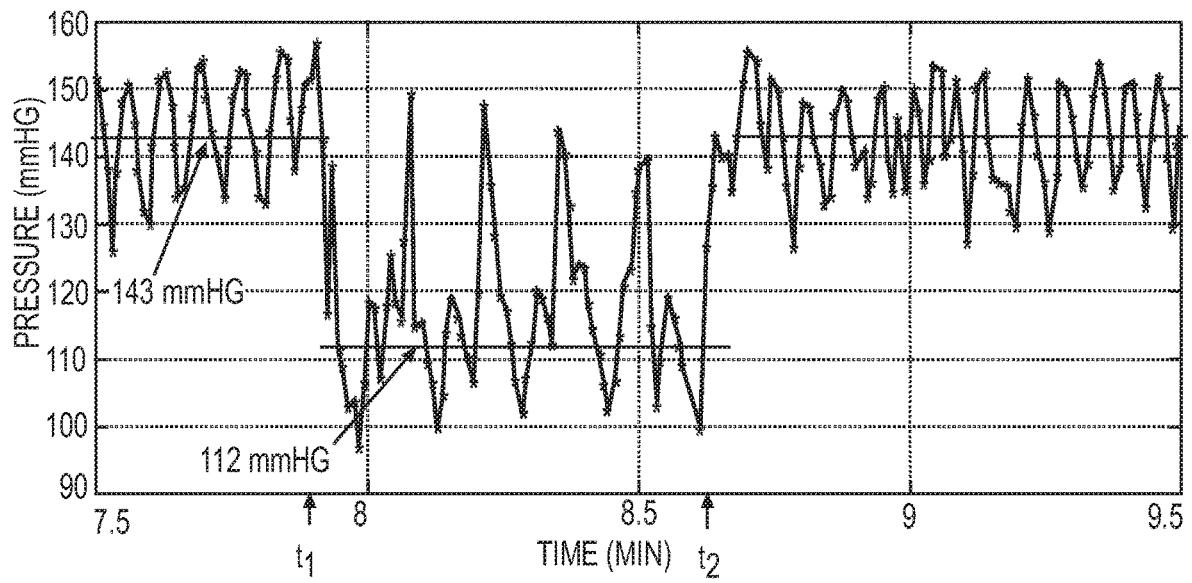
FIG. 7 shows the systolic blood pressure of a hypertensive patient receiving a stimulation signal, plotted against time.

In FIG. 7, a hypertensive patient's heart was stimulated with a stimulation pattern having a sequence of 12 BPR pulses delivered at an AV delay of 2 ms, followed by 3 BPR pulses, each with a 40 ms AV delay. Stimulation commenced at point $t_1$ and ended at point $t_2$. There was no measured adaptation response and the fitting curve was in fact linear and had a fixed average reduced blood pressure of about 112 mmHg, which is about 31 mmHg lower than the blood pressure immediately before and after the time interval $t_1$-$t_2$.

As apparent from the different stimulation patterns shown before, a stimulation pattern comprising at least one BPR stimulation can be set to at least approach one or more targets. For example, in some embodiments, a stimulation pattern may be set to cause an initial reduction in blood pressure (systolic and/or diastolic) that will exceed a predetermined threshold or will be within a predetermined range. In a more specific embodiment, the blood pressure may be reduced by at least a given percentage or by at least a given measure (e.g., 10 or 20 mmHg or even 30 mmHg) or the blood pressure may be reduced to be within a given range (e.g., between 90 and 130 mmHg SysBP) or below a given target (e.g., 130 mmHg SysBP or less). In some embodiments, a target may include maintaining a reduced blood pressure for a prolonged period of time within a reduced average range. For example, the pretreatment blood pressure may be reduced to a predetermined average blood pressure for a period of time or a number of heartbeats. In another embodiment, the target may include causing a given percentage of heartbeats to be at the reduced range/threshold. In some embodiments, the target may include reducing blood pressure while also reducing the level of spikes between stimulation pulses. For example, a stimulation pattern may be used to lower the blood pressure to a constant blood pressure for a predetermined interval of time. In some embodiments, a stimulation pattern may be used to lower the blood pressure without significantly influencing the cardiac output. For example, applying intermittent BPR pulses may allow pulses with a higher (or even full) atrial kick to occur between BPR pulses. The pulses with a higher (or even full) atrial kick may prevent the BPR pulses from significantly lowering the cardiac output. In another embodiment, reducing adaptation that relates to lowering total peripheral resistance together with reduction of blood pressure (afterload) can positively affect cardiac output by affecting flow via the blood system. In yet another embodiment, pacing at a higher rate than the patient's natural rhythm may avoid a negative effect on cardiac output that might be associated with lower stroke volume.

In some embodiments, a time constant of the change in blood pressure of a given pattern may be calculated and the stimulation pattern may be set to have one or more BPR stimulation parameters for an amount of time or number of heartbeats that are set as a certain percentage of the calculated time constant. For example, in FIGS. 3A and 3B, k was measured to be about 15 sec for the rate of increase in blood pressure during delivery of a BPR pulses and about 4.9 sec for the rate of adaptation to the termination of the delivery of BPR pulses. In some embodiments, it may be desired to prevent blood pressure from increasing beyond a given value, in which case, the period of delivery of the BPR pulses may be selected to be significantly smaller than k (e.g., 30% to 60% of k). In this embodiment, the interval may be selected to be less than 15 sec. Such an interval may include about 6-10 sec or about 8-14 heartbeats where the heart rate is about 80 heartbeats per minute.

Optionally, it is desired to take advantage of the adaptation response to the withdrawal of BPR pulses. In such case, a greater portion of k might be applied. For example, based on FIG. 3B, a period of 3-5 heartbeats may be selected (where k is about 4.9 sec). Thus, for example, based on FIGS. 3A and 3B, the inventors applied the stimulation pattern of FIG. 4.

The stimulation pattern may be set, for example, to be the best of a plurality of stimulation patterns (i.e., the one closest to a set target parameter) and/or it may be selected as the first tested stimulation pattern that conformed to a set target.

Embodiments of Methods for Setting and/or Selecting a Stimulation Pattern

Figure 8:
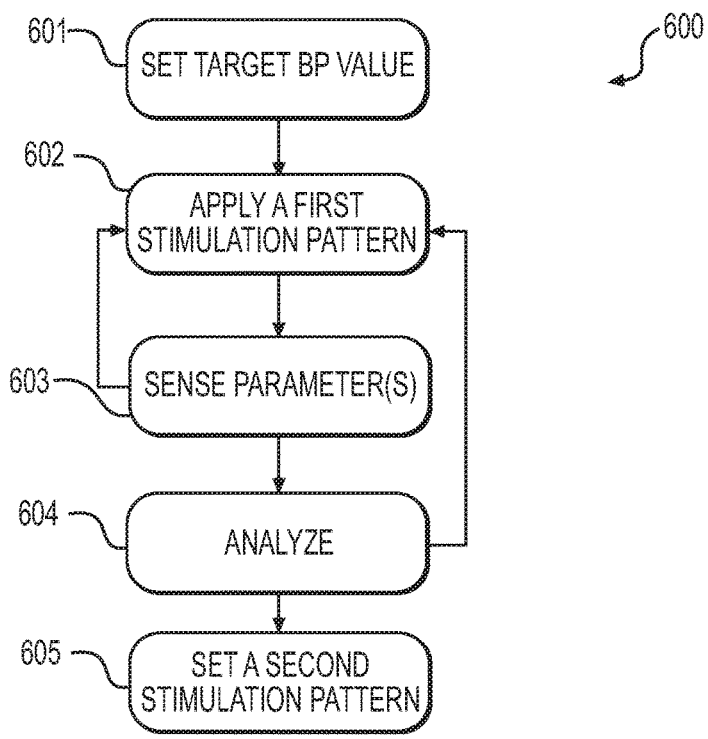
FIG. 8 is a flow chart showing an exemplary method for setting and/or selecting a stimulation pattern.

An exemplary method 600 for setting and/or selecting a stimulation pattern is schematically depicted in FIG. 8. Method 600 may be performed during implantation of a device for performing BPR stimulation and/or periodically to adjust the device operation parameters and/or continuously during operation. Method 600 may be performed by system 700, described below. Accordingly, system 700 may be configured to perform any step of method 600. Similarly, method 600 may include any steps system 700 is configured to perform. For example, method 600 may include any of the functions discussed below with respect to system 700. Additionally, method 600 may be performed by device 50, described below. Method 600 may include any steps device 50 is configured to perform.

Throughout the present disclosure, the terms "first," "second," and "third" are not meant to always imply an order of events. In some cases, these terms are used to distinguish individual events from one another without regard for order.

In some embodiments, step 601 may include setting a target blood pressure value. This target may be an absolute blood pressure value (e.g., a target blood pressure range, a target threshold of spike value, and/or number or portion of spikes in a given timeframe), a relative value (e.g., as compared with the pre-treatment blood pressure of the patient or as a comparison between a plurality of tested stimulation patterns), or both. The target blood pressure value may be a blood pressure value (e.g., measured in mmHg) and/or a value associated with a formula calculated to match a blood pressure measurement of a stimulation pattern, etc. This target blood pressure value may be set before, during, and/or after the other method steps and it may also be amended, for example, if not reached by any tested simulation pattern.

Step 602 may include delivery of one or more stimulation patterns, including a first stimulation pattern, to one or more chambers of a patient's heart. The first stimulation pattern may be a generic stimulation pattern or the first stimulation pattern may already be selected to match a given patient (e.g., when implanting a replacement device). The first stimulation pattern may include at least one stimulation setting configured to reduce or prevent atrial kick in at least one ventricle for a first time interval.

Step 603 may include sensing one or more parameters before, during, and/or after the delivery of each of one or more stimulation patterns (step 602). The sensed parameter(s) may comprise a blood pressure value or a blood pressure related parameter (e.g., a change in blood pressure). In some embodiments, the sensed parameter(s) may comprise information relating to the timing and/or extent of closure and/or opening of an AV valve. In some embodiments, the sensed parameter(s) may comprise information relating to the timing and/or rate of blood flow between an atrium and ventricle of the heart. In some embodiments, the sensed parameter(s) may include sensing pressure within a heart chamber (e.g., an atria and/or ventricle). In some embodiments, sensing of a patient's AV valve status, or position, (i.e., opened or closed) may include sensing of heart sounds, for example, using audio sensors. In some embodiments, sensing of a patient's AV valve status may include Doppler sensing and/or imaging of cardiac movement. In some embodiments, the patient's AV valve status may be sensed by a blood flow sensor.

In some embodiments, sensing of blood flow may be performed by one or more implanted sensors in one or more cardiac chambers. For example, one or more pressure sensors may be placed in the right ventricle. In some embodiments, a plurality of pressure sensors may be placed in a plurality of chambers. Optionally, measurements of a plurality of sensors may be combined. Optionally, pressure changes, trends of pressure changes, and/or pressure change patterns may be used to provide information relating to blood flow. In some embodiments, comparing relative changes between two or more sensors in different chambers may be used.

When a stimulation pattern is delivered to a heart (step 602), the one or more parameters may be measured at least once during delivery of the stimulation pattern or at a plurality of times or even continuously. Each stimulation pattern may be delivered more than once.

Step 604 may include analyzing the sensed parameter(s). In some embodiments, once at least one stimulation pattern is delivered and corresponding parameter(s) are sensed, analysis may be performed (604). In embodiments in which multiple parameters are sensed, step 604 may include the following: comparing sensed parameter values to a target; comparing sensed parameters between two or more stimulation patterns; comparing calculated values (e.g., the k constant) relating to two or more stimulation patterns; and comparing additional sensed parameters between two or more stimulation patterns. In some embodiments, this last function may be performed to determine and select which stimulation pattern yields a higher ejection fraction, stroke volume, cardiac output, and/or a lower battery use.

Step 605 may include setting a pacing (stimulation) pattern. When more than one parameter is sensed, the stimulation pattern used in step 605 may be selected based on the plurality of parameters, a plurality of target values, and/or a plurality of target ranges.

In some embodiments, the steps shown in FIG. 8 may be performed in the order shown by the arrows in FIG. 8. In other embodiments, the steps may be performed in another order. For example, step 602 may be performed before setting a target blood pressure value in accordance with step 601. In some embodiments, a stimulation pattern may be set to be performed indefinitely. In some embodiments, a stimulation pattern may be set to be performed for a predetermined period of time. For example, in some embodiments, the stimulation pattern set during step 605 may be performed for a predetermined period of time and then step 602, step 603, and step 604 may be repeated to determine how another stimulation pattern affects the patient's blood pressure. Then, based on the analysis performed in step 604, step 605 may also be repeated.

In some embodiments, method 600 may include a step of adjusting a first stimulation pattern, thus making the first stimulation pattern into a second stimulation pattern. In some embodiments, step 605 of setting a stimulation pattern may include adjusting a stimulation pattern. For example, step 605 may include adjusting a parameter of a first stimulation setting, e.g., the time interval from step 602. In another embodiment, step 605 may include adjusting a parameter of a first stimulation setting configured to reduce or prevent the atrial kick in at least one ventricle. In some embodiments, step 605 may include adjusting first stimulation pattern to be a second stimulation pattern configured to cause a reduction in blood pressure by at least a predetermined amount. In some embodiments, the predetermined amount may include, for example, about 8 mmHg to about 30 mmHg. In some embodiments, the predetermined amount may be at least 4% of a patient's pretreatment blood pressure. For example, the predetermined amount may be about 4% of a patient's pretreatment blood pressure to about 30% of a patient's pretreatment blood pressure.

In some embodiments, step 605 may include adjusting the stimulation pattern to be a stimulation pattern configured to cause an immediate reduction in blood pressure by at least a predetermined amount. For example, in some embodiments, step 605 may include adjusting the stimulation pattern to be a stimulation pattern configured to cause a reduction in blood pressure by at least a predetermined amount within about 3 sec from an application of electricity to the heart. In some embodiments, step 605 may include adjusting the stimulation pattern to be a stimulation pattern configured to cause a reduction in blood pressure by at least a predetermined amount within at least 5 heartbeats of the applied electricity. In some embodiments, the reduction in blood pressure resulting from a stimulation pattern set during step 605 may occur within 1-3 sec of the application of electricity to the heart or within 1, 3, or 5 heartbeats of the application of electricity to the heart.

In some embodiments, the reduction in blood pressure resulting from a stimulation pattern set during step 605 may be such that a patient's average blood pressure at rest is at least 8 mmHg below the patient's initial blood pressure at rest. In some embodiments, the reduction in blood pressure resulting from a stimulation pattern set during step 605 may be maintained for at least 1 minute. In some embodiments, the reduction in blood pressure resulting from a stimulation pattern set during step 605 may be maintained for at least 5 minutes. In some embodiments, the blood pressure may reach a minimal blood pressure value within less than 5 heartbeats from the beginning of stimulation. For example, step 605 may include adjusting a first stimulation pattern to be a second stimulation pattern configured to cause a reduction in blood pressure. In some embodiments, step 605 may include adjusting the first stimulation pattern to a second stimulation pattern configured to cause a reduction in blood pressure for a predetermined time interval. For example, the predetermined time interval may include at least 1 minute or at least 5 minutes.

In some embodiments, the second stimulation pattern may be configured to maintain a blood pressure that does not exceed a predetermined average value during the predetermined interval by more than a predetermined degree. For example, the predetermined degree may be a difference of about 20 mmHg or less. In some embodiments, the predetermined degree may be a difference of about 1 mmHg to about 8 mmHg.

In some embodiments, the second stimulation pattern may include a second stimulation setting configured to reduce or prevent the atrial kick in at least one ventricle. The second stimulation setting may be based upon at least one blood pressure variation parameter calculated from an input data sensed during application of the first stimulation pattern.

In some embodiments, the second stimulation pattern may be configured to reduce or limit the magnitude of spikes in blood pressure between stimulation pulses. In some embodiments, the spikes in blood pressure between stimulation pulses may be reduced to a percentage of a baseline blood pressure value. For example, the second stimulation pattern may be configured to prevent more than an 80% increase in blood pressure between pulses. In other words, the second stimulation pattern may be configured to prevent the blood pressure from spiking more than about 80% between pulses. In some embodiments, the second stimulation pattern may be configured to prevent more than a 40% increase in blood pressure between pulses. In some embodiments, the second stimulation pattern may be configured to prevent a blood pressure spike of more than about 10 mmHg to about 30 mmHg between pulses. For example, in some embodiments, the second stimulation pattern may be configured to prevent a blood pressure spike of more than 20 mmHg between pulses.

In some embodiments, the second stimulation pattern may comprise multiple stimulation pulses. At least one stimulation pulse of the multiple stimulation pulses may have a first stimulation setting configured to reduce atrial kick in at least one ventricle. At least one stimulation pulse of the multiple stimulation pulses may have a second stimulation setting configured to reduce the baroreflex response to the reduction in atrial kick such that the increase in blood pressure values occurring between stimulation pulses is limited to a predetermined value. In some embodiments, the second stimulation setting may be configured to increase blood pressure for about 1 heartbeat to 5 heartbeats to invoke negation of the baroreflex response. In some embodiments, the second stimulation pattern may include multiple stimulation pulses having the first stimulation setting and multiple stimulation pulses having the second stimulation setting. In such embodiments, between about 1% of the multiple stimulation pulses and 40% of the multiple stimulation pulses of the stimulation pattern may have the second stimulation setting. In some embodiments, the second stimulation pattern may include multiple stimulation pulses having the first stimulation setting and multiple stimulation pulses having the second stimulation setting. In such embodiments, between about 1% of the multiple stimulation pulses and 40% of the multiple stimulation pulses of the stimulation pattern may have the second stimulation setting. In some embodiments, the stimulation pattern may include a ratio of stimulation pulses having the first setting to the stimulation pulses having the second setting based on a ratio of time constants of the response to increase and decrease in blood pressure. For example, the ratio of stimulation pulses having the first setting to the stimulation pulses having the second setting may be based on a ratio of the time constants of the changes in blood pressure resulting from each of the first setting and the second setting. In some embodiments, the first stimulation setting may include a first AV delay and the second stimulation setting may include a second AV delay, the first AV delay being shorter than the second AV delay. In some embodiments, the second stimulation pattern may include multiple stimulation pulses having the first stimulation setting and one or more stimulation pulses having the second stimulation setting. In some embodiments, the second stimulation pattern may include a ratio of about 8 stimulation pulses to about 13 stimulation pulses having the first setting to about 2 stimulation pulses to about 5 stimulation pulses having the second setting. In some embodiments, the second stimulation pattern may include at least one stimulation pulse having a stimulation setting configured to invoke a hormonal response from the patient's body. In some embodiments, the first stimulation pattern may include at least one stimulation pulse having a stimulation setting configured not to invoke a hormonal response from the patient's body. In some embodiments, the second stimulation pattern may be applied before the first stimulation pattern in a given sequence of stimulation patterns.

In some embodiments, method 600 may include alternating between two or more stimulation patterns. For example, method 600 may include alternating between two to ten stimulation patterns.

In some embodiments, the blood pressure sensor and the controller may be configured to operate at least partially as a closed loop.

In some embodiments, method 600 may include the controller executing a plurality of stimulation patterns and receiving for each of the stimulation patterns a corresponding input data relating to a patient's blood pressure during the stimulation. The plurality of stimulation patterns may include at least two stimulation patterns each comprising at least one stimulation pulse having a stimulation setting configured to reduce or prevent the atrial kick in at least one ventricle. The at least two stimulation patterns may differ from one another by the number of times or the length of time the at least one stimulation pulse is provided in sequence. The at least two stimulation patterns may differ from one another by the number of times or the length of time a predetermined AV delay occurs in sequence. In some embodiments, the stimulation setting may be identical in each of the at least two stimulation patterns. In some embodiments, the stimulation setting may include an identical AV delay for each of the at least two stimulation patterns. In some embodiments, the at least two stimulation patterns may differ from one another by one or more stimulation settings included within each of the at least two stimulation patterns.

In some embodiments, method 600 may include the controller calculating for each of the plurality of stimulation patterns at least one blood pressure variation parameter relating to the input data. Method 600 may include the controller adjusting the stimulation pattern according to the blood pressure variation parameter. In some embodiments, method 600 may include the controller adjusting the stimulation pattern to be the stimulation pattern with the best blood pressure variation parameter. For example, the best blood pressure variation parameter may include the blood pressure variation parameter that displays the lowest degree of baroreflex. The best blood pressure variation parameter may include the blood pressure variation parameter that displays a baroreflex within a predetermined range.

In some embodiments, the second stimulation pattern may include at least one stimulation pulse having a stimulation setting configured to invoke a hormonal response from the patient's body, while in some embodiments, the first stimulation pattern may include at least one stimulation pulse having a stimulation setting configured not to invoke a hormonal response from the patient's body.

In some embodiments, the plurality of stimulation patterns may include a first stimulation pattern and a second stimulation pattern executed after the first stimulation pattern. The second stimulation pattern may have at least one stimulation setting that was set based on an algorithm using blood pressure variation parameters relating to the input data of the first stimulation pattern.

Embodiments of Systems for Reducing Blood Pressure

Figure 9:
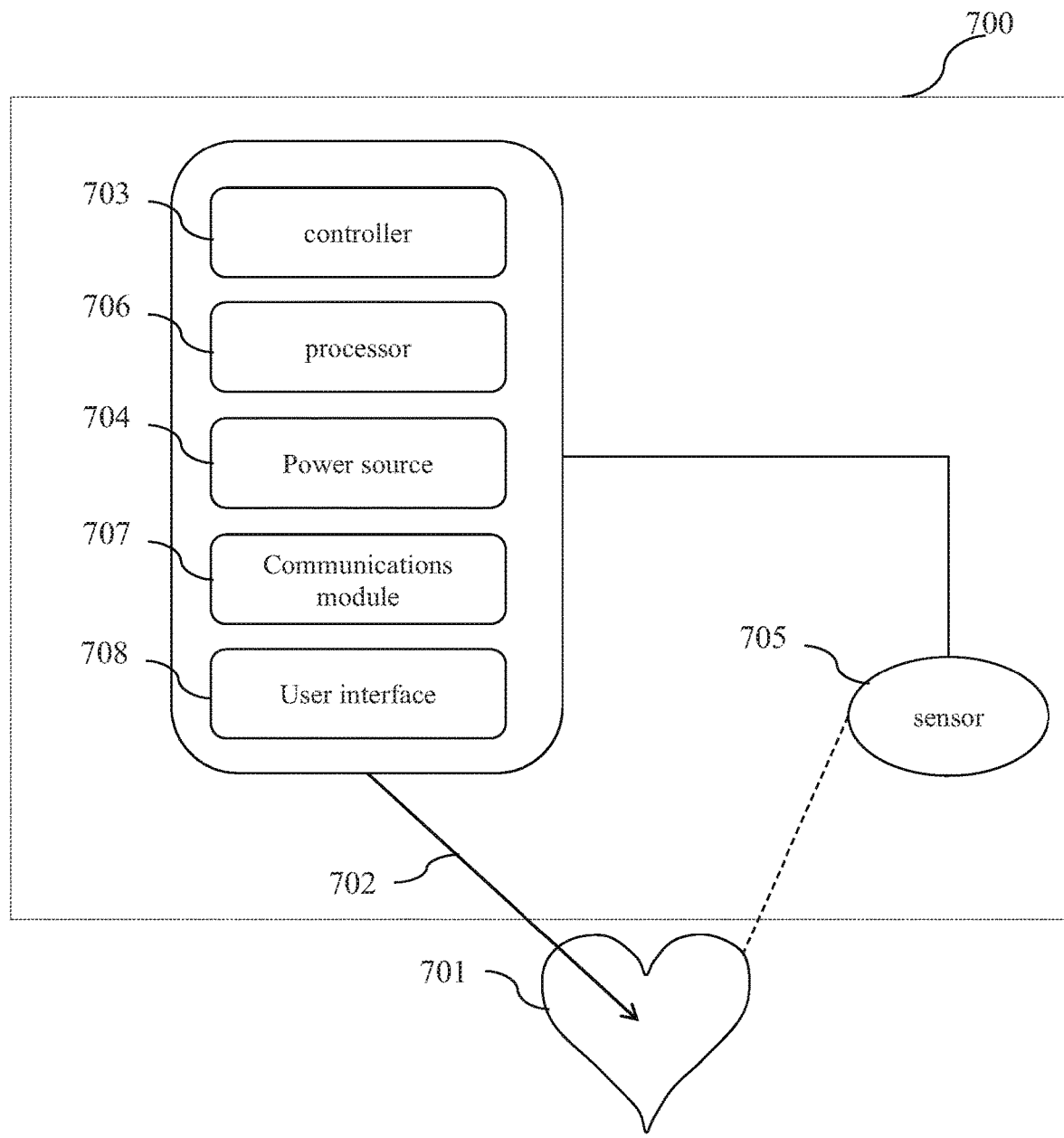
FIG. 9 is a schematic diagram illustrating an exemplary system for reducing blood pressure.

FIG. 9 schematically depicts an exemplary system 700 for reducing blood pressure according to some embodiments. System 700 may be a device or may comprise a plurality of devices, optionally associated by wire or wireless communication. The device(s) may have multiple components disposed inside a housing and/or connected to the housing electronically and/or by wires. As shown in FIG. 9, a heart 701 is connected to a system 700 by one or more stimulation electrodes 702. The stimulation electrode(s) may be configured to stimulate at least one chamber of a heart of a patient with a stimulation pulse. In some embodiments, multiple electrode(s) 702 may each be positioned in a different chamber of the heart. For example, one electrode may be positioned in an atrium and another electrode may be positioned in a ventricle. In some embodiments, multiple electrodes 702 may be positioned in a single chamber. For example, two electrodes may be positioned in an atrium and/or two electrodes may be positioned in a ventricle. In some embodiments, one electrode may be positioned in first chamber and multiple electrodes may be positioned in a second chamber.

In the present embodiment, the electrode(s) 702 may include typical cardiac pacemaker leads, such as the Medtronic Capsure® pacing leads. These leads are used to connect the heart 701 to system 700. The pacing leads may be constructed with an industry standard IS-1 BI connector at one end (reference standard ISO 5148-3:2013), electrodes at the other end, and an insulated conductor system between them. In some embodiments, the IS-1 BI connector is constructed using stainless steel for the two electrode contacts and silicone as an insulating material. Some embodiments may use polyurethane as an insulating material.

Stimulation of one or more cardiac chambers may be accomplished by placing a voltage between the two electrodes of the atrial or ventricular cardiac pacing leads described above. The stimulation circuit uses a network of transistors (e.g., MOSFETS) to charge a capacitor to a specific programmable voltage, such as 2.0V, and then control its connection to the electrodes for a fixed period of programmable time, such as 0.5 ms. The same network may also manage a discharge of any residual charge that may be accumulated on the electrodes after stimulation is complete. The same network may control the type of stimulation applied, such as bipolar (between the two electrodes) or unipolar (between one electrode and the stimulator housing).

One or more electrodes may be placed in contact with one or both ventricles and/or one or both atria, as known in the art. Such electrodes may be used to sense and/or deliver stimuli to the respective cardiac chamber(s). For example, pacing electrodes can be introduced to both ventricles, with one electrode implanted into the right ventricle and an additional electrode placed on the left ventricle through the coronary sinus, and with the system 700 including means to generate biventricular stimulation of both ventricles in order to reduce dyssynchrony caused by ventricular stimulation.

System 700 may include a controller 703. System 700 may be an electrical stimulator including a power source 704 (e.g., a battery as known in the art of electrical stimulators). Controller 703 and/or electrode(s) 702 may draw power from power source 704.

Optionally, the electrical stimulator of system 700 is constructed of a hermetically sealed housing and a header. The housing may be constructed of titanium or any other biocompatible material, and may contain a power source 704, electronics, and a telemetry coil or communication module 707 for communication with an external device. The power source 704 may be an implantable grade, hermetically sealed, primary battery. The battery chemistry may be lithium-iodine. Other embodiments may use larger or smaller batteries. Other embodiments may use rechargeable batteries such as Li-ion rechargeable batteries. The electronics in some embodiments may be constructed of standard off-the-shelf electronics (e.g., transistors and diodes) and/or custom electronics (e.g., ASIC).

In order to detect the onset of atrial excitation and/or ventricular excitation, one or more sensing electrodes may be implanted at or near a site of interest in the heart. These sensing electrodes may be the same electrodes used for delivering pulses to the heart or dedicated sensing electrodes. The electrical activity may be band-pass filtered to remove unwanted noise and may conform to an international standard for cardiac pacemakers (reference EN45502-2-1: 2003), with programmable cutoff frequencies. An electrical circuit may be used to amplify the electrical signals generated by a propagating activation of the cardiac chamber and to determine the onset of activation once the electrical signals fulfill specified criteria, for example, crossing of a predefined threshold. The signal may, for example, be amplified, with programmable gains, and then passed to a comparator for threshold detection, with programmable detection thresholds in steps of 0.2 mV (atrial) and 0.4 mV (ventricle). These means of detecting excitation may introduce a delay between the actual onset of activation in the chamber and its detection, since the detecting electrodes may be away from the origin of excitation and the time it takes for the signal to fulfill the detection criteria might not be negligible and may be in the range of 5 to 50 ms or even more. In such cases, the timing of the onset of excitation may be estimated based on the timing of a sensed excitation, and the delivery of stimulation pulses would be calculated to compensate for this delay.

Optionally, the controller 703 interfaces with an accelerometer to measure patient activity level. This patient activity level may be used to adjust the pacing rate and/or BPR settings and/or the stimulation pattern based upon the patient's needs. Activity level may also be used to control a desired level of effect on blood pressure. For example, reduction in blood pressure may be reduced at high levels of activity to enable better performance when an increase in blood pressure is required. Optionally, when a patient is inactive (e.g., when sleeping) blood pressure may reduce naturally, in which case pacing may be adjusted in order to avoid reducing blood pressure below a desired threshold. Activity level may also be used to adjust settings based on baroreflex to allow better response when needed. The sensor may be, for example, a piezoelectric sensor. Other embodiments may use a MEMS-based accelerometer sensor. Other embodiments may use a minute ventilation sensor, optionally in combination with an accelerometer.

Controller 703 may be configured to deliver electricity to the heart 701 via one or more electrodes 702. Controller 703 may be configured to execute a stimulation pattern of stimulation pulses according to any embodiment of this disclosure. In some embodiments, the stimulation pulses may be delivered to at least a ventricle of the heart. In some embodiments, the stimulation pattern may include a first stimulation setting and a second stimulation setting different from the first stimulation setting, with the first stimulation setting and the second setting configured to reduce or prevent the atrial kick. In some embodiments, the first stimulation setting has a different AV delay than the second stimulation setting. In some embodiments, the first stimulation setting and/or the second stimulation setting may be configured such that maximum atrial stretch is at a value that is about equal to or lower than the maximum atrial stretch of the same heart when not receiving stimulation. In some embodiments, the first stimulation setting and/or second stimulation setting are configured to cause an atrium to be at maximum force when the AV valve is open. In some embodiments, the first stimulation setting and/or second stimulation setting are configured to alter the mechanics of at least one atrial contraction such that the mechanics of the at least one atrial contraction are different from the mechanics of a previous natural atrial contraction. In some embodiments, the first stimulation setting and/or second stimulation setting are configured to reduce the force of at least one atrial contraction. In some embodiments, the first stimulation setting and/or second stimulation setting are configured to prevent at least one atrial contraction.

In some embodiments, the controller 703 may be configured to deliver a variety of different AV delays. The controller 703 may be configured to sense when the atrial contraction or excitation occurs (as described herein) and then deliver ventricular stimulation a fixed interval after that or before a future anticipated atrial excitation or contraction. The interval may be programmable. The controller 703 may also be configured to stimulate the atrium and then deliver ventricular stimulation at a fixed interval after that, which may also be programmable. The programmable interval may, for example, be changed between 2 ms and 70 ms to accommodate a desired therapeutic effect or even provide a negative AV delay of up to −50 ms.

In some embodiments, controller 703 may be configured to repeat a stimulation pattern multiple times. For example, controller 703 may repeat a stimulation pattern twice. In another embodiment, controller 703 may be configured to repeat a stimulation pattern at least twice in a period of an hour. The stimulation pattern repeated by controller 703 may include any type of stimulation pattern. For example, the stimulation pattern may include a stimulation setting configured to reduce or prevent the atrial kick in at least one ventricle. In another embodiment, the stimulation pattern may include two different stimulation settings each configured to reduce or prevent the atrial kick in at least one ventricle. These two stimulation settings may differ by one or more parameters, for example, by AV delay.

In some embodiments, controller 703 may be configured to execute one or more consecutive stimulation patterns for a predetermined time interval. For example, in some embodiments, the time interval may be 10 minutes or longer. In another embodiment, the time interval may be 30 minutes or longer, one hour or longer, or 24 hours or longer. In some embodiments, the time interval may be a period of months, such as one month to one year. In some embodiments, the time interval may be longer than one year. In some embodiments, the one or more consecutive stimulation patterns may include a first stimulation setting configured to reduce or prevent the atrial kick in at least one ventricle for a portion of the time interval. For example, the one or more consecutive stimulation patterns may include a first stimulation setting configured to reduce or prevent the atrial kick in at least one ventricle for about 50% of a time interval to about 100% of the time interval. In another embodiment, the one or more consecutive stimulation patterns may include a first stimulation setting configured to reduce or prevent the atrial kick in at least one ventricle for about 50% of a time interval to about 85% of the time interval. In some embodiments, the one or more consecutive stimulation patterns may include a second stimulation setting having a longer AV delay than the first stimulation setting for at least one heartbeat during the time interval. In some embodiments, the one or more consecutive stimulation patterns may include a second stimulation setting and/or a third stimulation setting. The second stimulation setting and/or third stimulation setting may each be different from the first stimulation setting. In some embodiments, the second stimulation setting and/or third stimulation setting may each be configured to reduce or prevent the atrial kick in at least one ventricle. In some embodiments, the second stimulation setting and/or third stimulation setting may each be configured not to reduce or prevent the atrial kick in at least one ventricle. In some embodiments, the second stimulation setting and/or third stimulation setting may include about 0% of a time interval to about 50% of the time interval. In some embodiments, the second stimulation setting and/or third stimulation setting may include about 0% of a time interval to about 30% of the time interval. In some embodiments, the second stimulation setting and/or third stimulation setting may include about 0% of a time interval to about 20% of the time interval. In some embodiments, the second stimulation setting and/or third stimulation setting may include about 5% of a time interval to about 20% of the time interval.

In some embodiments, controller 703 may be configured to execute one or more consecutive stimulation patterns including a sequence of 10-60 stimulation pulses having a first stimulation setting configured to reduce or prevent the atrial kick in at least one ventricle. In some embodiments, controller 703 may be configured to execute one or more consecutive stimulation patterns including a sequence of 1-10 heartbeats embedded within the 10-60 stimulation pulses and the sequence of 1-10 heartbeats may have a longer AV delay than the first stimulation setting. For example, the 10-60 stimulation pulses may include 5 stimulation pulses having the first stimulation setting, followed by one heartbeat having a longer AV delay than the first stimulation setting, followed by 50 stimulation pulses having the first stimulation setting. The sequence of 1-10 heartbeats may include at least one stimulation pulse having a first stimulation setting configured to reduce or prevent the atrial kick in at least one ventricle. The sequence of 1-10 heartbeats may include a natural AV delay. The sequence of 1-10 heartbeats may occur without stimulation.

System 700 may further comprise one or more sensors 705. In some embodiments, such sensor(s) 705 may include one or more sensing electrode(s) for sensing electrical activity of the heart. In some embodiments, one or more sensing electrode(s) may include one or more stimulation electrode(s) 702. In some embodiments, sensor(s) 705 may include one or more blood pressure sensors (implantable and/or external). In some embodiments, one or more sensors 705 may include one or more pressure sensors implanted in the heart (e.g., in the atria and/or ventricle). In some embodiments, sensor(s) 705 may include one or more blood flow sensors (implantable and/or external). For example, one or more sensors 705 may include ultrasound sensing of blood flow through the AV valve. In some embodiments, sensor(s) 705 may include one or more sensors configured to monitor the timing of closure of the AV valve. One or more of these sensors may be configured to operate as a closed loop with the controller.

Information from sensor(s) 705 may be provided to controller 703 by any form of communication, including wired communication and/or wireless communication. Optionally, system 700 may comprise one or more communication modules 707 for receiving and/or transmitting information between system components and/or to devices that are external to the system. In some embodiments, controller 703 may be configured to receive input data relating to the patient's blood pressure. For example, the input data relating to the patient's blood pressure may include data indicative of BP measured at one or more points in time or of a variation in BP (e.g. a degree of change and/or a rate of change or a function describing the change of blood pressure over time) and/or statistical data relating to BP or variation in BP, maximum and/or minimum BP values Optionally, system 700 may comprise one or more user interfaces 708 for providing information and/or for allowing input of information. Providing information may include, for example, a display of operational information relating to the system and/or data that was recorded by the system and/or received by the system during operation. This may include sensed parameter(s) and/or a relation between sensed parameter(s) and operational information (such as stimulation pattern settings and/or relative timing between delivery of a given pace and sensed information).

Optionally, user interface 708 may be comprised of a commercially available laptop computer (e.g., Windows®-based computer) running a software application. The software application may serve to generate orders to be delivered to an interface that is, in turn, connected to a hand-held wand that contains a telemetry circuit for communication with the implantable stimulator. The orders sent to the wand may be used to set stimulation parameters and/or to retrieve device diagnostics, device data, cardiac data, and real-time cardiac sensing. The interface also allows for connection of a 3-lead ECG and this data is displayed on the laptop computer screen by the software application. Other embodiments may not include the 3-lead ECG circuitry or may include 12-lead ECG circuitry. Other embodiments may incorporate the functionality of the wand, interface, and laptop computer into a dedicated piece of hardware that performs all three functions. Other embodiments may also add printing capability to the user interface 708.

In some embodiments, interface(s) 708 may be configured such that a user (e.g., medical practitioner) may provide a set of control instructions to the system (e.g., target values and/or ranges and/or other limitations or instructions). Optionally, interface(s) 708 may allow a user to input data from one or more sensors 705 (e.g., the results of a manual blood pressure measurement and/or results of an ultrasound monitor).

Optionally, the one or more user interfaces 708 may allow a user to select a stimulation pattern (for example, from a set of stimulation patterns stored in system 700) or impose constraints on the setting and/or selecting of a stimulation pattern.

Optionally, system 700 may comprise one or more processors 706. Processor(s) may be configured to process sensed parameters from sensor(s) 705 and/or input data from user interface(s) 708 to select a stimulation pattern for delivery by system 700. Optionally, processor(s) 706 may be configured to analyze sensed parameters and extract information and/or formula constants to be used in the selection and/or evaluation of stimulation patterns.

One or more components of system 700 or portions of such components may be implanted in the patient, while some components of system 700 or portions of such components may be external to the patient. When some components (or component parts) are implanted and others are not, communication between the components may take place by wired and/or wireless means, essentially as known in the art. For example, some or all functions of both controller 703 and/or processor 706 may be performed outside the body. Having some components of system 700 external to the patient's body may assist in reducing the size and/or energy requirements of an implanted device, and/or in the enhancement of the system's computation capabilities.

System 700 may include additional functions relating to control of heart function and overall cardiovascular system performance. For example, system 700 may include one or more algorithms and/or electrodes to enable biventricular pacing or resynchronization therapy to reduce dyssynchrony that may be caused by ventricular stimulation. In some embodiments, system 700 may include one or more algorithms to compensate for a possible reduction in cardiac output. Such an algorithm that may change heart rate in order to increase cardiac output or implement other methods known in the art for controlling cardiac output. In some embodiments, system 700 may include rate response algorithms to affect changes in heart rate as a response to certain circumstances. For example, system 700 may include rate response algorithms to affect changes in heart rate as a response to changes in level of exercise, ventilation activity, and/or oxygen consumption. In some embodiments, system 700 may include a sensor that detects activity and the algorithm may turn off stimulation while a patient is exercising such that a patient's blood pressure is not reduced. In some embodiments, system 700 may include a real-time clock. Such a clock may be used to control the timing of the stimulation. For example, system 700 may include an algorithm that turns stimulation on and off depending upon the time of day. This type of algorithm may be used to prevent hypotension during the night when a patient is sleeping.

In some embodiments, a kit including one or more components of system 700 and a set of instructions for adjusting the stimulation pattern based on input relating to a patient's blood pressure may be provided.

Some embodiments may provide a system for reducing blood pressure configured to deliver stimulation at a rate higher than the natural heart rate based on sensed natural heart rate or natural excitation. For example, the system may be configured to sense the natural excitation between delivery of stimulation pulses and if a natural activity is sensed, the system may be configured to inhibit the delivery of the stimulation pulse to the chamber. If in a given time frame the amount of sensed activations exceeds a threshold, the natural heart rate may be regarded as higher than the rate of delivery of the stimulation pulses, in which case the rate of delivery may be increased, e.g., to accommodate increased heart rate of a patient. On the other hand, if in a given time frame the amount of sensed activations is lower than a threshold (this threshold may be 0), the natural heart beat may be regarded as lower than the rate of delivery of the stimulation pulses, in which case the rate of delivery may be reduced, e.g., to avoid over excitation of a patient's heart. To achieve this effect, according to one embodiment, a system for reducing blood pressure may include a sensor for sensing an excitation rate of at least one of an atrium and a ventricle of a patient's heart, a stimulation circuit configured to deliver stimulation pulses to an atrium and a ventricle, and a processor circuit coupled to the stimulation circuit. The processor circuit may be configured to detect the patient's heart rate based on the sensing and operate in an operating mode in which a stimulation pulse is provided to each of the at least one of an atrium and a ventricle. The stimulation pulse may be delivered at a rate that is higher than the sensed excitation rate and may be configured to stimulate the ventricle at a time between about 50 ms before and about 70 ms after stimulation of the atrium.

Some embodiments may provide a system for reducing blood pressure based on a predicted next atrial contraction. For example, a system for reducing blood pressure may include a sensor for sensing an excitation rate of at least one of an atrium and a ventricle, a stimulation circuit configured to deliver a stimulation pulse to at least one of an atrium and a ventricle, and a processor circuit coupled to the stimulation circuit. The processor circuit may be configured to operate in an operating mode in which a timing of a next atrial excitation is predicted based on the sensed excitation rate of the previous atrial excitations, and at least one ventricle is stimulated at a time between about 50 ms before and about 10 ms after the predicted next atrial excitation. The predicted timing may be based on the time interval between the two previous sensed atrial excitations and on a function that will be based on previously sensed time intervals between atrial excitations. The function may include the change in time interval, the rate of change in time intervals, and/or detection of periodic variations in time intervals (e.g., periodic variation due to breathing).

Optionally, a sensor for sensing the excitation rate of at least one of an atrium and a ventricle may comprise an electrode for sensing atrial excitation.

In a further aspect, prediction of a next atrial contraction may be based on a function of previous sensed excitations including rate of change of intervals and periodic variations.

In a further aspect, the timing of the predicted next atrial excitation may be adjusted to reflect a delay between an atrial excitation and a sensing of the atrial excitation.

In a further aspect, the system may further comprise an additional sensor for sensing a parameter relating to cardiac activity and for adjusting the time at which the ventricle is stimulated accordingly. The parameter may be a member of a group consisting of data relating to blood pressure, blood flow, AV valve status, and wall motion of the heart or a part thereof. The additional sensor may be selected from the group consisting of pressure sensors, impedance sensors, ultrasound sensors, and/or one or more audio sensors and/or one or more blood flow sensors. The additional sensor may be implantable.

Reducing Atrial Kick

Some embodiments stem from the inventors realization that blood pressure can be reduced by causing a closure of at least one AV valve during at least part of an atrial contraction. This will reduce, or even prevent, the contribution of the contraction of the atria to the filling of the ventricles, and thus reduce cardiac filling at the end of diastole and consequently reduce blood pressure.

In some embodiments, at least part of an atrial contraction may occur against a closed AV valve. For example, in some embodiments, 40% or more of an atrial contraction may occur against a closed AV valve. In some embodiments, at least 80% of an atrial contraction may occur against a closed AV valve. For example the contraction may start approximately 20 ms or less before the contraction of the ventricle or the excitation of the atria may occur 20 ms or less before the excitation of the ventricle. In some embodiments, 100% of an atrial contraction may occur against a closed AV valve, in which case ventricle excitation is timed such that ventricle contraction will begin before the commencement of atrial contraction. This may include exciting the ventricle before the onset of atrial excitation. The higher the percentage is of an atrial contraction that occurs with the AV valve closed, the more the atrial kick is reduced. Stimulation of both the atrium and the ventricle may provide better control of the percentage of an atrial contraction occurring against a closed valve. Various embodiments may be implemented to cause at least part of an atrial contraction to occur against a closed valve. For example, the AV valve may be closed 70 ms or less after the onset of mechanical contraction of the atrium or 40 ms or less after the onset of mechanical contraction of the atrium or even 5 or 10 ms or less after the onset of mechanical contraction of the atrium. In some embodiments, the AV valve may be closed before the onset of mechanical contraction of the atrium. For example, the AV valve may be closed within 5 ms before the onset of the mechanical contraction of the atrium. In some embodiments, the AV valve may be closed at the same time as the onset of the mechanical contraction. In some embodiments, the AV valve may be closed after the onset of the mechanical contraction of the atrium. For example, the AV valve may be closed within 5 ms after the onset of mechanical contraction of the atrium.

In some embodiments, the onset of a contraction of a chamber may be sensed and a stimulation pulse may be timed relative to the sensed onset of a contraction. The onset of contraction in a chamber is the start of active generation of contractile force in the chamber. The onset of contraction can be sensed by a rapid change in pressure that is not related to the flow of blood into the chamber. The onset of contraction may also be sensed by measuring the movement of the walls of a cardiac chamber or measuring the reduction in volume of a chamber using an ultrasound. These methods of sensing the onset of a contraction may have a delay between the actual onset of the contraction and the sensing of an onset of contraction.

In some embodiments, the AV valve may be closed after the onset of contraction of at least one atrium. For example, the AV valve may be closed about 0 ms to about 70 ms after the onset of contraction of at least one atrium. In some embodiments, the AV valve may be closed about 0 ms to about 40 ms after the onset of contraction of at least one atrium. In some embodiments, the AV valve may be closed about 0 ms to about 10 ms after the onset of contraction of at least one atrium. In some embodiments, the AV valve may be closed about 0 ms to about 5 ms after the onset of contraction of at least one atrium.

Typically, an atrial contraction may begin about 40 ms to about 100 ms after the onset of atrial excitation. In some embodiments, the AV valve may be closed after the onset of atrial excitation. For example, the AV valve may be closed about 40 ms to about 170 ms after the onset of atrial excitation. For example, the AV valve may be closed about 40 ms to about 110 ms after the onset of atrial excitation. In another embodiment, the AV valve may be closed about 40 ms to about 80 ms after the onset of atrial excitation. For example, the AV valve may be closed about 40 ms to about 75 ms after the onset of atrial excitation. For example, the AV valve may be closed about 40 ms to about 50 ms after the onset of atrial excitation.

In some embodiments, the onset of excitation in a chamber may be sensed and a stimulation pulse may be timed relative to the sensed onset of excitation. The onset of excitation is the initiation of a propagating action potential through a chamber. The onset of excitation may be sensed by sensing the local electrical activity of a chamber using a sensing electrode connected to an amplifier. The onset of excitation can also be detected by electrocardiography.

In some embodiments, methods of sensing the onset of excitation may have a delay between the actual onset of the excitation and the sensing of an onset of excitation. The timing of a sensed atrial excitation may be determined by taking into account the delay between actual onset of excitation and the sensing thereof. For example, if a sensing delay is estimated to be 20-40 ms, and stimulation pulses are to be delivered 0-70 ms after onset of atrial excitation, a system may be set to deliver pulses between 40 ms before the next anticipated sensing event to 30 ms after the next anticipated sensing event or 30 ms after the next sensing event. Likewise, if the stimulation pulses are to be delivered to the ventricle 0-50 ms before onset of atrial excitation, assuming the same 20-40 ms sensing delay, a system may be set to deliver pulses between 40 ms before the next anticipated sensing event to 90 ms before the next anticipated sensing event. Sensing delays may be due to one or more of a distance between the site of onset of excitation and a sensing electrode, the level of the electrical signal, characteristics of the sensing circuit, and the threshold set of a sensing event. The delay may include, for example, the duration of the signal propagation from the origin of excitation to the electrode location, the duration related to the frequency response of the sensing circuit, and/or the duration necessary for the signal propagation energy to reach a level detectable by a sensing circuit. The delay may be significant and can range, for example, between about 5 ms to about 100 ms. One approach for estimating the delay is to use the time difference between an AV delay measured when both atrium and ventricle are sensed and the AV delay when the atrium is paced and the ventricle is sensed. Other approaches may use calculation of the amplifier response time based on the set threshold, signal strength, and frequency content. Other approaches may include modifying the delay used with atrial sensing until the effect on blood pressure is the same as the effect obtained by pacing both atrium and ventricle with the desired AV delay.

In some embodiments, the AV valve may be closed before the onset of excitation or contraction of at least one atrium. For example, the AV valve may be closed within about 0 ms to about 5 ms before the onset of excitation or contraction of at least one atrium. In some embodiments, the AV valve may be closed at the same time as the onset of excitation or contraction of at least one atrium.

In some embodiments, direct mechanical control of AV valve closure may be performed. In such embodiments, a mechanical device or a portion thereof may be implanted in the patient, and operated to cause the closing of a valve between the atrium and ventricle. For example, an artificial valve may be implanted in the patient's heart and operated to close mechanically in accordance with some embodiments. In such embodiments, instead of or in addition to providing a stimulation pattern, the aforementioned closure of the AV valves may be accomplished by controlling the functioning of the implanted valve.

In some embodiments, a shortened or even negative time interval between the onset of atrial excitation and ventricular excitation is employed to reduce cardiac filling, thereby reducing blood pressure. As used herein, a negative time interval between the onsets of atrial excitation and ventricular excitation means that in a single cardiac cycle, the onset of excitation for the at least one ventricle occurs before the onset of atrial excitation. In this case, atrial contraction may take place, at least partially, against a closed AV valve, since the generated pressure in the ventricles may be greater than the pressure in the atria. A short time after the initiation of ventricular contraction, the pressure in the ventricles may exceed the pressure in the atria and may result in the passive closure of the valve. This closure of the valve may reduce or even obliterate the atrial kick and, in turn, reduce ventricular filling. Consequently, the force of ventricular contraction may be reduced and blood pressure may drop.

The time between the start of excitation and the start of the mechanical contraction in each cardiac chamber is not fixed. Thus, the timing of excitation does not guarantee the same effect on the timing between contractions. However, in some embodiments, the timing between excitations is used as a frame of reference for practical reasons. The ultimate purpose of controlling the timing of excitation is to control the timing of a contraction.

In some embodiments, a shortened or even negative time interval between the onset of atrial contraction and ventricular contraction may be employed to reduce cardiac filling, thereby reducing blood pressure. In this case, better control over the contribution of the atria may be obtained since the start of the contraction of the ventricle will result with the closure of the valve.

In some embodiments, 40% or more of an atrial contraction may occur during ventricular systole. For example, the atrial contraction may start approximately 60 ms or less before the contraction of the ventricle, or the excitation of the atria may occur 60 ms or less before the excitation of the ventricle. In some embodiments 80% or more of an atrial contraction may occur during ventricular systole. For example, the contraction may start approximately 20 ms or less before the contraction of the ventricle, or the excitation of the atria may occur 20 ms or less before the excitation of the ventricle. In some embodiments, 100% of an atrial contraction may occur during ventricular systole, in which case ventricle excitation is timed such that ventricle contraction will begin before the commencement of atrial contraction. This may include exciting the ventricle before the onset of atrial excitation.

Some embodiments provide a method for causing the contraction of at least one ventricle of a heart, such that the at least one ventricle contracts during or before the contraction of the corresponding atrium. One way to achieve this goal is by exciting the ventricle at a point in time between about 50 ms before to about 70 ms after the onset of excitation of the corresponding atrium. In some embodiments, the time interval between the onset of excitation of at least one ventricle and the onset of excitation of the corresponding atrium may be zero. In other words, the onset of excitation for the at least one ventricle may occur at the same time as the onset of excitation of the corresponding atrium. In some embodiments, the onset of excitation of the ventricle may occur between about 0 ms to about 50 ms before the onset of atrial excitation. In some embodiments, the onset of excitation of the ventricle may occur at least 2 ms before to at least 2 ms after the onset of excitation of the at least one atrium. In some embodiments, the onset of excitation of the ventricle may occur at least 10 ms before to at least 10 ms after the onset of excitation of the at least one atrium. In some embodiments, the onset of excitation of the ventricle may occur at least 20 ms before to at least 20 ms after the onset of excitation of the at least one atrium. In some embodiments, the onset of excitation of the ventricle may occur at least 40 ms before to at least 40 ms after the onset of excitation of the at least one atrium.

In some embodiments, a method may comprise delivering a stimulation pulse from a stimulation circuit to at least one of an atrium and a ventricle, and operating a processor circuit coupled to the stimulation circuit to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. The time interval between the onset of atrial excitation and the moment that atrial excitation is sensed may be known and used to calculate the timing of the onset of atrial excitation. For example, if it is known that atrial excitation is sensed 20 ms after the onset of atrial excitation and the ventricle is to be stimulated 40 ms before the onset of atrial excitation, then the ventricle is to be stimulated 60 ms before the anticipated sensing of atrial excitation. In other embodiments, the method may comprise operating a processor circuit coupled to the stimulation circuit to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments, atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

In some embodiments, a device may comprise a stimulation circuit configured to deliver a stimulation pulse to at least one of an atrium and a ventricle. The device may comprise a processor circuit coupled to the stimulation circuit. In some embodiments, the processor circuit may be configured to operate in an operating mode in which a ventricle is stimulated to cause ventricular excitation to commence between about 0 ms and about 50 ms before the onset of atrial excitation in at least one atrium, thereby reducing the ventricular filling volume from the pretreatment ventricular filling volume and reducing the patient's blood pressure from the pretreatment blood pressure. In such embodiments, atrial excitation may be sensed to determine the onset of atrial excitation. The time interval between the onset of atrial excitation and the moment that atrial excitation is sensed may be known and used to calculate the timing of the onset of atrial excitation. For example, if it is known or estimated that atrial excitation is sensed 20 ms after the onset of atrial excitation and the ventricle is to be stimulated 40 ms before the onset of atrial excitation, then the ventricle is to be stimulated 60 ms before the anticipated sensing of atrial excitation. In other embodiments, the processor circuit may be configured to operate in an operating mode in which an atrium is stimulated to cause atrial excitation to commence between about 0 ms and about 50 ms after the onset of ventricular excitation in at least one ventricle, thereby reducing the ventricular filling volume from the pretreatment ventricular filling volume and reducing the patient's blood pressure from the pretreatment blood pressure. For example, the processor circuit may be configured to operate in an operating mode in which one or more excitatory pulses are delivered to an atrium between about 0 ms and about 50 ms after one or more excitatory pulses are provided to the patient's ventricle. In such embodiments, the pacing may be timed without relying on sensing atrial excitation. Optionally, in such embodiments atrial excitation is sensed in order to confirm that one or more excitatory pulses are delivered to an atrium before a natural excitation takes place. Optionally, atrial excitation is set to commence between about 0 ms and about 50 ms after the onset of ventricular excitation when the intrinsic atrial excitation rate is lower than the intrinsic ventricular excitation rate.

Figure 10A:
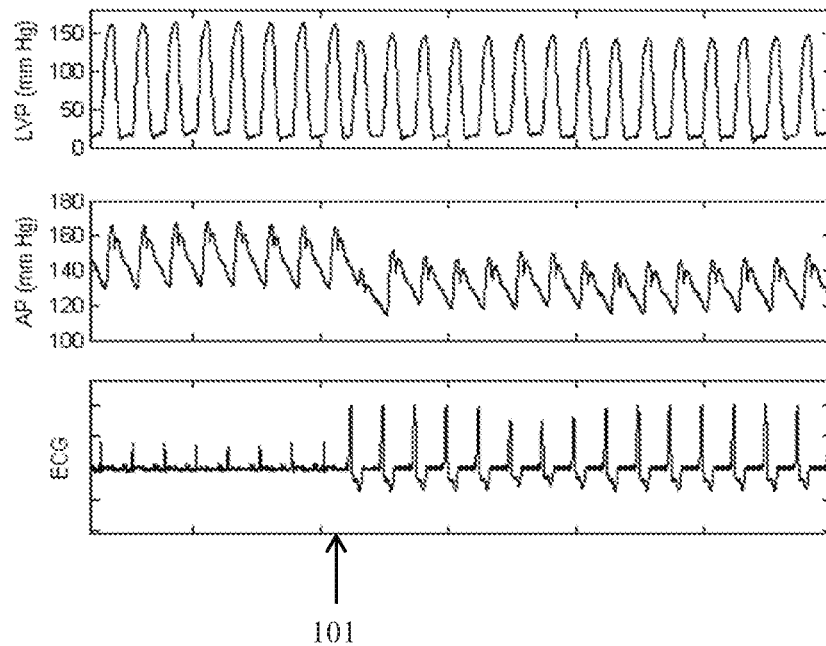
FIG. 10A shows a time plot including: electrocardiogram, aortic pressure and left ventricular pressure of a healthy canine heart.
Figure 10B:
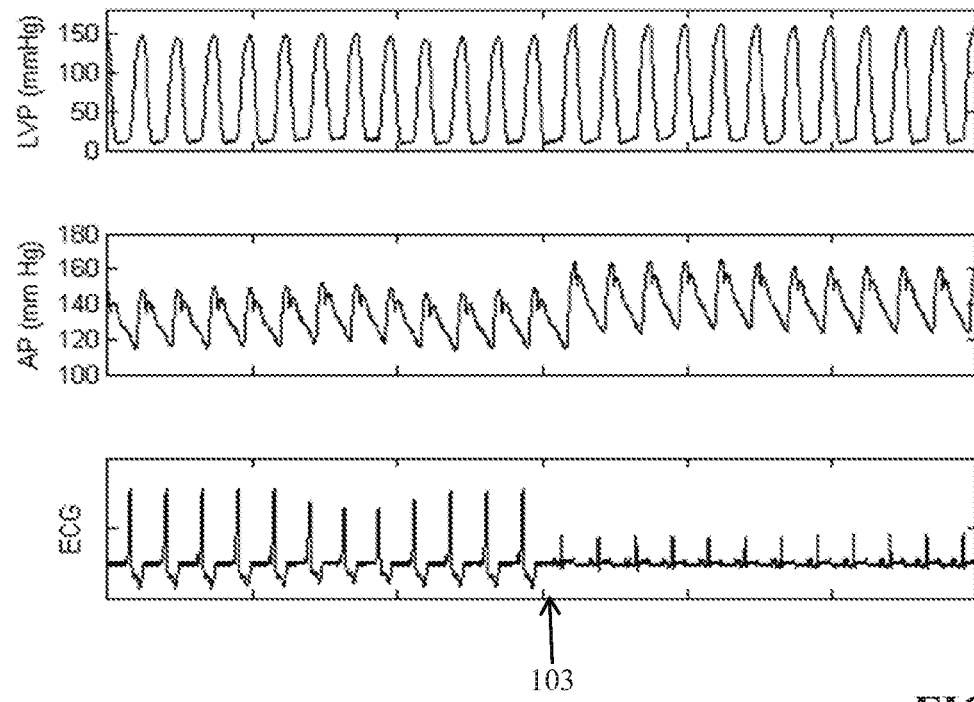
FIG. 10B shows a time plot including: electrocardiogram, aortic pressure and left ventricular pressure of a healthy canine heart.

FIGS. 10A and 10B depict a healthy anesthetized canine heart, showing an electrocardiogram (ECG), left ventricle pressure (LVP) and arterial (blood) pressure (AP) traced over a period of time. In FIG. 10A, before point 101, the heart was allowed to beat naturally, and the ECG, LVP, and AP were traced. At point 101, ventricular pacing commenced. The ventricle was paced 2 ms after the onset of atrial excitation. This pacing caused an immediate change in the ECG, which was concomitant with a reduction of both LVP and AP. The pacing continued at a 2 ms time interval between the onset of atrial contractions and the onset of ventricular pacing until point 103 in FIG. 10B, where pacing ceased. As seen, immediately upon cessation of pacing, the ECG, LVP, and BP all returned essentially to the same values as before pacing.

Figure 11A:
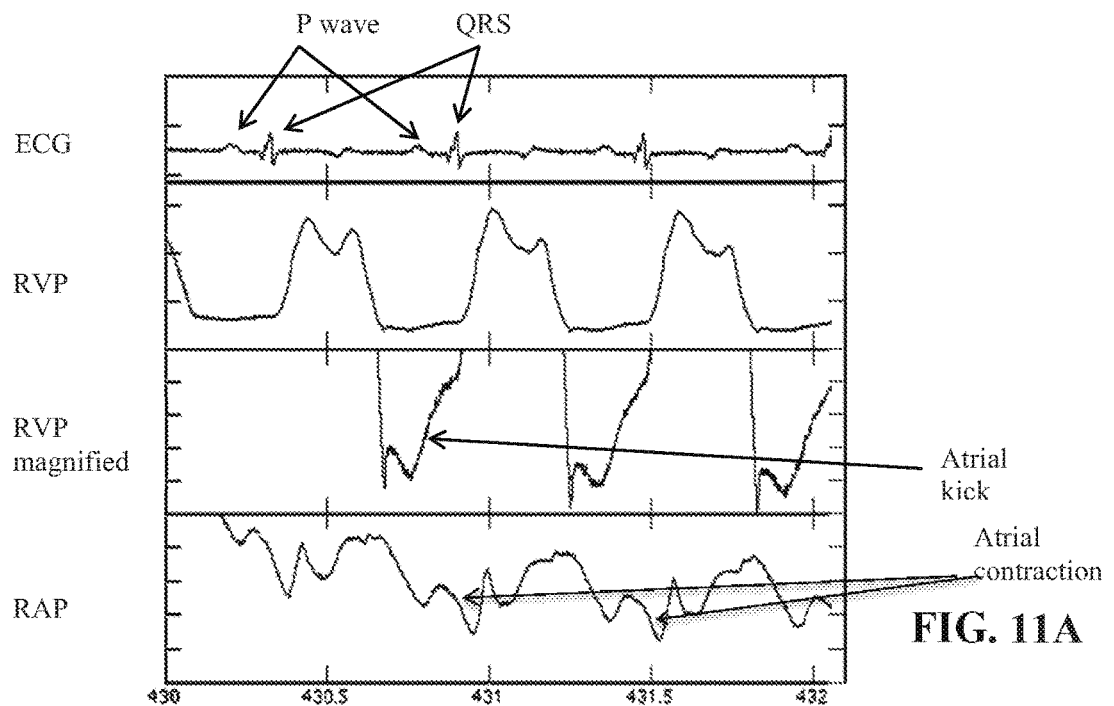
FIG. 11A shows a time plot of a hypertensive canine heart, including right atria pressure, magnified diastolic portion of right ventricular pressure, right ventricular pressure and electrocardiogram.
Figure 11B:
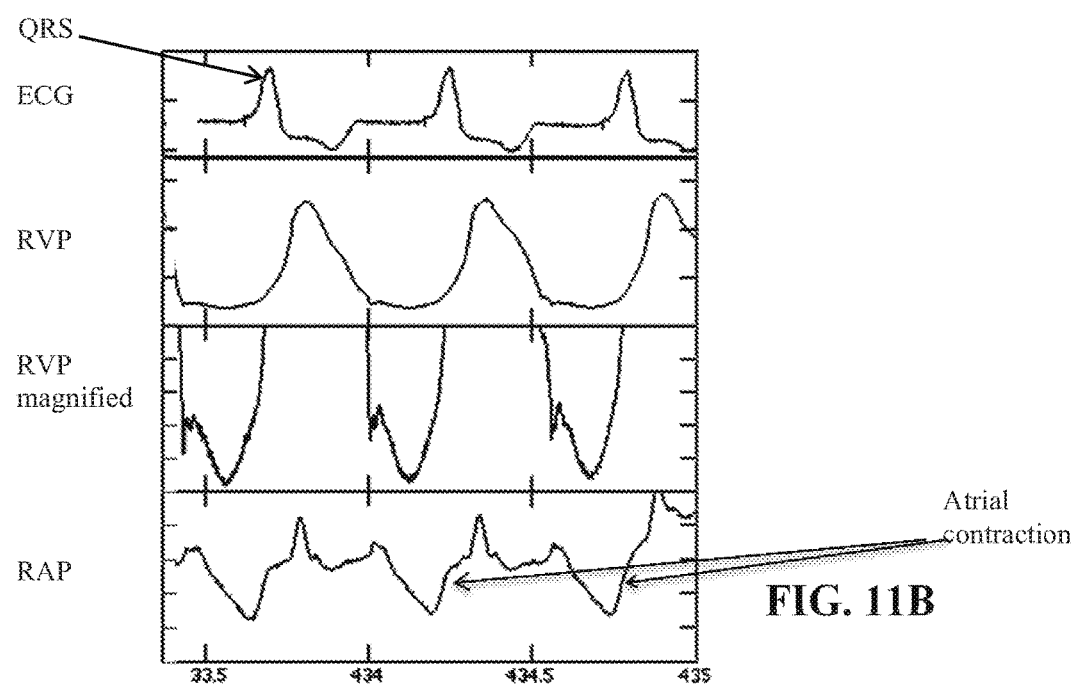
FIG. 11B shows a time plot of a hypertensive canine heart, including right atria pressure, magnified diastolic portion of right ventricular pressure, right ventricular pressure and electrocardiogram.

FIGS. 11A and 11B show a hypertensive canine heart under a natural heartbeat (FIG. 11A) and when paced at a time interval of 2 ms between the onset of atrial contractions and ventricular pacing (FIG. 11B). Each of these figures shows traces of an ECG, right ventricular pressure (RVP), a magnified portion of the RVP, and right atrial pressure (RAP) of the heart.

In FIG. 11A, the P wave and QRS of the natural heartbeat are clearly seen. An increase in atrial pressure is seen following the P wave as a result of atrial contraction. In the RVP trace, a sharp increase in RVP is seen following a QRS complex on the ECG. This is a manifestation of ventricular contraction. When observed at a higher magnification, this sharp increase in RVP is preceded by an earlier, smaller increase in RVP, which coincides with atrial contraction and a reduction in atrial pressure and is a result of blood emptying from the atrium into the chamber. This is the atrial kick. In FIG. 11B, where pacing is at a time interval of 2 ms, the P wave is essentially unnoticeable on the ECG, and an artifact of the electrical stimulator is discernible. The atrial kick in this case is not visible on the magnified trace of right ventricular pressure because the atrial contraction occurred at the same time or even a little after the start of ventricular contraction.

In FIG. 12, a hypertensive canine heart was paced either at a time interval of 60 ms between the pacing of the atria and the pacing of the ventricle (trace portions 105 and 107) or a time interval 120 ms of between atrial and ventricular pacing (trace portion 109). The trace shows the ECG of the heart, left ventricular pressure (LVP), right ventricular pressure (RVP), a magnification of RVP, and right atrial pressure (RAP). As seen in trace portions of RVP magnified corresponding with trace portions 105 and 107, the atrial kick during pacing at the 60 ms time interval is very slight and the contraction of the ventricle begins slightly after the peak of atrial contraction. In this case the contribution of atrial kick to ventricular filling is markedly reduced but not totally eliminated and, on the other end, the peak of atrial contraction does not occur against a closed valve and atrial stretch does not increase. During pacing at a time interval of 120 ms, the atrial kick is clearly seen (portion 109 in trace RVP magnified), but the start of the ventricular contraction and the closure of the AV valve occur before the completion of atrial contraction, thereby slightly reducing the contribution of the atrial kick to ventricular filling.

Figure 16:
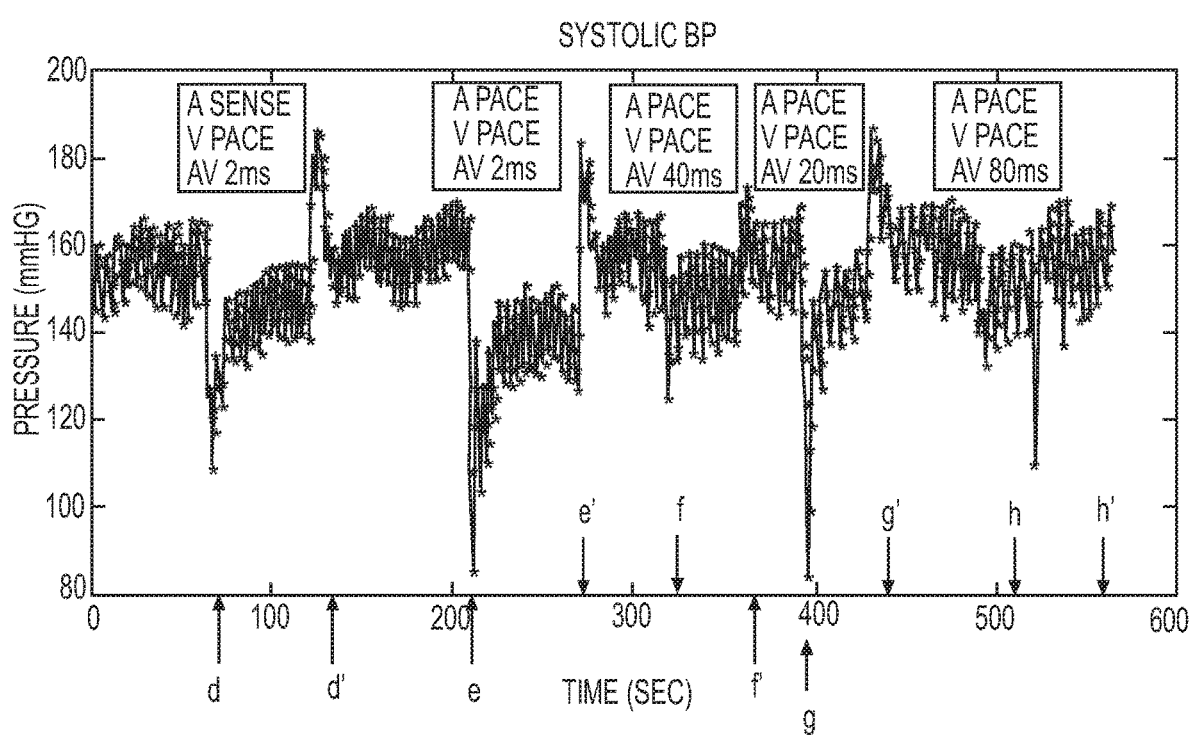
FIG. 16 shows the systolic blood pressure of a hypertensive patient receiving a stimulation signal, plotted against time.

In FIG. 16, the heart of a hypertensive patient was paced with different AV delays. This example shows the results obtained by pacing in both an atrium and a corresponding ventricle versus pacing only the ventricle based on the sensed pulses in the atrium. During interval d-d', atrial pulses were sensed and ventricular pulses were paced with an AV delay of 2 ms. During interval e-e', the atrium and ventricle were both paced with an AV delay of 2 ms. During interval f-f', the atrium and the ventricle were both paced with an AV delay of 40 ms. During interval g-g', the atrium and the ventricle were both paced with an AV delay of 20 ms. During interval h-h', the atrium and the ventricle were both paced with an AV delay of 80 ms. As shown in this example, when comparing interval d-d' with interval e-e', the blood pressure is reduced more when the atrium is paced during interval e-e' than when atrial activity was just sensed. As also shown in this example, when comparing interval e-e', interval f-f', interval g-g', and interval h-h', the shorter AV delays caused more of a reduction in blood pressure than the longer ones. For example, interval g-g' (20 ms AV-delay) shows a higher blood pressure than interval e-e' (2 ms AV-delay). As shown from the results of this example, the changes in blood pressure may be caused at least partially by the different AV delays, which result in different percentages of atrial contraction against a closed valve.

Exemplary Embodiments of Methods for Reducing Atrial Kick

Figure 13:
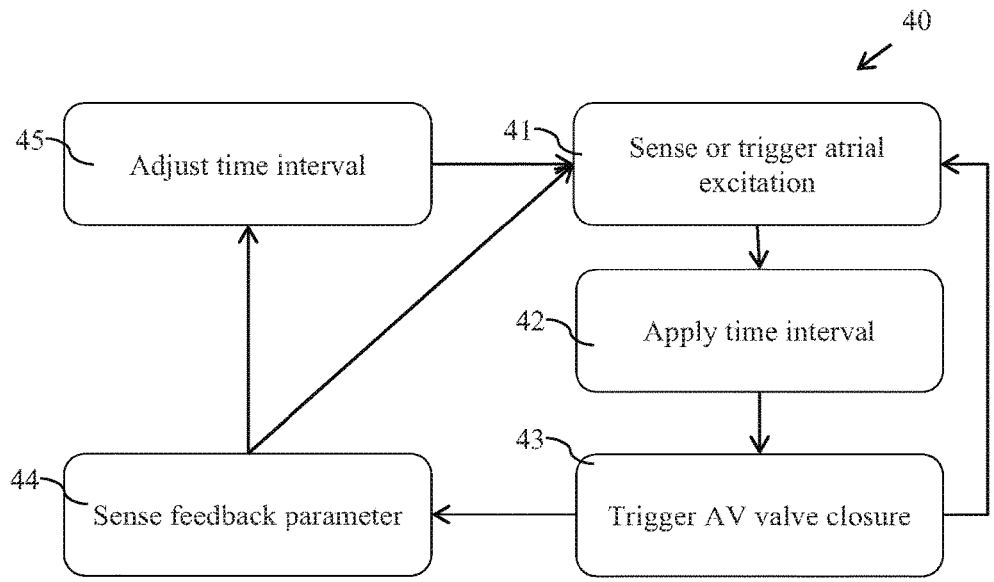
FIG. 13 is a flow chart showing an exemplary method 40 for reducing blood pressure.

An exemplary method 40 for reducing blood pressure is depicted schematically in FIG. 13. Method 40 may be performed by device 50 of FIG. 14, described below. Accordingly, device 50 may be configured to perform any or all steps of method 40. Similarly, method 40 may include any steps device 50 is configured to perform. For example, method 40 may include any of the functions discussed above with respect to device 50. Method 40 may include any steps from method 600. Similarly, method 600 may include any steps from method 40. Method 40 may include any steps that system 700 may be configured to perform. System 700 may be configured to perform any or all steps of method 40.

In some embodiments, method 40 may include a step 41 of atrial excitation. In some embodiments, step 41 includes sensing an atrial excitation. For example, step 41 may include sensing an intrinsic atrial excitation. In some embodiments, step 41 includes triggering atrial excitation. Method 40 may include a step 42 in which a time interval is applied. Method 40 may include a step 43 of triggering AV valve closure. In some embodiments, step 43 may be performed by applying an excitatory current to the at least one ventricle and/or by actuating an artificial valve between the at least one atrium and the corresponding ventricle(s) to close. In some embodiments, step 41, step 42, and step 43 may be repeated as depicted by a return arrow leading back to step 41 from step 43. In some embodiments, an excitatory current may be applied to both ventricles, at the same time or in sequence. In some embodiments, where both ventricles are paced in sequence, the time interval may be measured between the onset of excitation of at least one atrium (e.g., the right atrium) and the onset of excitation of the corresponding ventricle to be paced (e.g., the right ventricle). In some embodiments, where the time interval is set to be zero or negative, step 43 may be performed before or at the same time as step 41. In some embodiments, the time interval may be measured in milliseconds.

Optionally, contraction of the atrium and the ventricle may be caused by controlling both contractions (e.g. by controlling the excitations leading to the contractions). Optionally, the onset of excitation of the atrium is sensed, which sensing triggers the closing of a valve at the prescribed timing interval. Optionally, both atria are paced. In some embodiments, where both AV valves are closed in sequence (e.g., as both ventricles are paced in sequence), the timing interval is measured from the onset of excitation of the first atrium to be paced and the onset of the valve closing or the onset of excitation of at least one ventricle. Optionally the timing of an excitation (e.g. the onset of excitation) of one or more chambers is estimated, for example based on the timing in one or more preceding heart cycles, and one or more excitation stimuli are delivered to the same and/or to a different chamber at a desired time interval before and/or after the estimated timing.

In some embodiments, method 40 may be repeated for every heartbeat. In some embodiments, method 40 may be performed intermittently. For example, the method may be applied once every few heartbeats. Alternatively, method 40 may be applied for a few heartbeats, stopped for one or more heartbeats, and then applied again. For example, method 40 may be applied for 5 to 15 heartbeats, stopped for 2 to 5 heartbeats, and then resumed again. In some embodiments, the pattern of application/avoiding application may be more complex and may be optionally based on a predefined algorithm. For example, an algorithm may adjust parameters of stimulation rather than simply stop and start stimulation. Application of method 40 in some embodiments reduces ventricle filling between heartbeats thereby potentially reducing the ejection profile. As used herein, the ejection profile of a heart is the total amount of blood pumped by the heart in a given period of time. In some embodiments, an intermittent application of method 40 may be applied to counteract a reduction in the ejection profile of the heart.

In some embodiments, the time interval applied in step 42 may be selected based on feedback. In such cases, method 40 may include step 44 of sensing a feedback parameter from one or more of the heart chambers, any portion thereof, and/or the body of the patient. For example, feedback information may be obtained by monitoring directly or indirectly one or more of the atrial kick, blood pressure (e.g., at an artery), ventricular pressure, and/or atrial pressure. In some embodiments, feedback information may additionally or alternatively include the degree of overlap between the time when the atrium contracts and the time when the AV valve is closed and/or the time when the ventricle contracts. For example, an ultrasound sensor may be used to detect cardiac activity, for example, by ultrasound imaging of cardiac activity or by creating an echocardiogram (ECHO). In some embodiments, step 44 may include using an ultrasound sensor to detect the flow of blood (e.g., the velocity of flow) and/or cardiac tissue movement at any arbitrary point using pulsed or continuous wave Doppler ultrasound.

Optionally, step 44 may include using an ultrasound sensor to detect an A wave corresponding to the contraction of the left atrium and the flow of blood to the left ventricle.

Method may include a step 45 of adjusting the time interval from step 42 based on the feedback information from step 44. For example, step 45 may include adjusting the time interval based on a sensed blood pressure. As shown by the arrow directed from step 45 to step 41 in FIG. 13, step 41, step 42, step 43, and/or step 44 may be repeated after performing step 45. In some embodiments, the time interval may be initially set at a first value during step 41 and, based on feedback sensing performed during step 44, the time interval may be reduced or increased during step 45 until the feedback value is within a given range (or above or below a given value). For example, the time interval may be adjusted until such time that systolic blood pressure is above 100 mmHg and/or below 140 mmHg and/or diastolic blood pressure is below 90 mmHg and/or above 60 mmHg.

In some embodiments, step 44 and step 45 may be performed during operation of method 40 for every application of step 43 (e.g., application of a ventricular pacing stimulus). In some embodiments, alternatively or additionally, step 44 and step 45 may be performed upon providing a device to a patient (e.g., by implantation of the device) according to one or more embodiments. The adjusting steps may be repeated periodically (for example by a care taker during a checkup) and/or intermittently (for example once an hour or once every few applications of a ventricular pacing stimulus). In some embodiments, step 45 may be performed when feedback information indicates that one or more sensed parameters exceed a preset range for a period of time that exceeds a predefined period.

The steps of method 40 may be performed in any order. For example, the steps may be performed in the order indicated by the arrows shown in FIG. 13. In another embodiment, step 42 may be performed before step 41.

The timing of atrial contraction, atrial excitation, ventricular contraction, closing and/or opening of the AV valve(s), and/or the flow or lack thereof of blood from one or more atria to the respective ventricle(s) and/or blood pressure may be detected by any method known in the art and may be used as feedback control. In some embodiments, the onset of excitation may be used as a trigger for the delivery of an excitatory stimulus to one or more ventricles. The sensed information may be additionally or alternatively be used in the adjusting of a timing interval of the device.

Optionally, feedback parameters may allow responding to conditions that require additional throughput from the heart, and rather than adjust the timing interval they may be used to automatically stop the causing of valve closing at a shortened timing interval. For example, the feedback parameters may lead to an adjustment during exercise. In this example, a heart rate sensor may be used to provide feedback information on the heart rate of the patient. If the heart rate is above a given threshold the feedback may be used to cause the device to stop. The device may be activated again based on sensed feedback information, for example, when the heart rate is below a given threshold and/or after a predetermined period has passed.

Embodiments of Devices for Reducing Blood Pressure

Figure 14:
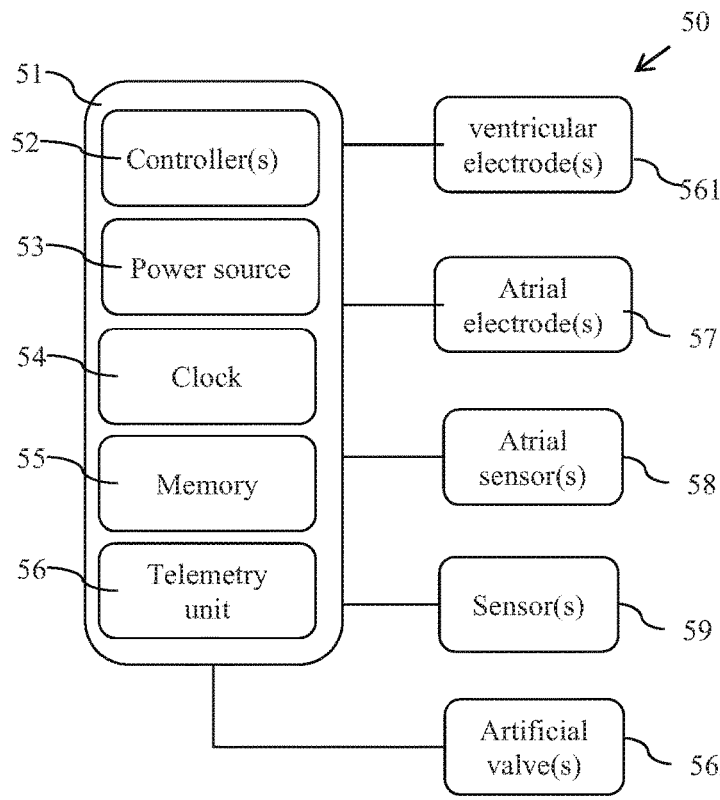
FIG. 14 is a flow chart showing an exemplary method 40 for reducing blood pressure.

Attention is now drawn to FIG. 14, which schematically depicts an exemplary device 50 according to an embodiment. Device 50 may be constructed and have components similar to a cardiac pacemaker essentially as known in the art with some modifications as discussed herein. Optionally, the device is implantable. Optionally, the device comprises components that may provide additional and/or alternative electrical treatments of the heart (e.g., defibrillation). Device 50 may be configured for implantation in the body of a patient essentially as is known in the art for implantable pacemakers, optionally with some modifications as discussed herein. Device 50 may include any components of system 700 and system 700 may include any components of device 50.

Device 50 may include a biocompatible body 51, one or more controllers 52, a power source 53, and a telemetry unit 56. Body 51 may comprise a housing for encasing a plurality of components of the device. Controller(s) 52 may be configured to control the operation of the device. For example, controller(s) 52 may control the delivery of stimulation pulses. In some embodiments, power source 53 may include a battery. For example, power source 53 may include a rechargeable battery. In some embodiments, power source 53 may include a battery that is rechargeable by induction. In some embodiments, telemetry unit 56 may be configured to communicate with one or more other units and/or components. For example, telemetry unit 56 may be configured to communicate with an external programmer and/or a receiving unit for receiving data recorded on device 50 during operation.

In some embodiments, device 50 may be configured to be attached to one or more electrodes and/or sensors. The electrodes and/or sensors may be integrated in device 50, attached thereto, and/or connectable therewith. In some embodiments, the electrodes may include ventricular electrode(s) 561 configured to pace at least one ventricle. Additionally or alternatively, the device may be connected, optionally via wires or wirelessly, to at least one implanted artificial valve 562. Additionally, device 50 may comprise one or more atrial electrode(s) 57 for pacing one or more atria, and/or one or more atrial sensors 58 for sensing the onset of atrial excitation, and/or one or more sensors 59 for providing other feedback parameters.

In some embodiments, sensor(s) 59 may comprise one or more pressure sensors, electrical sensors (e.g., ECG monitoring), flow sensors, heart rate sensors, activity sensors, and/or volume sensors. Sensor(s) 59 may include mechanical sensors and/or electronic sensors (e.g., ultrasound sensors, electrodes, and/or RF transceivers). In some embodiments, sensor(s) 59 may communicate with device 50 via telemetry.

In some embodiments, ventricular electrode(s) 561 and/or atrial electrode(s) 57 may be standard pacing electrodes. Ventricular electrode(s) 561 may be positioned relative to the heart at positions as known in the art for ventricular pacing. For example, ventricular electrode(s) may be placed in and/or near one or more of the ventricles. In some embodiments, atrial electrode(s) 57 may be placed in and/or near one or more of the atria. In some embodiments, atrial electrode(s) 57 may be attached to the one or more atria at one or more positions selected to provide early detection of atrial excitation or depolarization. For example, in some embodiments, atrial electrode(s) 57 may be attached to the right atrium near the site of the sinoatrial (SA) node.

One position of ventricular electrode(s) 561 may be such that pacing may reduce or minimize the prolongation of QRS when the heart is paced, to reduce or even minimize dyssynchrony. In some embodiments, this position is on the ventricular septum near the Bundle of His. Ventricular electrode(s) 561 may additionally or alternatively be placed on the epicardium of the heart or in coronary veins. More than one electrode can be placed on the ventricles to provide biventricular pacing, optionally to reduce dyssynchrony.

Device 50 may include a pulse generator, or stimulation circuit, configured to deliver a stimulation pulse to at least one cardiac chamber. The pulse generator, or stimulation circuit, may include some or all standard capabilities of a conventional pacemaker. Controller 52 may be configured to control the pulse generator, or stimulation circuit. Atrial sensor(s) 58 (and optionally other electrode sensors configured to sense other heart chambers) may be connected to device 50 via specific circuits that will amplify the electrical activity of the heart and allow sampling and detection of the activation of the specific chamber. Other circuits may be configured to deliver stimulation to a specific electrode to pace the heart, creating propagating electrical activation.

In some embodiments, one or more additional sensors 59 may be placed in and/or on one or more of the atria and/or in and/or on one or more of the ventricles and/or in and/or on one or more other locations that might optionally be adjacent the heart. For example, one or more sensors may be placed on and/or in vena cava and/or on one or more arteries and/or within one or more cardiac chambers. These sensors may measure pressure, or other indicators, such as, for example, impedance and/or flow.

In some embodiments, controller 52 may comprise or be a microprocessor powered by power source 53. In some embodiments, device 50 may comprise a clock 54, for example, generated by a crystal. Device 50 may comprise an internal memory 55 and/or be connected to external memory. For example, device may connect to an external memory via telemetry unit 56. In some embodiments, telemetry unit 56 may be configured to allow communication with external devices such as a programmer and/or one or more of sensors 59. Any and all feedback information and/or a log of device operation may be stored in internal memory 55 and/or relayed by telemetry unit 56 to an external memory unit.

In some embodiments, controller 52 may operate in accordance with at least one embodiment of a method described herein.

In some embodiments, device 50 may comprise one or more sensors for sensing one or more feedback parameters to control the application of the AV delay and/or its magnitude.

Embodiments of Artificial Valves

Additionally or alternatively, device 50 may be configured to directly control the operation of at least one implanted artificial valve 562. Attention is now drawn to FIG. 15, which schematically depicts an artificial valve 60 according to an embodiment of the invention. Valve 60 as depicted in the example is a bi-leaflet, essentially as known in the art for artificial valves. While the following example relates to a bi-leaflet valve it is appreciated that embodiments may be implemented in other artificial valves, for example, caged ball valves and disc valves as well.

Figure 15:
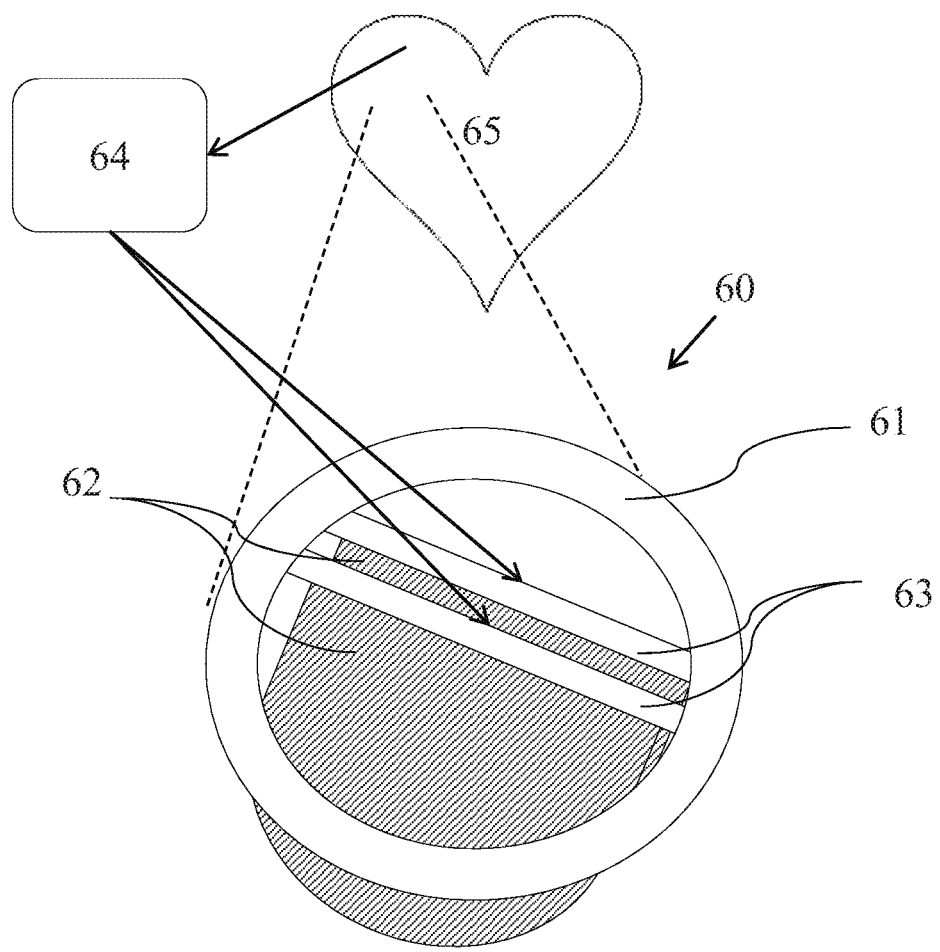
FIG. 15 is a schematic diagram illustrating an artificial valve according to an embodiment.

As shown in FIG. 15, valve 60 may comprise a ring 61 for suturing the valve in place when implanted in a heart of a patient. Valve 60 may include two semicircular leaflets 62 that rotate about struts 63 attached to ring 61. In this schematic representation, other device components are schematically depicted as body 64, which corresponds to body 51 as shown in FIG. 14. Body 64 may receive feedback information from heart 65, in which valve 60 is implanted.

Valve 60 differs from conventional artificial valves in that its closure may be directly controlled by device 50. Valve 60 may comprise a mechanism (for example, a coil or a hydraulic mechanism) that is configured to actively cause closure of the valve (for example, by rotating struts 63 or by inflating a portion of the one or more of leaflets 62). The mechanism may later be brought back to a relaxed position to allow opening of the valve and to allow its repeated closing as needed. The relaxation may be performed at a predetermined time after closing. Additionally or alternatively, relaxation may be affected in response to a sensor reading ventricular activity (e.g., a pressure sensor). Control over valve 60 may be operated wirelessly (using a telemetry unit associated with the valve) or by wired communication with components in body 64. In some embodiments, valve 60 may be a valve configured to be opened and closed independent of fluid pressure acting on the valve. For example, valve 60 may be a ball valve.

Effects of Embodiments for Reducing Blood Pressure

Overall, some embodiments of the disclosed methods and systems provide different approaches to reducing the filling of at least one ventricle, consequently reducing blood pressure. Unlike previous mechanical methods for reducing blood pressure, some embodiments described herein may achieve this goal without increasing pressure within the at least one corresponding atrium. Without an increase in atrial pressure to trigger the secretion of atrial natriuretic hormone, or atrial natriuretic peptide, the reduction of blood pressure can be mechanically controlled. The disclosed embodiments may prevent an unwanted effect on heart rate and may reduce the likelihood of canon atrial waves.

Some of the disclosed embodiments may reduce atrial kick while also increasing atrial stretch, causing the release of atrial natriuretic peptide. For example, disclosed embodiments may comprise a method including a step of stimulating a heart to cause an atrium thereof to contract while a heart valve associated with the atrium is closed such that the contraction distends the atrium. Reducing atrial kick and causing the release of atrial natriuretic peptide at the same time may have a synergistic effect on lowering blood pressure. In some embodiments, controlling the timing of valve closure relative to atrial contraction may control the amount one or more atria stretches.

Unlike previous pharmaceutical or mechanical methods for reducing blood pressure, some of the disclosed embodiments achieve the goal of reducing blood pressure immediately. For example, a reduction in blood pressure may occur within 1-3 sec or within 1, 3, or 5 heartbeats of the application of electricity and the blood pressure may reach a minimal blood pressure value within less than 5 heartbeats from the beginning of stimulation.

Examples discussed above strike a balance between mechanical treatment, neuronal feedback, and the natural release of hormones that cause adaptation. The mechanical treatment and the natural release of hormones may be additive or even synergistic mechanisms. The hormonal release affects the cardiovascular system while the mechanical treatment affects the heart itself. Intermittently delivering the mechanical treatment to reduce blood pressure may affect both the neuronal and hormonal feedback controlling the cardiovascular system and reduce adaptation.

The headings used in this specification are only meant to aid in organization and do not define any terms.

The present disclosure is related to the following applications, all of which are incorporated by reference in their entirety:

U.S. Patent Application Publication Number 2012/0215272 to Levin et al., published on Aug. 23, 2012;

U.S. Patent Application Publication Number 2011/0172731 to Levin et al., published on Jul. 14, 2011;

U.S. patent application Ser. No. 13/688,978 to Levin et al., filed on Nov. 29, 2012; and U.S. Patent Application Publication Number 2012/0041502 to Schwartz et al., published on Feb. 16, 2012.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

What is claimed is:

1. A system for reducing blood pressure comprising:
at least one stimulation electrode for stimulating at least one chamber of a heart of a patient with a stimulation pattern comprising at least one stimulation pulse; and
at least one controller configured to:
receive input relating to blood pressure of the patient; and
adjust the stimulation pattern based on the blood pressure,
wherein the stimulation pattern is configured to cause a reduction in blood pressure of the patient by at least a predetermined amount within about 3 seconds from an application of electricity to the heart, and to maintain the reduction in blood pressure for a time interval of at least 1 minute.

2. The system of claim 1, wherein the at least one controller is configured to adjust the stimulation pattern by performing an adjustment process that includes adjusting a parameter of a first stimulation setting of at least one of the at least one stimulation pulse.

3. The system of claim 2, wherein the first stimulation setting is configured to reduce or prevent atrial kick in at least one ventricle.

4. The system of claim 3, wherein the parameter is adjustment of AV delay.

5. The system of claim 1, wherein the time interval is at least 5 minutes.

6. The system of claim 1, wherein the predetermined amount of blood pressure reduction is 8 mmHg or more.

7. The system of claim 1, wherein the predetermined amount of blood pressure reduction is at least 4% of a pretreatment blood pressure of the patient.

8. The system of claim 1, wherein the patient's blood pressure does not exceed a predetermined average value during the time interval by more than a predetermined degree.

9. The system of claim 8, wherein the predetermined degree is a difference of about 8 mmHg or less.

10. The system of claim 8, wherein the predetermined degree is a percentage of the predetermined amount within a range of about 26% to 100%.

11. The system of claim 1, wherein the at least one controller is configured to:
execute a plurality of stimulation patterns and receive for each of the stimulation patterns a corresponding input data set relating to the patient's blood pressure during the stimulation;
calculate for each of the plurality of stimulation patterns at least one blood pressure variation parameter relating to the input data set; and
adjust the stimulation pattern according to the at least one blood pressure variation parameter.

12. The system of claim 11, wherein the at least one controller is configured to adjust the stimulation pattern to be the one with the best blood pressure variation parameter.

13. The system of claim 11, wherein at least two stimulation patterns of the plurality of stimulation patterns each comprise at least one stimulation pulse having a stimulation setting configured to reduce or prevent atrial kick in at least one ventricle, and wherein the at least two stimulation patterns differ one from another by the number of times or the length of time the at least one stimulation pulse is provided in sequence.

14. The system of claim 11, wherein the plurality of stimulation patterns differs by the number of times or the length of time that the system is configured to elicit a predetermined AV delay in sequence.

15. The system of claim 11, wherein at least two stimulation patterns of the plurality of stimulation patterns differ one from another by one or more stimulation settings included within each of the at least two stimulation patterns.

16. The system of claim 11, wherein the plurality of stimulation patterns includes a first stimulation pattern and a second stimulation pattern executed after the first stimulation pattern, the second stimulation pattern having at least one stimulation setting that was set based on an algorithm using blood pressure variation parameters relating to the input data set of the first stimulation pattern.

17. The system of claim 11, comprising a blood pressure sensor for providing the input data set relating to the patient's blood pressure.

18. The system of claim 17, wherein the blood pressure sensor is implantable.

19. The system of claim 17, wherein the blood pressure sensor and the at least one controller are configured to operate at least partially as a closed loop.

20. A system for reducing blood pressure comprising:
at least one stimulation electrode for stimulating at least one chamber of a heart of a patient with a stimulation pulse; and
a controller configured to:
provide a first stimulation pattern comprising at least one stimulation setting configured to reduce or prevent atrial kick in at least one ventricle for a first time interval and to receive a first input data set relating to a patient's blood pressure during said first time interval,
wherein the first stimulation pattern is configured to cause a reduction in blood pressure of the patient by at least a predetermined amount within about 3 seconds from an application of electricity to the heart, and to maintain the reduction in blood pressure for a time interval of at least 1 minute;
calculate at least one blood pressure variation parameter relating to the first input data set;
adjust at least one parameter of a second stimulation pattern comprising a second stimulation setting configured to reduce or prevent atrial kick in at least one ventricle, the second stimulation setting being based upon the at least one blood pressure variation parameter; and
provide the second stimulation pattern for a second time interval.

21. The system of claim 20, wherein the controller is configured to adjust the at least one parameter of the second stimulation pattern to provide a lowest degree of baroreflex response, or a lowest degree or a lowest rate of adaptation.

22. A system for reducing blood pressure comprising:
at least one stimulation electrode for stimulating at least one chamber of a heart of a patient with a stimulation pattern comprising at least one stimulation pulse; and at least one controller configured to:
- receive input relating to blood pressure of the patient,
- adjust the stimulation pattern based on the blood pressure,
- execute a plurality of stimulation patterns and receive for each of the stimulation patterns a corresponding input data set relating to the patient's blood pressure during the stimulation,
- calculate for each of the plurality of stimulation patterns at least one blood pressure variation parameter relating to the input data set,
- adjust the stimulation pattern according to the at least one blood pressure variation parameter, to be the one with the best blood pressure variation parameter, and
- wherein the best blood pressure variation parameter is one that displays a lowest degree of baroreflex response, or a lowest degree or a lowest rate of adaptation.

23. A system for reducing blood pressure comprising:

at least one stimulation electrode for stimulating at least one chamber of a heart of a patient with a stimulation pattern comprising at least one stimulation pulse; and at least one controller configured to:
- receive input relating to blood pressure of the patient,
- adjust the stimulation pattern based on the blood pressure,
- execute a plurality of stimulation patterns and receive for each of the stimulation patterns a corresponding input data set relating to the patient's blood pressure during the stimulation,
- calculate for each of the plurality of stimulation patterns at least one blood pressure variation parameter relating to the input data set,
- adjust the stimulation pattern according to the at least one blood pressure variation parameter, to be the one with the best blood pressure variation parameter, and
- wherein the best blood pressure variation parameter is one that displays a baroreflex response within a predetermined range or a degree of adaptation within a predetermined range.

* * * * *